United States Patent
Mogensen et al.

(10) Patent No.: US 6,569,901 B2
(45) Date of Patent: May 27, 2003

(54) ALKYNYL-SUBSTITUTED PROPIONIC ACID DERIVATIVES, THEIR PREPARATION AND USE

(75) Inventors: John Patrick Mogensen, Herlev (DK); Per Sauerberg, Farum (DK); Paul Stanley Bury, Kobenhavn NV (DK); Lone Jeppesen, Virum (DK); Ingrid Pettersson, Frederiksberg (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/771,217

(22) Filed: Jan. 26, 2001

(65) Prior Publication Data
US 2001/0041709 A1 Nov. 15, 2001

Related U.S. Application Data

(60) Provisional application No. 60/181,056, filed on Feb. 8, 2000, provisional application No. 60/217,903, filed on Jul. 13, 2000, and provisional application No. 60/245,370, filed on Nov. 2, 2000.

(30) Foreign Application Priority Data

Jan. 28, 2000 (DK) ......... 2000 00137
Jul. 7, 2000 (DK) ......... 2000 01065
Oct. 25, 2000 (DK) ......... 2000 01593

(51) Int. Cl.[7] ............ A61K 31/235; A61K 31/24; A61K 31/19; C07C 69/76; C07C 62/00
(52) U.S. Cl. ............ 514/532; 514/539; 514/535; 514/537; 514/538; 514/568; 560/55; 560/56; 560/78; 560/80; 560/81; 562/465; 562/470
(58) Field of Search ............ 560/60, 55, 56, 560/76, 80, 81; 562/470, 468; 514/571, 567, 534, 535, 537, 538, 539, 568, 532

(56) References Cited
U.S. PATENT DOCUMENTS 6,150,413 A * 11/2000 Bernardon et al.
6,214,820 B1 * 4/2001 Jeppesen et al.

FOREIGN PATENT DOCUMENTS

| EP | 0 551 035 A1 | 7/1993 |
|---|---|---|
| EP | 0 879 814 A1 | 11/1998 |
| EP | 0 903 343 A1 | 3/1999 |
| WO | WO 94/01420 | 1/1994 |
| WO | WO 95/03313 | 2/1995 |
| WO | WO 96/04260 | 2/1996 |
| WO | WO 96/04261 | 2/1996 |
| WO | WO 97/25042 | 7/1997 |
| WO | WO 97/36579 | 9/1997 |
| WO | WO 99/08501 | 2/1999 |
| WO | WO 99/16758 | 4/1999 |
| WO | WO 99/19313 | 4/1999 |
| WO | WO 99/20614 | 4/1999 |
| WO | WO 99/38850 | 8/1999 |

* cited by examiner

Primary Examiner—Johann Richter
Assistant Examiner—Paul A. Zucker
(74) Attorney, Agent, or Firm—Rosemarie R. Wilk-Orescan; Reza Green

(57) ABSTRACT

The present invention relates to compounds of formula (I)

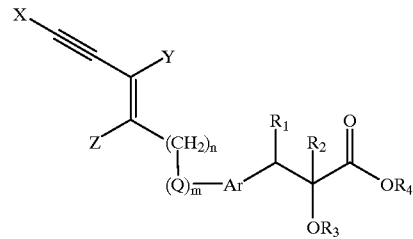

(I)

The compounds are useful in the treatment and/or prevention of conditions mediated by nuclear receptors, in particular the Peroxisome Proliferator-Activated Receptors (PPAR).

60 Claims, No Drawings

ALKYNYL-SUBSTITUTED PROPIONIC ACID DERIVATIVES, THEIR PREPARATION AND USE

CROSS-REFERENCE TO RELATED APPLICATIONS

This application claims priority under 35 U.S.C. 119 of Danish application no. PA 2000 00137 filed on Jan. 28, 2000, Danish application no. PA 2000 01065 filed on Jul. 7, 2000, Danish application no. PA 2000 01593 filed on Oct. 25, 2000, U.S. provisional application No. 60/181,056 filed on Feb. 8, 2000, U.S. provisional application No. 60/217,903 filed on Jul. 13, 2000, and U.S. provisional application No. 60/245,370 filed on Nov. 2, 2000, the contents of which are fully incorporated herein by reference.

FIELD OF INVENTION

The present invention relates to novel compounds, pharmaceutical compositions containing them, methods for preparing the compounds and their use as medicaments. More specifically, compounds of the invention can be utilised in the treatment and/or prevention of conditions mediated by nuclear receptors, in particular the Peroxisome Proliferator-Activated Receptors (PPAR).

BACKGROUND OF THE INVENTION

Coronary artery disease (CAD) is the major cause of death in Type 2 diabetic and metabolic syndrome patients (i.e. patients that fall within the 'deadly quartet' category of impaired glucose tolerance (IGT), insulin resistance, hypertriglyceridaemia and/or obesity).

The hypolipidaemic fibrates and antidiabetic thiazolidinediones separately display moderately effective triglyceride-lowering activities although they are neither potent nor efficacious enough to be a single therapy of choice for the dyslipidaemia often observed in Type 2 diabetic or metabolic syndrome patients. The thiazolidinediones also potently lower circulating glucose levels of Type 2 diabetic animal models and humans. However, the fibrate class of compounds are without beneficial effects on glycaemia. Studies on the molecular actions of these compounds indicate that thiazolidinediones and fibrates exert their action by activating distinct transcription factors of the peroxisome proliferator activated receptor (PPAR) family, resulting in increased and decreased expression of specific enzymes and apolipoproteins respectively, both key-players in regulation of plasma triglyceride content. Fibrates, on the one hand, are PPARα activators, acting primarily in the liver. Thiazolidinediones, on the other hand, are high affinity ligands for PPARγ acting primarily on adipose tissue.

Adipose tissue plays a central role in lipid homeostasis and the maintenance of energy balance in vertebrates. Adipocytes store energy in the form of triglycerides during periods of nutritional affluence and release it in the form of free fatty acids at times of nutritional deprivation. The development of white adipose tissue is the result of a continuous differentiation process throughout life. Much evidence points to the central role of PPARγ activation in initiating and regulating this cell differentiation. Several highly specialised proteins are induced during adipocyte differentiation, most of them being involved in lipid storage and metabolism. The exact link from activation of PPARγ to changes in glucose metabolism, most notably a decrease in insulin resistance in muscle, has not yet been clarified. A possible link is via free fatty acids such that activation of PPARγ induces Lipoprotein Lipase (LPL), Fatty Acid Transport Protein (FATP) and Acyl-CoA Synthetase (ACS) in adipose tissue but not in muscle tissue. This, in turn, reduces the concentration of free fatty acids in plasma dramatically, and due to substrate competition at the cellular level, skeletal muscle and other tissues with high metabolic rates eventually switch from fatty acid oxidation to glucose oxidation with decreased insulin resistance as a consequence.

PPARα is involved in stimulating β-oxidation of fatty acids. In rodents, a PPARα-mediated change in the expression of genes involved in fatty acid metabolism lies at the basis of the phenomenon of peroxisome proliferation, a pleiotropic cellular response, mainly limited to liver and kidney and which can lead to hepatocarcinogenesis in rodents. The phenomenon of peroxisome proliferation is not seen in man. In addition to its role in peroxisome proliferation in rodents, PPARα is also involved in the control of HDL cholesterol levels in, rodents and humans. This effect is, at least partially, based on a PPARα-mediated transcriptional regulation of the major HDL apolipoproteins, apo A-I and apo A-II. The hypotriglyceridemic action of fibrates and fatty acids also involves PPARα and can be summarised as follows: (I) an increased lipolysis and clearance of remnant particles, due to changes in lipoprotein lipase and apo C-III levels, (II) a stimulation of cellular fatty acid uptake and their subsequent conversion to acyl-CoA derivatives by the induction of fatty acid binding protein and acyl-CoA synthase, (III) an induction of fatty acid β-oxidation pathways, (IV) a reduction in fatty acid and triglyceride synthesis, and finally (V) a decrease in VLDL production. Hence, both enhanced catabolism of triglyceride-rich particles as well as reduced secretion of VLDL particles constitutes mechanisms that contribute to the hypolipidemic effect of fibrates.

A number of compounds have been reported to be useful in the treatment of hyperglycemia, hyperlipidemia and hypercholesterolemia (U.S. Pat. No. 5,306,726, PCT Publications nos. WO 91/19702, WO 95/03038, WO 96/04260, WO 94/13650, WO 94101420, WO 97/36579, WO 97/25042, WO 95/17394, WO 99/08501, WO 99/19313 and WO 99/16758).

SUMMARY OF THE INVENTION

Glucose lowering as a single approach does not overcome the macrovascular complications associated with Type 2 diabetes and metabolic syndrome. Novel treatments of Type 2 diabetes and metabolic syndrome must therefore aim at lowering both the overt hypertriglyceridaemia associated with these syndromes as well as alleviation of hyperglycaemia.

The clinical activity of fibrates and thiazolidinediones indicates that research for compounds displaying combined PPARα and PPARγ activation should lead to the discovery of efficacious glucose and triglyceride lowering drugs that have great potential in the treatment of Type 2 diabetes and the metabolic syndrome (i.e. impaired glucose tolerance, insulin resistance, hypertriglyceridaemia and/or obesity).

DETAILED DESCRIPTION OF THE INVENTION

Accordings, the present invention relates to compounds of the general formula (I):

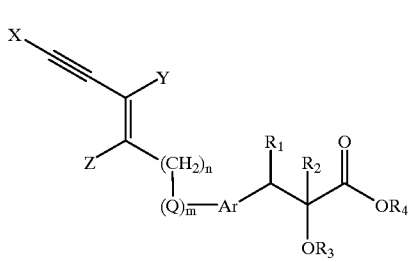

wherein

X is hydrogen or

X is $C_{1-12}$-alkyl, $C_{2-12}$-alkenyl, $C_{2-12}$-alkynyl, aryl, heteroaryl, aralkyl, heteroaralkyl or heterocyclyl each of which is optionally substituted with one or more substituents selected from halogen, perhalomethyl, hydroxy, $C_{1-6}$-alkyl, $C_{2-6}$-alkenyl, $C_{2-6}$-alkynyl, hydroxy, $C_{1-6}$-alkoxy, $C_{1-6}$-alkylthio, aryl, aryloxy, arylthio, acyl, aralkyl, aralkoxy, heteroaryl, heteroaralkyl, heteroaryloxy, heteroaralkoxy, $C_{1-6}$-alkylthio, cyano, amino, $C_{1-6}$-alkylamino, $C_{1-6}$-dialkylamino, carboxy or $C_{1-6}$-alkylester; and Y is hydrogen or Y is $C_{1-12}$-alkyl, $C_{2-12}$-alkenyl, $C_{2-12}$-alkynyl, $C_{4-12}$-alkenynyl, aryl, heteroaryl, aralkyl or heteroaralkyl each of which is optionally substituted with one or more substituents selected from halogen, $C_{1-6}$-alkyl, perhalomethyl, hydroxy, aryl, heteroaryl, amino, carboxy or $C_{1-6}$-alkylester; and Z is hydrogen, halogen, hydroxy or Z is $C_{1-6}$-alkyl or $C_{1-6}$-alkoxy each of which is optionally substituted with one or more substituents selected from $C_{1-6}$-alkoxy, halogen, hydroxy, carboxy, amino or cyano; and Q is O, S or $NR_5$, wherein $R_5$ is hydrogen, $C_{1-6}$-alkyl, $C_{2-6}$-alkenyl, $C_{2-6}$-alkynyl, $C_{4-6}$-alkenynyl, aralkyl or heteroaralkyl and wherein $R_5$ is optionally substituted with one or more substituents selected from halogen, hydroxy, $C_{1-6}$-alkoxy, amino or carboxy; and Ar is arylene, heteroarylene or a divalent heterocyclic group each of which can be optionally substituted with one or more substituents selected from $C_{1-6}$-alkyl, aryl or $C_{1-6}$-alkoxy each of which can be optionally substituted with halogen, hydroxy, carboxy or $C_{1-6}$-alkylester; and $R_1$ is hydrogen, hydroxy or halogen; or $R_1$ forms a bond together with $R_2$; and $R_2$ is hydrogen or $C_{1-6}$-alkyl; or $R_2$ forms a bond together with $R_1$; and $R_3$ is hydrogen, $C_{1-6}$-alkyl, $C_{2-6}$-alkenyl, $C_{2-6}$-alkynyl, $C_{4-6}$-alkenynyl, aryl, aralkyl, $C_{1-6}$-alkoxy$C_{1-6}$-alkyl, acyl, heterocyclyl, heteroaryl or heteroaralkyl groups optionally substituted with one or more substituents selected from halogen, perhalomethyl, hydroxy, cyano, carboxy or $C_{1-6}$alkylester; and $R_4$ is hydrogen, $C_{1-6}$-alkyl, $C_{2-6}$-alkenyl, $C_{2-6}$-alkynyl, $C_{4-6}$-alkenynyl or aryl;

n is an integer ranging from 0 to 3; and m is an integer ranging from 0 to 1;

or a pharmaceutically acceptable salt thereof, or a pharmaceutically acceptable solvate thereof, or any tautomeric forms, stereoisomers, mixture of stereoisomers including a racemic mixture, or polymorphs.

In a preferred embodiment, the present invention is concerned with compounds of formula (I)

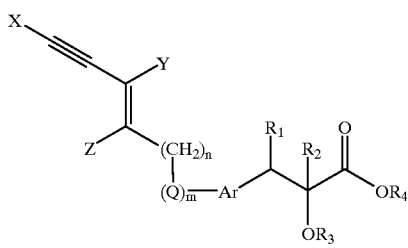

wherein

X is hydrogen or

X is $C_{1-12}$-alkyl, $C_{2-12}$-alkenyl, $C_{2-12}$-alkynyl, aryl, heteroaryl, aralkyl, heteroaralkyl or heterocyclyl each of which is optionally substituted with one or more substituents selected from haloen, perhalomethyl, hydroxy, $C_{1-6}$-alkyl, $C_{2-6}$-alkenyl, $C_{2-6}$-alkynyl, hydroxy, $C_{1-6}$-alkoxy, $C_{1-6}$-alkylthio, aryl, aryloxy, arylthio, acyl, aralkyl, aralkoxy, heteroaryl, heteroaralkyl, heteroaryoxy, heteroaralkoxy, $C_{1-6}$-alkylthio, cyano, amino, $C_{1-6}$-alkylamino, $C_{1-6}$-dialkylamino, carboxy or $C_{1-6}$-alkylester; and Y is hydrogen or Y is $C_{1-12}$-alkyl, $C_{2-12}$-alkenyl, $C_{2-12}$-alkynyl, $C_{4-12}$-alkenynyl, aryl, heteroaryl, aralkyl or heteroaralky each of which is optionally substituted with one or more substituents selected from halogen, $C_{1-6}$-alkyl, perhalomethyl, hydroxy, aryl, heteroaryl, amino, carboxy or $C_{1-6}$-alkylester; and Z is hydrogen, halogen, hydroxy or Z is $C_{1-6}$-alkyl or $C_{1-6}$-alkoxy each of which is optionally substituted with one or more substituents selected from $C_{1-6}$-alkoxy, halogen, hydroxy, carboxy, amino or cyano; and Q is O, S or $NR_5$, wherein $R_5$ is hydrogen, $C_{1-6}$-alkyl, $C_{2-6}$-alkenyl, $C_{2-6}$-alkynyl, $C_{4-6}$-alkenynyl, aralkyl or heteroaralkyl and wherein $R_5$ is optionally substituted with one or more substituents selected from halogen, hydroxy, $C_{1-6}$-alkoxy, amino or carboxy; and Ar is arylene, heteroarylene or a divalent heterocyclic group each of which can be optionally substituted with one or more substituents selected from $C_{1-6}$-alkyl, aryl or $C_{1-6}$-alkoxy each of which can be optionally substituted with halogen, hydroxy, carboxy or $C_{1-6}$-alkylester; and $R_1$ is hydrogen, hydroxy or halogen; or $R_1$ forms a bond together with $R_2$; and $R_2$ is hydrogen or $C_{1-6}$-alkyl; or $R_2$ forms a bond together with $R_1$; and $R_3$ is hydrogen, $C_{1-6}$-alkyl, $C_{2-6}$-alkenyl, $C_{2-6}$-alkynyl, $C_{4-6}$-alkenynyl, aryl, aralkyl, $C_{1-6}$-alkoxy$C_{1-6}$-alkyl, acyl, heterocyclyl, heteroaryl or heteroaralkyl groups optionally substituted with one or more substituents selected from halogen, perhalomethyl, hydroxy, cyano, carboxy or $C_{1-6}$-alkylester; and $R_4$ is hydrogen, $C_{1-6}$-alkyl, $C_{2-6}$-alkenyl, $C_{2-6}$-alkynyl, $C_{4-6}$-alkenynyl or aryl;

n is an integer ranging from 1 to 3; and m is 1;

or a pharmaceutically acceptable salt thereof, or a pharmaceutically acceptable solvate thereof, or any tautomeric forms, stereoisomers, mixture of stereoisomers including a racemic mixture, or polymorphs.

In another preferred embodiment, the present invention is, concerned with compounds of formula I

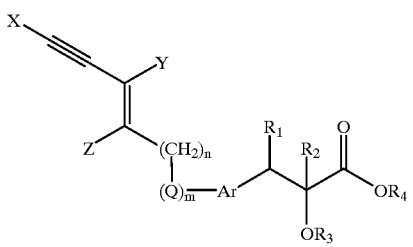

(I)

wherein

X is hydrogen, $C_{1-12}$-alkyl, $C_{2-12}$-alkenyl, $C_{2-12}$-alkynyl, aryl, heteroaryl, aralkyl, heteroaralkyl or heterocyclyl optionally substituted with one or more substituents selected from halogen, perhalomethyl, hydroxy, $C_{1-6}$-alkyl, $C_{2-6}$-alkenyl, $C_{2-6}$-alkynyl, hydroxy, $C_{1-6}$-alkoxy, $C_{1-6}$-alkylthio, aryl, aryloxy, arylthio, acyl, aralkyl, aralkoxy, heteroaryl, heteroaralkyl, heteroaryloxy, heteroaralkoxy, $C_{1-6}$-alkylthio, cyano, amino, $C_{1-6}$-alkylamino, $C_{1-6}$-dialkylamino, carboxy or $C_{1-6}$-alkylester; and Y is hydrogen, $C_{1-12}$-alkyl, $C_{2-12}$-alkenyl, $C_{2-12}$-alkynyl, $C_{4-12}$-alkenynyl, aryl, heteroaryl, aralkyl or heteroaralkyl optionally substituted with one or more substituents selected from halogen, $C_{1-6}$-alkyl, perhalomethyl, hydroxy, aryl, heteroaryl, amino, carboxy or $C_{1-6}$-alkylester; and Z is hydrogen, halogen, hydroxy, $C_{1-6}$-alkyl or $C_{1-6}$-alkoxy optionally substituted with one or more substituents selected from $C_{1-6}$-alkoxy, halogen, hydroxy, carboxy, amino or cyano; and Q is O, S or $NR_5$, wherein $R_5$ is hydrogen, $C_{1-6}$-alkyl, $C_{2-6}$-alkenyl, $C_{2-6}$-alkynyl, $C_{4-6}$-alkenynyl, aralkyl or heteroaralkyl and wherein $R_5$ is optionally substituted with one or more substituents selected from halogen, hydroxy, $C_{1-6}$-alkoxy, amino or carboxy; and Ar is arylene, heteroarylene or a divalent heterocyclic group each of which can be optionally substituted with one or more substituents selected from $C_{1-6}$-alkyl, aryl or $C_{1-6}$-alkoxy each of which can be optionally substituted with halogen, hydroxy, carboxy or $C_{1-6}$-alkylester; and $R_1$ is hydrogen, hydroxy or halogen; or $R_1$ forms a bond together with $R_2$; and $R_2$ is hydrogen or $C_{1-6}$-alkyl; or $R_2$ forms a bond together with $R_1$; and $R_3$ is hydrogen, $C_{1-6}$-alkyl, $C_{2-6}$-alkenyl, $C_{2-6}$-alkynyl, $C_{4-6}$-alkenynyl, aryl, aralkyl, $C_{1-6}$-alkoxy$C_{1-6}$-alkyl, acyl, heterocyclyl, heteroaryl or heteroaralkyl groups optionally substituted with one or more substituents selected from halogen, perhalomethyl, hydroxy, cyano, carboxy or $C_{1-6}$-alkylester; and $R_4$ is hydrogen, $C_{1-6}$-alkyl, $C_{2-6}$-alkenyl, $C_{2-6}$-alkynyl, $C_{4-6}$-alkenynyl or aryl;

n is an integer ranging from 0 to 3; and m is an integer ranging from 0 to 1;

or a pharmaceutically acceptable salt thereof, or a pharmaceutically acceptable solvate thereof, or any tautomeric forms, stereoisomers, mixture of stereoisomers including a racemic mixture, or polymorphs.

In another preferred embodiment, the present invention is concerned with compounds of formula I wherein X is aryl, heteroaryl or heterocyclyl optionally substituted with one or more substituents selected from halogen, perhalomethyl, $C_{1-6}$-alkoxy, $C_{1-6}$-alkylthio, aryl, aryloxy, arylthio, aralkyl, aralkoxy, heteroaryl, heteroaralkyl, heteroaryloxy or heteroaralkoxy.

In another preferred embodiment, the present invention is concerned with compounds of formula I wherein X is aryl, heteroaryl or heterocyclyl each of which is optionally substituted with one or more substituents selected from halogen, perhalomethyl, $C_{1-6}$-alkoxy, $C_{1-6}$-alkylthio, aryl, aryloxy, arylthio, aralkyl, aralkoxy, heteroaryl, heteroaralkyl, heteroaryloxy or heteroaralkoxy.

In another preferred embodiment, the present invention is concerned with compounds of formula I wherein X is aryl optionally substituted with one or more substituents selected from halogen, perhalomethyl, $C_{1-6}$-alkoxy, $C_{1-6}$-alkylthio, aryl, aryloxy, arylthio, aralkyl, aralkoxy, heteroaryl, heteroaralkyl, heteroaryloxy or heteroaralkoxy.

In another preferred embodiment, the present invention is concerned with compounds of formula I wherein X is phenyl or naphthyl each of which is optionally substituted with one or more substituents selected from halogen or perhalomethyl.

In another preferred embodiment, the present invention is concerned with compounds of formula I wherein X is phenyl optionally substituted with one or more substituents selected from halogen.

In another preferred embodiment, the present invention is concerned with compounds of formula I wherein X is phenyl.

In another preferred embodiment, the present invention is concerned with compounds of formula I wherein X is heteroaryl optionally substituted with one or more substituents selected from halogen, perhalomethyl, $C_{1-6}$-alkoxy, $C_{1-6}$-alkylthio, aryl, aryloxy, arylthio, aralkyl, aralkoxy, heteroaryl, heteroaralkyl, heteroaryloxy or heteroaralkoxy.

In another preferred embodiment, the present invention is concerned with compounds of formula I wherein X is heterocyclyl optionally substituted with one or more substituents selected from halogen, perhalomethyl, $C_{1-6}$-alkoxy, $C_{1-6}$-alkylthio, aryl, aryloxy, arylthio, aralkyl, aralkoxy, heteroaryl, heteroaralkyl, heteroaryloxy or heteroaralkoxy.

In another preferred embodiment, the present invention is concerned with compounds of formula I wherein Y is hydrogen, $C_{1-12}$-alkyl or aryl.

In another preferred embodiment, the present invention is concerned with compounds of formula I wherein Y is hydrogen or methyl.

In another preferred embodiment, the present invention is concerned with compounds of formula I wherein Y is hydrogen.

In another preferred embodiment, the present invention is concerned with compounds of formula I wherein Z is hydrogen or $C_{1-6}$-alkoxy.

In another preferred embodiment, the present invention is concerned with compounds of formula I wherein Z is hydrogen.

In another preferred embodiment, the present invention is concerned with compounds of formula I wherein Q is O.

In another preferred embodiment, the present invention is concerned with compounds of formula I wherein Ar is arylene optionally substituted with one or more substituents selected from $C_{1-6}$-alkyl or $C_{1-6}$-alkoxy each of which can be optionally substituted with carboxy.

In another preferred embodiment, the present invention is concerned with compounds of formula I wherein Ar is phenylene.

In another preferred embodiment, the present invention is concerned with compounds of formula I wherein $R_1$ is hydrogen or $R_1$ forms a bond together with $R_2$.

In another preferred embodiment, the present invention is concerned with compounds of formula I wherein $R_1$ is hydrogen.

In another preferred embodiment, the present invention is concerned with compounds of formula I wherein $R_2$ is hydrogen or $R_2$ forms a bond together with $R_1$.

In another preferred embodiment, the present invention is concerned with compounds of formula I wherein $R_2$ is hydrogen.

In another preferred embodiment, the present invention is concerned with compounds of formula I wherein $R_3$ is $C_{1-6}$-alkyl.

In another preferred embodiment, the present invention is concerned with compounds of formula I wherein $R_3$ is $C_{1-2}$-alkyl.

In another preferred embodiment, the present invention is concerned with compounds of formula I wherein $R_4$ is hydrogen.

In another preferred embodiment, the present invention is concerned with compounds of formula I wherein n is 1.

In another preferred embodiment, the present invention is concerned with compounds of formula I wherein m is 1.

In another preferred embodiment, the present invention is concerned with compounds of formula I wherein alkyl is methyl or ethyl.

In another preferred embodiment, the present invention is concerned with compounds of formula I wherein alkenyl is vinyl or 1-propenyl.

In another preferred embodiment, the present invention is concerned with compounds of formula I wherein alkynyl is 1-propynyl.

In another preferred embodiment, the present invention is concerned with compounds of formula I wherein alkenynyl is 1-pentene-4-yne.

In another preferred embodiment, the present invention is concerned with compounds of formula I wherein alkoxy is methoxy, ethoxy, isopropoxy or cyclopropoxy.

In another preferred embodiment, the present invention is concerned with compounds of formula I wherein aryl is phenyl or naphthyl optionally substituted with halogen.

In another preferred embodiment, the present invention is concerned with compounds of formula I wherein arylene is phenylene.

In another preferred embodiment, the present invention is concerned with compounds of formula I wherein halogen is chlorine.

In another preferred embodiment, the present invention is concerned with compounds of formula I wherein perhalomethyl is trifluoromethyl.

In another preferred embodiment, the present invention is concerned with compounds of formula I wherein heteroaryl is furan, pyrrole, pyridine, indole or benzofuran.

In another preferred embodiment, the present invention is concerned with compounds of formula I wherein heteroarylene is furan, pyrrole, pyridine, indole or benzofuran.

In another preferred embodiment, the present invention is concerned with compounds of formula I wherein aralkyl is benzyl.

In another preferred embodiment, the present invention is concerned with compounds of formula I wherein aryloxy is phenoxy.

In another preferred embodiment, the present invention is concerned with compounds of formula I wherein aralkoxy is benzyloxy.

In another preferred embodiment, the present invention is concerned with compounds of formula I wherein n is an integer ranging from 1 to 3 and m is 1.

In another preferred embodiment, the present invention is concerned with compounds of formula I wherein the substituents Z and Y are arranged in a trans-configuration.

In another preferred embodiment, the present invention is concerned with compounds of formula I wherein the substituents Z and Y are arranged in a cis-configuration.

Preferred compounds of the invention are:

(E)-(S)-2-Ethoxy-3-[4-(5-phenyl-pent-2-en-4-ynyloxy)-phenyl]-propionic acid ethyl ester, (E)-(S)-2-Ethoxy-3-[4-(5-phenyl-pent-2-en-4-ynyloxy)-phenyl]-propionic acid, (Z)-(S)-2-Ethoxy-3-[4-(3-methyl-5-phenyl-pent-2-en-4-ynyloxy)-phenyl]-propionic acid ethyl ester, (Z)-(S)-2-Ethoxy-3-[4-(3-methyl-5-phenyl-pent-2-en-4-ynyloxy)-phenyl]-propionic acid, (E)-(S)-2-Ethoxy-3-[4-(3-methyl-5-phenyl-pent-2-en-4-ynyloxy)-phenyl]-propionic acid ethyl ester, (E)-(S)-2-Ethoxy-3-[4-(3-methyl-5-phenyl-pent-2-en-4-ynyloxy)-phenyl]-propionic acid;

or a salt thereof with a pharmaceutically acceptable acid or base, or any optical isomer or mixture of optical isomers, including a racemic mixture, or any tautomeric forms.

Also preferred compounds of the invention are:

Ethyl (E)-(S)-2-ethoxy-3-[4-(3-methyl-5-(3,5-dichloro-phenyl)-pent-2-en-4-ynyloxy)-phenyl]-propionate, (E)-(S)-2-ethoxy-3-[4-(3-methyl-5-(3,5-dichloro-phenyl)-pent-2-en-4-ynyloxy)-phenyl]propionic acid, Ethyl (Z)-(S)-2-ethoxy-3-[4-(3-methyl-5-(3,5-dichloro-phenyl)-pent-2-en-4-ynyloxy)-phenyl]-propionate, (Z)-(S)-2-ethoxy-3-[4-(3-methyl-5-(3,5-dichloro-phenyl)-pent-2-en-4-ynyloxy)-phenyl]-propionic acid, Ethyl (E)-(S)-2-ethoxy-3-[4-(3-methyl-5-(3-trifluoromethyl-phenyl)-pent-2-en-4-ynyloxy)-phenyl]-propionate, (E)-(S)-2-ethoxy-3-[4-(3-methyl-5-(3-trifluoromethyl-phenyl)-pent-2-en-4-ynyloxy)-phenyl]-propionic acid, Ethyl (Z)-(S)-2-ethoxy-3-[4-(3-methyl-5-(3-trifluoromethyl-phenyl)-pent-2-en-4-ynyloxy)-phenyl]-propionate, (Z)-(S)-2-ethoxy-3-[4-(3-methyl-5-(3-trifluoromethyl-phenyl)-pent-2-en-4-ynyloxy)-phenyl]-propionic acid;

or a salt thereof with a pharmaceutically acceptable acid or base, or any optical isomer or mixture of optical isomers, including a racemic mixture, or any tautomeric forms.

Also preferred compounds of the invention are:

Ethyl (E)-(S)-2-ethoxy-3-[4-(3-methyl-5-(1-naphthyl)-pent-2-en-4-ynyloxy)-phenyl]-propionate, (E)-(S)-2-ethoxy-3-[4-(3-methyl-5-(1-naphthyl)-pent-2-en-4-ynyloxy)-phenyl]-propionic acid, Ethyl (Z)-(S)-2-ethoxy-3-[4-(3-methyl-5-(1-naphthyl)-pent-2-en-4-ynyloxy)-phenyl]-propionate, (Z)-(S)-2-ethoxy-3-[4-(3-methyl-5-(1-naphthyl)-pent-2-en-4-ynyloxy)-phenyl]-propionic acid, Ethyl (E)-(S)-2-ethoxy-3-[4-(-5-(3,5-dichloro-phenyl)-pent-2-en-4-ynyloxy)-phenyl]-propionate, (E)-(S)-2-ethoxy-3-[4-(5-(3,5-dichloro-phenyl)-pent-2-en-4-ynyloxy)-phenyl]-propionic acid, Ethyl (Z)-(S)-2-ethoxy-3-[4-(3-methyl-5-(3,5-dichloro-phenyl)-pent-2-en-4-ynyloxy)-phenyl]-propionate, (Z)-(S)-2-ethoxy-3-[4-(3-methyl-5-(3,5-dichloro-phenyl)-pent-2-en-4-ynyloxy)-phenyl]-propionic acid;

or a salt thereof with a pharmaceutically acceptable acid or base, or any optical isomer or mixture of optical isomers, including a racemic mixture, or any tautomeric forms.

Also preferred compounds of the invention are:

(Z)-(S)-2-Ethoxy-3-[4-(5-phenyl-pent-2-en-4-ynyloxy)-phenyl]-propionic acid ethyl ester, (Z)-(S)-2-Ethoxy-3-[4-(5-phenyl-pent-2-en-4-ynyloxy)-phenyl]-propionic acid, (E)-(RS)-2-Ethoxy-3-[3-(5-phenyl-pent-2-en-4-ynyloxy)-phenyl]-propionic acid ethyl ester;

or a salt thereof with a pharmaceutically acceptable acid.or base, or any optical isomer or mixture of optical isomers, including a racemic mixture, or any tautomeric forms.

Also preferred compounds of the invention are:

(E)-(S)-3-{4-[5-(1,3-Difluoro-phenyl)-pent-2-en-4-ynyloxy]-phenyl}-2-ethoxy-propionic acid, (E)-(S)-3-{4-[5-(1,3-Dibromo-phenyl)-pent-2-en-4-ynyloxy]-phenyl}-2-ethoxy-propionic acid, (E)-(S)-3-{4-[5-(1,3-Diiodo-phenyl)-pent-2-en-4-ynyloxy]-phenyl}-2-ethoxy-propionic acid, (E)-(S)-3-{4-[5-(1,3-Bis-trifluoromethyl-phenyl)-pent-2-en-4-ynyloxy]-phenyl}-2-ethoxy-propionic acid, (E)-(S)-3-{4-[5-(1,3-Dimethoxy-phenyl)-pent-2-en-4-ynyloxy]-phenyl}-2-ethoxy-propionic acid, (E)-(S)-3-{4-[5-(1,3-Diethoxy-phenyl)-pent-2-en-4-ynyloxy]-phenyl}-2-ethoxy-propionic acid, (E)-(S)-3-{4-[5-(1,3-Bis-(2,2,2-trifluoromethoxy)-phenyl)-pent-2-en-4-ynyloxy]-phenyl}-2-ethoxy-propionic acid, (E)-(S)-3-{4-[5-(1,3-Bis-(2,2,2-trifluoroethoxy)-phenyl)-pent-2-en-4-ynyloxy]-phenyl}-2-ethoxy-propionic acid, (E)-(S)-3-{4-[5-(3,5-Difluoro-phenyl)-pent-2-en-4-ynyloxy]-phenyl}-2-ethoxy-propionic acid, (E)-(S)-3-{4-[5-(3,5-Dibromo-phenyl)-pent-2-en-4-ynyloxy]-phenyl}-2-ethoxy-propionic acid, (E)-(S)-3-{4-[5-(3,5-Diiodo-phenyl)-pent-2-en-4-ynyloxy]-phenyl}-2-ethoxy-propionic acid, (E)-(S)-3-{4-[5-(3,5-Bis-trifluoromethyl-phenyl)-pent-2-en-4-ynyloxy]-phenyl}-2-ethoxy-propionic acid, (E)-(S)-3-{4-[5-(3,5-Dimethoxy-phenyl)-pent-2-en-4-ynyloxy]-phenyl}-2-ethoxy-propionic acid, (E)-(S)-3-{4-[5-(3,5-Diethoxy-phenyl)-pent-2-en-4-ynyloxy]-phenyl}-2-ethoxy-propionic acid, (E)-(S)-3-{4-[5-(3,5-Bis-(2,2,2-trifluoromethoxy)-phenyl)-pent-2-en-4-ynyloxy]-phenyl}-2-ethoxy-propionic acid, (E)-(S)-3-{4-[5-(3,5-Bis-(2,2,2-trifluoroethoxy)-phenyl)-pent-2-en-4-ynyloxy]-phenyl}-2-ethoxy-propionic acid, (E)-(S)-3-{4-[5-(1,3-Difluoro-phenyl)-3-methyl-pent-2-en-4-ynyloxy]-phenyl}-2-ethoxy-propionic acid, (E)-(S)-3-{4-[5-(1,3-Dibromo-phenyl)-3-methyl-pent-2-en-4-ynyloxy]-phenyl}-2-ethoxy-propionic acid, (E)-(S)-3-{4-[5-(1,3-Diiodo-phenyl)-3-methyl-pent-2-en-4-ynyloxy]-phenyl}-2-ethoxy-propionic acid, (E)-(S)-3-{4-[5-(1,3-Bis-trifluoromethyl-phenyl)-3-methyl-pent-2-en-4-ynyloxy]-phenyl}-2-ethoxy-propionic acid, (E)-(S)-3-{4-[5-(1,3-Dimethoxy-phenyl)-pent-2-en-4-ynyloxy]-phenyl}-3-methyl-2-ethoxy-propionic acid, (E)-(S)-3-{4-[5-(1,3-Diethoxy-phenyl)-3-methyl-pent-2-en-4-ynyloxy]-phenyl}-2-ethoxy-propionic acid, (E)-(S)-3-{4-[5-(1,3-Bis-(2,2,2-trifluoromethoxy)-phenyl)-3-methyl pent-2-en-4-ynyloxy]-phenyl}-2-ethoxy-propionic acid, (E)-(S)-3-{4-[5-(1,3-Bis-(2,2,2-trifluoroethoxy)-phenyl)-3-methyl-pent-2-en-4-ynyloxy]-phenyl}-2-ethoxy-propionic acid, (E)-(S)-3-{4-[5-(3,5-Difluoro-phenyl)-3-methyl-pent-2-en-4-ynyloxy]-phenyl}-2-ethoxy-propionic acid, (E)-(S)-3-{4-[5-(3,5-Dibromo-phenyl)-3-methyl-pent-2-en-4-ynyloxy]-phenyl}-2-ethoxy-propionic acid, (E)-(S)-3-{4-[5-(3,5-Diiodo-phenyl)-3-methyl-pent-2-en-4-ynyloxy]-phenyl}-2-ethoxy-propionic acid, (E)-(S)-3-{4-[5-(3,5-Bis-trifluoromethyl-phenyl)-3-methyl-pent-2-en-4-ynyloxy]-phenyl}-2-ethoxy-propionic acid, (E)-(S)-3-{4-[5-(3,5-Dimethoxy-phenyl)-3-methyl-pent-2-en-4-ynyloxy]-phenyl}-2-ethoxy-propionic acid, (E)-(S)-3-{4-[5-(3,5-Diethoxy-phenyl)-3-methyl-pent-2-en-4-ynyloxy]-phenyl}-2-ethoxy-propionic acid, (E)-(S)-3-{4-[5-(3,5-Bis-(2,2,2-trifluoromethoxy)-phenyl)-3-methyl-pent-2-en-4-ynyloxy]-phenyl}-2-ethoxy-propionic acid, (E)-(S)-3-{4-[5-(3,5-Bis-(2,2,2-trifluoroethoxy)-phenyl)-3-methyl-pent-2-en-4-ynyloxy]-phenyl}-2-ethoxy-propionic acid, (E)-(S)-3-{4-[5-(1,3-Difluoro-phenyl)-pent-2-en-4-ynyloxy]-3-chloro-phenyl}-2-ethoxy-propionic acid, (E)-(S)-3-{4-[5-(1,3-Dibromo-phenyl)-pent-2-en-4-ynyloxy]-3-chloro-phenyl}-2-ethoxy-propionic acid, (E)-(S)-3-{4-[5-(1,3-Diiodo-phenyl)-pent-2-en-4-ynyloxy]-3-chloro-phenyl}-2-ethoxy-propionic acid, (E)-(S)-3-{4-[5-(1,3-Bis-trifluoromethyl-phenyl)-pent-2-en-4-ynyloxy]-3-chloro-phenyl}-2-ethoxy-propionic acid, (E)-(S)-3-{4-[5-(1,3-Dimethoxy-phenyl)-pent-2-en-4-ynyloxy]-3-chloro-phenyl}-2-ethoxy-propionic acid, (E)-(S)-3-{4-[5-(1,3-Diethoxy-phenyl)-pent-2-en-4-ynyloxy]-3-chloro-phenyl}-2-ethoxy-propionic acid, (E)-(S)-3-{4-[5-(1,3-Bis-(2,2,2-trifluoromethoxy)-phenyl)-pent-2-en-4-ynyloxy]-3-chloro-phenyl}-2-ethoxy-propionic acid, (E)-(S)-3-{4-[5-(1,3-Bs-(2,2,2-trifluoroethoxy)-phenyl)-pent-2-en-4-ynyloxy]-3-chloro-phenyl}-2-ethoxy-propionic acid, (E)-(S)-3-{4-[5-(3,5-Difluoro-phenyl)-pent-2-en-4-ynyloxy]-3-chloro-phenyl}-2-ethoxy-propionic acid, (E)-(S)-3-{4-[5-(3,5-Dibromo-phenyl)-pent-2-en-4-ynyloxy]-3-chloro-phenyl}-2-ethoxy-propionic acid, (E)-(S)-3-{4-[5-(3,5-Diiodo-phenyl)-pent-2-en-4-ynyloxy]-3-chloro-phenyl}-2-ethoxy-propionic acid, (E)-(S)-3-{4-[5-(3,5-Bis-trifluoromethyl-phenyl)-pent-2-en-4-ynyloxy]-3-chloro-phenyl}-2-ethoxy-propionic acid, (E)-(S)-3-{4-[5-(3,5-Dimethoxy-phenyl)-pent-2-en-4-ynyloxy]-3-chloro-phenyl}-2-ethoxy-propionic acid, (E)-(S)-3-{4-[5-(3,5-Diethoxy-phenyl)-pent-2-en-4-ynyloxy]-3-chloro-phenyl}-2-ethoxy-propionic acid, (E)-(S)-3-{4-[5-(3,5-Bis-(2,2,2-trifluoromethoxy)-phenyl)-pent-2-en-4-ynyloxy]-3-chloro-phenyl}-2-ethoxy-propionic acid, (E)-(S)-3-{4-[5-(3,5-Bis-(2,2,2-trifluoroethoxy)-phenyl)-pent-2-en-4-ynyloxy]-3-chloro-phenyl}-2-ethoxy-propionic acid,
(E)-(S)-3-{4-[5-(1,3-Difluoro-phenyl)-3-methyl-pent-2-en-4-ynyloxy]-3-chioro-phenyl}-2-ethoxy-propionic acid,
(E)-(S)-3-{4-[5-(1,3-Dibromo-phenyl)-3-methyl-pent-2-en-4-ynyloxy]-3-chloro-phenyl}-2-ethoxy-propionic acid,
(E)-(S)-3-{4-[5-(1,3-Diiodo-phenyl)-3-methyl-pent-2-en-4-ynyloxy]-3-chloro-phenyl}-2-ethoxy-propionic acid,
(E)-(S)-3-{4-[5-(1,3-Bis-trifluoromethyo-phenyl)-3-methy)-pent-2-en-4-ynyloxy]-3-chloro-phenyl}-2-ethoxy-propionic acid,
(E)-(S)-3-{4-[5-(1,3-Dimethoxy-phenyl)-pent-2-en-4-ynyloxy]-3-chloro-phenyl}-3-methyl-2-ethoxy-propionic acid,
(E)-(S)-3-{4-[5-(1,3-Diethoxy-phenyl)-3-methyl-pent-2-en-4-ynyloxy]-3-chloro-phenyl}-2-ethoxy-propionic acid,
(E)-(S)-3-{4-[5-(1,3-Bis-(2,2,2-trifluoromethoxy)-phenyl)-3-methyl-pent-2-en-4-ynyloxy]-3-chloro-phenyl}-2-ethoxy-propionic acid,
(E)-(S)-3-{4-[5-(1,3-Bis-(2,2,2-trifluoroethoxy)-phenyl)-3-methyl-pent-2-en-4-ynyloxy]-3-chloro-phenyl}-2-ethoxy-propionic acid,
(E)-(S)-3-{4-[5-(3,5-Difluoro-phenyl)-3-methyl-pent-2-en-4-ynyloxy]-3-chloro-phenyl}-2-ethoxy-propionic acid,
(E)-(S)-3-{4-[5-(3,5-Dibromo-phenyl)-3-methyl-pent-2-en-4-ynyloxy]-3-chloro-phenyl}-2-ethoxy-propionic acid,
(E)-(S)-3-{4-[5-(3,5-Diiodo-phenyl)-3-methyl-pent-2-en-4-ynyloxy]-3-chloro-phenyl}-2-ethoxy-propionic acid,
(E)-(S)-3-{4-[5-(3,5-Bis-trifluoromethyl-phenyl)-3-methyl-pent-2-en-4-ynyloxy]-3-chloro-phenyl}-2-ethoxy-propionic acid,
(E)-(S)-3-{4-[5-(3,5-Dimethoxy-phenyl)-3-methyl-pent-2-en-4-ynyloxy]-3-chloro-phenyl}-2-ethoxy-propionic acid,
(E)-(S)-3-{4-[5-(3,5-Diethoxy-phenyl)-3-methyl-pent-2-en-4-ynyloxy]-3-chloro-phenyl-}2-ethoxy-propionic acid,
(E)-(S)-3-{4-[5-(3,5-Bis-(2,2,2-trifluoromethoxy)-phenyl)-3-methyl-pent-2-en-4-ynyloxy]-3-chloro-phenyl}-2-ethoxy-propionic acid,
(E)-(S)-3-{4-[5-(3,5-Bis-(2,2,2-trifluoroethoxy)-phenyl)-3-methyl-pent-2-en-4-ynyloxy]-3-chloro-phenyl}-2-ethoxy-propionic acid,
(E)-(S)-3-{4-[5-(1,3-Difluoro-phenyl)-pent-2-en-4-ynyloxy]-3-bromo-phenyl}-2-ethoxy-propionic acid,
(E)-(S)-3-{4-[5-(1,3-Dibromo-phenyl)-pent-2-en-4-ynyloxy]-3-bromo-phenyl}-2-ethoxy-propionic acid,
(E)-(S)-3-{4-[5-(1,3-Diiodo-phenyl)-pent-2-en-4-ynyloxy]-3-bromo-phenyl}-2-ethoxy-propionic acid,
(E)-(S)-3-{4-[5-(1,3-Bis-trifluoromethyl-phenyl)-pent-2-en-4-ynyloxy]-3-bromo-phenyl}-2-ethoxy-propionic acid,
(E)-(S)-3-{4-[5-(1,3-Dimethoxy-phenyl)-pent-2-en-4-ynyloxy]-3-bromo-phenyl}-2-ethoxy-propionic acid,
(E)-(S)-3-{4-[5-(1,3-Diethoxy-phenyl)-pent-2-en-4-ynyloxy]-3-bromo-phenyl}-2-ethoxy-propionic acid,
(E)-(S)-3-{4-[5-(1,3-Bis-(2,2,2-trifluoromethoxy)-phenyl)-pent-2-en-4-ynyloxy]-3-bromo-phenyl}-2-ethoxy-propionic acid,
(E)-(S)-3-{4-[5-(1,3-Bis-(2,2,2-trifluoroethoxy)-phenyl)-pent-2-en-4-ynyloxy]-3-bromo-phenyl}-2-ethoxy-propionic acid,
(E)-(S)-3-{4-[5-(3,5-Difluoro-phenyl)-pent-2-en-4-ynyloxy]-3-bromo-phenyl}-2-ethoxy-propionic acid,
(E)-(S)-3-{4-[5-(3,5-Dibromo-phenyl)-pent-2-en-4-ynyloxy]-3-bromo-phenyl}-2-ethoxy-propionic acid,
(E)-(S)-3-{4-[5-(3,5-Diiodo-phenyl)-pent-2-en-4-ynyloxy]-3-bromo-phenyl}-2-ethoxy-propionic acid,
(E)-(S)-3-{4-[5-(3,5-Bis-trifluoromethyl-phenyl)-pent-2-en-4-ynyloxy]-3-bromo-phenyl}-2-ethoxy-propionic acid,
(E)-(S)-3-{4-[5-(3,5-Dimethoxy-phenyl)-pent-2-en-4-ynyloxy]-3-bromo-phenyl}-2-ethoxy-propionic acid,
(E)-(S)-3-{4-[5-(3,5-Diethoxy-phenyl)-pent-2-en-4-ynyloxy]-3-bromo-phenyl}-2-ethoxy-propionic acid,
(E)-(S)-3-{4-[5-(3,5-Bis-(2,2,2-trifluoromethoxy)-phenyl)-pent-2-en-4-ynyloxy]-3-bromo-phenyl}-2-ethoxy-propionic acid,
(E)-(S)-3-{4-[5-(3,5-Bis-(2,2,2-trifluoroethoxy)-phenyl)-pent-2-en-4-ynyloxy]-3-bromo-phenyl}-2-ethoxy-propionic acid,
(E)-(S)-3-{4-[5-(1,3-Difluoro-phenyl)-3-methyl-pent-2-en-4-ynyloxy]-3-bromo-phenyl}-2-ethoxy-propionic acid,
(E)-(S)-3-{4-[5-(1,3-Dibromo-phenyl)-3-methyl-pent-2-en-4-ynyloxy]-3-bromo-phenyl}-2-ethoxy-propionic acid,
(E)-(S)-3-{4-[5-(1,3-Diiodo-phenyl)-3-methyl-pent-2-en-4-ynyloxy]-3-bromo-phenyl}-2-ethoxy-propionic acid,
(E)-(S)-3-{4-[5-(1,3-Bis-trifluoromethyl-phenyl)-3-methyl-pent-2-en-4-ynyloxy]-3-bromo-phenyl}-2-ethoxy-propionic acid,
(E)-(S)-3-{4-[5-(1,3-Dimethoxy-phenyl)-pent-2-en-4-ynyloxy]-3-bromo-phenyl}-3-methyl-2-ethoxy-propionic acid,
(E)-(S)-3-{4-[5-(1,3-Diethoxy-phenyl)-3-methyl-pent-2-en-4-ynyloxy]-3-bromo-phenyl}-2-ethoxy-propionic acid,
(E)-(S)-3-{4-[5-(1,3-Bis-(2,2,2-trfluoromethoxy)-phenyl)-3-methyl-pent-2-en-4-ynyloxy]-3-bromo-phenyl}-2-ethoxy-propionic acid,
(E)-(S)-3-{4-[5-(1,3-Bis-(2,2,2-trifluoroethoxy)-phenyl)-3-methyl-pent-2-en-4-ynyloxy]-3-bromo-phenyl}-2-ethoxy-propionic acid,
(E)-(S)-3-{4-[5-(3,5-Difluoro-phenyl)-3-methyl-pent-2-en-4-ynyloxy]-3-bromo-phenyl}-2-ethoxy-propionic acid,
(E)-(S)-3-{4-[5-(3,5-Dibromo phenyl)-3-methyl-pent-2-en-4-ynyloxy]-3-bromo-phenyl}-2-ethoxy-propionic acid,
(E)-(S)-3-{4-[5-(3,5-Diiodo-phenyl)-3-methyl-pent-2-en-4-ynyloxy]-3-bromo-phenyl}-2-ethoxy-propionic acid,
(E)-(S)-3-{4-[5-(3,5-Bis-trifluoromethyl-phenyl)-3-methyl-pent-2-en-4-ynyloxy]-3-bromo-phenyl}-2-ethoxy-propionic acid,
(E)-(S)-3-{4-[5-(3,5-Dimethoxy-phenyl)-3-methyl-pent-2-en-4-ynyloxy]-3-bromo-phenyl}-2-ethoxy-propionic acid,
(E)-(S)-3-{4-[5-(3,5-Diethoxy-phenyl)-3-methyl-pent-2-en-4-ynyloxy]-3-bromo-phenyl}-2-ethoxy-propionic acid,
(E)-(S)-3-{4-[5-(3,5-Bis-(2,2,2-trifluoromethoxy)-phenyl)-3-methyl-pent-2-en-4-ynyloxy]-3-bromo-phenyl}-2-ethoxy-propionic acid, (E)-(S)-3-{4-[5-(3,5-Bis-(2,2,2-trifluoroethoxy)-phenyl)-3-methyl-pent-2-en-4-ynyloxy]-3-bromo-phenyl}-2-ethoxy-propionic acid,
(E)-(S)-3-{4-[5-(1,3-Difluoro-phenyl)-pent-2-en-4-ynyloxy]-3-iodo-phenyl}-2-ethoxy-propionic acid,
(E)-(S)-3-{4-[5-(1,3-Dibromo-phenyl)-pent-2-en-4-ynyloxy]-3-iodo-phenyl}-2-ethoxy-propionic acid,
(E)-(S)-3-{4-[5-(1,3-Diiodo-phenyl)-pent-2-en-4-ynyloxy]-3-iodo-phenyl}-2-ethoxy-propionic acid,
(E)-(S)-3-{4-[5-(1,3-Bis-trifluoromethyl-phenyl)-pent-2-en-4-ynyloxy]-3-iodo-phenyl}-2-ethoxy-propionic acid,
(E)-(S)-3-{4-[5-(1,3-Dimethoxy-phenyl)-pent-2-en-4-ynyloxy]-3-iodo-phenyl}-2-ethoxy-propionic acid,
(E)-(S)-3-{4-[5-(1,3-Diethoxy-phenyl)-pent-2-en-4-ynyloxy]-3-iodo-phenyl}-2-ethoxy-propionic acid,
(E)-(S)-3-{4-[5-(1,3-Bis-(2,2,2-trifluoromethoxy)-phenyl)-pent-2-en-4-ynyloxy]-3-iodo-phenyl}-2-ethoxy-propionic acid,
(E)-(S)-3-{4-[5-(1,3-Bis-(2,2,2-trifluoroethoxy)-phenyl)-pent-2-en-4-ynyloxy]-3-iodo-phenyl}-2-ethoxy-propionic acid,
(E)-(S)-3-{4-[5-(3,5-Difluoro-phenyl)-pent-2-en-4-ynyloxy]-3-iodo-phenyl}-2-ethoxy-propionic acid,
(E)-(S)-3-{4-[5-(3,5-Dibromo-phenyl)-pent-2-en-4-ynyloxy]-3-iodo-phenyl}-2-ethoxy-propionic acid,
(E)-(S)-3-{4-[5-(3,5-Diiodo-phenyl)-pent-2-en-4-ynyloxy]-3-iodo-phenyl}-2-ethoxy-propionic acid,
(E)-(S)-3-{4-[5-(3,5-Bis-trifluoromethyl-phenyl)-pent-2-en-4-ynyloxy]-3-iodo-phenyl}-2-ethoxy-propionic acid,
(E)-(S)-3-{4-[5-(3,5-Dimethoxy-phenyl)-pent-2-en-4-ynyloxy]-3-iodo-phenyl}-2-ethoxy-propionic acid,
(E)-(S)-3-{4-[5-(3,5-Diethoxy-phenyl)-pent-2-en-4-ynyloxy]-3-iodo-phenyl}-2-ethoxy-propionic acid,
(E)-(S)-3-{4-[5-(3,5-Bis-(2,2,2-trifluoromethoxy)-phenyl)-pent-2-en-4-ynyloxy]-3-iodo-phenyl}-2-ethoxy-propionic acid,
(E)-(S)-3-{4-[5-(3,5-Bis-(2,2,2-trifluoroethoxy)-phenyl)-pent-2-en-4-ynyloxy]-3-iodo-phenyl}-2-ethoxy-propionic acid,
(E)-(S)-3-{4-[5-(1,3-Difluoro-phenyl)-3-methyl-pent-2-en-4-ynyloxy]-3-iodo-phenyl}-2-ethoxy-propionic acid,
(E)-(S)-3-{4-[5-(1,3-Dibromo-phenyl)-3-methyl-pent-2-en-4-ynyloxy]-3-iodo-phenyl}-2-ethoxy-propionic acid,
(E)-(S)-3-{4-[5-(1,3-Diiodo-phenyl)-3-methyl-pent-2-en-4-ynyloxy]-3-iodo-phenyl}-2-ethoxy-propionic acid,
(E)-(S)-3-{4-[5-(1,3-Bis-trifluoromethyl-phenyl)-3-methyl-pent-2-en-4-ynyloxy]-3-iodo-phenyl}-2-ethoxy-propionic acid,
(E)-(S)-3-{4-[5-(1,3-Dimethoxy-phenyl)-pent-2-en-4-ynyloxy]-3-iodo-phenyl}-3-methyl-2-ethoxy-propionic acid,
(E)-(S)-3-{4-[5-(1,3-Diethoxy-phenyl)-3-methyl-pent-2-en-4-ynyloxy]-3-iodo-phenyl}-2-ethoxy-propionic acid,
(E)-(S)-3-{4-[5-(1,3-Bis-(2,2,2-trifluoromethoxy)-phenyl)-3-methyl-pent-2-en-4-ynyloxy]-3-iodo-phenyl}-2-ethoxy-propionic acid,
(E)-(S)-3-{4-[5-(1,3-Bis-(2,2,2-trifluoroethoxy)-phenyl)-3-methyl-pent-2-en-4-ynyloxy]-3-iodo-phenyl}-2-ethoxy-propionic acid,
(E)-(S)-3-{4-[5-(3,5-Difluoro-phenyl)-3-methyl-pent-2-en-4-ynyloxy]-3-iodo-phenyl}-2-ethoxy-propionic acid,
(E)-(S)-3-{4-[5-(3,5-Dibromo-phenyl)-3-methyl-pent-2-en-4-ynyloxy]-3-iodo-phenyl}-2-ethoxy-propionic acid,
(E)-(S)-3-{4-[5-(3,5-Diiodo-phenyl)-3-methyl-pent-2-en-4-ynyloxy]-3-iodo-phenyl}-2-ethoxy-propionic acid,
(E)-(S)-3-{4-[5-(3,5-Bis-trifluoromethyl-phenyl)-3-methyl-pent-2-en-4-ynyloxy]-3-iodo-phenyl}-2-ethoxy-propionic acid,
(E)-(S)-3-{4-[5-(3,5-Dimethoxy-phenyl)-3-methyl-pent-2-en-4-ynyloxy]-3-iodo-phenyl}-2-ethoxy-propionic acid,
(E)-(S)-3-{4-[5-(3,5-Diethoxy-phenyl)-3-methyl-pent-2-en-4-ynyloxy]-3-iodo-phenyl}-2-ethoxy-propionic acid,
(E)-(S)-3-{4-[5-(3,5-Bis-(2,2,2-trifluoromethoxy)-phenyl)-3-methyl-pent-2-en-4-ynyloxy]-3-iodo-phenyl}-2-ethoxy-propionic acid,
(E)-(S)-3-{4-[5-(3,5-Bis-(2,2,2-trifluoroethoxy)-phenyl)-3-methyl-pent-2-en-4-ynyloxy]-3-iodo-phenyl}-2-ethoxy-propionic acid;

or a salt thereof with a pharmaceutically acceptable acid or base, or any optical isomer or mixture of optical isomers, including a racemic mixture, or any tautomeric forms.

Also preferred compounds of the invention are:

(Z)-(S)-3-{4-[5-(1,3-Difluoro-phenyl)-pent-2-en-4-ynyloxy]-phenyl}-2-ethoxy-propionic acid,
(Z)-(S)-3-{4-[5-(1,3-Dibromo-phenyl)-pent-2-en-4-ynyloxy]-phenyl}-2-ethoxy-propionic acid,
(Z)-(S)-3-{4-[5-(1,3-Diiodo-phenyl)-pent-2-en-4-ynyloxy]-phenyl}-2-ethoxy-propionic acid,
(Z)-(S)-3-{4-[5-(1,3-Bis-trifluoromethyl-phenyl)-pent-2-en-4-ynyloxy]-phenyl}-2-ethoxy-propionic acid,
(Z)-(S)-3-{4-[5-(1,3-Dimethoxy-phenyl)-pent-2-en-4-ynyloxy]-phenyl}-2-ethoxy-propionic acid,
(Z)-(S)-3-{4-[5-(1,3-Diethoxy-phenyl)-pent-2-en-4-ynyloxy]-phenyl}-2-ethoxy-propionic acid,
(Z)-(S)-3-{4-[5-(1,3-Bis-(2,2,2-trifluoromethoxy)-phenyl)-pent-2-en-4-ynyloxy]-phenyl}-2-ethoxy-propionic acid,
(Z)-(S)-3-{4-[5-(1,3-Bis-(2,2,2-trifluoroethoxy)-phenyl)-pent-2-en-4-ynyloxy]-phenyl}-2-ethoxy-propionic acid,
(Z)-(S)-3-{4-[5-(3,5-Difluoro-phenyl)-pent-2-en-4-ynyloxy]-phenyl}-2-ethoxy-propionic acid,
(Z)-(S)-3-{4-[5-(3,5-Dibromo-phenyl)-pent-2-en-4-ynyloxy]-phenyl}-2-ethoxy-propionic acid,
(Z)-(S)-3-{4-[5-(3,5-Diiodo-phenyl)-pent-2-en-4-ynyloxy]-phenyl}-2-ethoxy-propionic acid,
(Z)-(S)-3-{4-[5-(3,5-Bis-trifluoromethyl-phenyl)-pent-2-en-4-ynyloxy]-phenyl}-2-ethoxy-propionic acid,
(Z)-(S)-3-{4-[5-(3,5-Dimethoxy-phenyl)-pent-2-en-4-ynyloxy]-phenyl}-2-ethoxy-propionic acid,
(Z)-(S)-3-{4-[5-(3,5-Diethoxy-phenyl)-pent-2-en-4-ynyloxy]-phenyl}-2-ethoxy-propionic acid,
(Z)-(S)-3-{4-[5-(3,5-Bis-(2,2,2-trifluoromethoxy)-phenyl)-pent-2-en-4-ynyloxy]-phenyl}-2-ethoxy-propionic acid,
(Z)-(S)-3-{4-[5-(3,5-Bis-(2,2,2-trifluoroethoxy)-phenyl)-pent-2-en-4-ynyloxy]-phenyl}-2-ethoxy-propionic acid, (Z)-(S)-3-{4-[5-(1,3-Difluoro-phenyl)-3-methyl-pent-2-en-4-ynyloxy]-phenyl}-2-ethoxy-propionic acid, (Z)-(S)-3-{4-[5-(1,3-Dibromo-phenyl)-3-methyl-pent-2-en-4-ynyloxy]-phenyl}-2-ethoxy-propionic acid, (Z)-(S)-3-{4-[5-(1,3-Diiodo-phenyl)-3-methyl-pent-2-en-4-ynyloxy]-phenyl}-2-ethoxy-propionic acid, (Z)-(S)-3-{4-[5-(1,3-Bis-trifluoromethyl-phenyl)-3-methyl-pent-2-en-4-ynyloxy]-phenyl}-2-ethoxy-propionic acid, (Z)-(S)-3-{4-[5-(1,3-Dimethoxy-phenyl)-pent-2-en-4-ynyloxy]-phenyl}-3-methyl-2-ethoxy-propionic acid, (Z)-(S)-3-{4-[5-(1,3-Diethoxy-phenyl)-3-methyl-pent-2-en-4-ynyloxy]-phenyl}-2-ethoxy-propionic acid, (Z)-(S)-3-{4-[5-(1,3-Bis-(2,2,2-trifluoromethoxy)-phenyl)-3-methyl pent-2-en-4-ynyloxy]-phenyl}-2-ethoxy-propionic acid, (Z)-(S)-3-{4-[5-(1,3-Bis-(2,2,2-trifluoroethoxy)-phenyl)-3-methyl-pent-2-en-4-ynyloxy]-phenyl}-2-ethoxy-propionic acid, (Z)-(S)-3-{4-[5-(3,5-Difluoro-phenyl)-3-methyl-pent-2-en-4-ynyloxy]-phenyl}-2-ethoxy-propionic acid, (Z)-(S)-3-{4-[5-(3,5-Dibromo-phenyl)-3-methyl-pent-2-en-4-ynyloxy]-phenyl}-2-ethoxy-propionic acid, (Z)-(S)-3-{4-[5-(3,5-Diiodo-phenyl)-3-methyl-pent-2-en-4-ynyloxy]-phenyl}-2-ethoxy-propionic acid, (Z)-(S)-3-{4-[5-(3,5-Bis-trifluoromethyl-phenyl)-3-methyl-pent-2-en-4-ynyloxy]-phenyl}-2-ethoxy-propionic acid, (Z)-(S)-3-{4-[5-(3,5-Dimethoxy-phenyl)-3-methyl-pent-2-en-4-ynyloxy]-phenyl}-2-ethoxy-propionic acid, (Z)-(S)-3-{4-[5-(3,5-Diethoxy-phenyl)-3-methyl-pent-2-en-4-ynyloxy]-phenyl}-2-ethoxy-propionic acid, (Z)-(S)-3-{4-[5-(3,5-Bis-(2,2,2-trifluoromethoxy)-phenyl)-3-methyl-pent-2-en-4-ynyloxy]-phenyl}-2-ethoxy-propionic acid, (Z)-(S)-3-{4-[5-(3,5-Bis-(2,2,2-trifluoroethoxy)-phenyl)-3-methyl-pent-2-en-4-ynyloxy]-phenyl}-2-ethoxy-propionic acid, (Z)-(S)-3-{4-[5-(1,3-Difluoro-phenyl)-pent-2-en-4-ynyloxy]-3-chloro-phenyl}-2-ethoxy-propionic acid, (Z)-(S)-3-{4-[5-(1,3-Dibromo-phenyl)-pent-2-en-4-ynyloxy]-3-chloro-phenyl}-2-ethoxy-propionic acid, (Z)-(S)-3-{4-[5-(1,3-Diiodo-phenyl)-pent-2-en-4-ynyloxy]-3-chloro-phenyl}-2-ethoxy-propionic acid, (Z)-(S)-3-{4-[5-(1,3-Bis-trifluoromethyl-phenyl)-pent-2-en-4-ynyloxy]-3-chloro-phenyl}-2-ethoxy-propionic acid, (Z)-(S)-3-{4-[5-(1,3-Dimethoxy-phenyl)-pent-2-en-4-ynyloxy]-3-chloro-phenyl}-2-ethoxy-propionic acid, (Z)-(S)-3-{4-[5-(1,3-Diethoxy-phenyl)-pent-2-en-4-ynyloxy]-3-chloro-phenyl}-2-ethoxy-propionic acid, (Z)-(S)-3-{4-[5-(1,3-Bis-(2,2,2-trifluoromethoxy)-phenyl)-pent-2-en-4-ynyloxy]-3-chloro-phenyl}-2-ethoxy-propionic acid, (Z)-(S)-3-{4-[5-(1,3-Bis-(2,2,2-trifluoroethoxy)-phenyl)-pent-2-en-4-ynyloxy]-3-chloro-phenyl}-2-ethoxy-propionic acid, (Z)-(S)-3-{4-[5-(3,5-Difluoro-phenyl)-pent-2-en-4-ynyloxy]-3-chloro-phenyl}-2-ethoxy-propionic acid, (Z)-(S)-3-{4-[5-(3,5-Dibromo-phenyl)-pent-2-en-4-ynyloxy]-3-chloro-phenyl}-2-ethoxy-propionic acid, (Z)-(S)-3-{4-[5-(3,5-Diiodo-phenyl)-pent-2-en-4-ynyloxy]-3-chloro-phenyl}-2-ethoxy-propionic acid, (Z)-(S)-3-{4-[5-(3,5-Bis-trifluoromethyl-phenyl)-pent-2-en-4-ynyloxy]-3-chloro-phenyl}-2-ethoxy-propionic acid, (Z)-(S)-3-{4-[5-(3,5-Dimethoxy-phenyl)-pent-2-en-4-ynyloxy]-3-chloro-phenyl}-2-ethoxy-propionic acid, (Z)-(S)-3-{4-[5-(3,5-Diethoxy-phenyl)-pent-2-en-4-ynyloxy]-3-chloro-phenyl}-2-ethoxy-propionic acid, (Z)-(S)-3-{4-[5-(3,5-Bis-(2,2,2-trifluoromethoxy)-phenyl)-pent-2-en-4-ynyloxy]-3-chloro-phenyl}-2-ethoxy-propionic acid, (Z)-(S)-3-{4-[5-(3,5-Bis-(2,2,2-trifluoroethoxy)-phenyl)-pent-2-en-4-ynyloxy]-3-chloro-phenyl}-2-ethoxy-propionic acid, (Z)-(S)-3-{4-[5-(1,3-Difluoro-phenyl)-3-methyl-pent-2-en-4-ynyloxy]-3-chloro-phenyl}-2-ethoxy-propionic acid, (Z)-(S)-3-{4-[5-(1,3-Dibromo-phenyl)-3-methyl-pent-2-en-4-ynyloxy]-3-chloro-phenyl}-2-ethoxy-propionic acid, (Z)-(S)-3-{4-[5-(1,3-Diiodo-phenyl)-3-methyl-pent-2-en-4-ynyloxy]-3-chloro-phenyl}-2-ethoxy-propionic acid, (Z)-(S)-3-{4-[5-(1,3-Bis-trifluoromethyl-phenyl)-3-methyl-pent-2-en-4-ynyloxy]-3-chloro-phenyl}-2-ethoxy-propionic acid, (Z)-(S)-3-{4-[5-(1,3-Dimethoxy-phenyl)-pent-2-en-4-ynyloxy]-3-chloro-phenyl}-3-methyl-2-ethoxy-propionic acid, (Z)-(S)-3-{4-[5-(1,3-Diethoxy-phenyl)-3-methyl-pent-2-en-4-ynyloxy]-3-chloro-phenyl}-2-ethoxy-propionic acid, (Z)-(S)-3-{4-[5-(1,3-Bis-(2,2,2-trifluoromethoxy)-phenyl)-3-methyl-pent-2-en-4-ynyloxy]-3-chloro-phenyl}-2-ethoxy-propionic acid, (Z)-(S)-3-{4-[5-(1,3-Bis-(2,2,2-trifluoroethoxy)-phenyl)-3-methyl-pent-2-en-4-ynyloxy]-3-chloro-phenyl}-2-ethoxy-propionic acid, (Z)-(S)-3-{4-[5-(3,5-Difluoro-phenyl)-3-methyl-pent-2-en-4-ynyloxy]-3-chloro-phenyl}-2-ethoxy-propionic acid, (Z)-(S)-3-{4-[5-(3,5-Dibromo-phenyl)-3-methyl-pent-2-en-4-ynyloxy]-3-chloro-phenyl}-2-ethoxy-propionic acid, (Z)-(S)-3-{4-[5-(3,5-Diiodo-phenyl)-3-methyl-pent-2-en-4-ynyloxy]-3-chloro-phenyl}-2-ethoxy-propionic acid, (Z)-(S)-3-{4-[5-(3,5-Bis-trifluoromethyl-phenyl)-3-methyl-pent-2-en-4-ynyloxy]-3-chloro-phenyl}-2-ethoxy-propionic acid, (Z)-(S)-3-{4-[5-(3,5-Dimethoxy-phenyl)-3-methyl-pent-2-en-4-ynyloxy]-3-chloro-phenyl}-2-ethoxy-propionic acid, (Z)-(S)-3-{4-[5-(3,5-Diethoxy-phenyl)-3-methyl-pent-2-en-4-ynyloxy]-3-chloro-phenyl}-2-ethoxy-propionic acid, (Z)-(S)-3-{4-[5-(3,5-Bis-(2,2,2-trifluoromethoxy)-phenyl)-3-methyl-pent-2-en-4-ynyloxy]-3-chloro-phenyl}-2-ethoxy-propionic acid, (Z)-(S)-3-{4-[5-(3,5-Bis-(2,2,2-trifluoroethoxy)-phenyl)-3-methyl-pent-2-en-4-ynyloxy]-3-chloro-phenyl}-2-ethoxy-propionic acid, (Z)-(S)-3-{4-[5-(1,3-Difluoro-phenyl)-pent-2-en-4-ynyloxy]-3-bromo-phenyl}-2-ethoxy-propionic acid, (Z)-(S)-3-{4-[5-(1,3-Dibromo-phenyl)-pent-2-en-4-ynyloxy]-3-bromo-phenyl}-2-ethoxy-propionic acid, (Z)-(S)-3-{4-[5-(1,3-Diiodo-phenyl)-pent-2-en-4-ynyloxy]-3-bromo-phenyl}-2-ethoxy-propionic acid,
(Z)-(S)-3-{4-[5-(1,3-Bis-trifluoromethyl-phenyl)-pent-2-en-4-ynyloxy]-3-bromo-phenyl}-2-ethoxy-propionic acid,
(Z)-(S)-3-{4-[5-(1,3-Dimethoxy-phenyl)-pent-2-en-4-ynyloxy]-3-bromo-phenyl}-2-ethoxy-propionic acid,
(Z)-(S)-3-{4-[5-(1,3-Diethoxy-phenyl)-pent-2-en-4-ynyloxy]-3-bromo-phenyl}-2-ethoxy-propionic acid,
(Z)-(S)-3-{4-[5-(1,3-Bis-(2,2,2-trifluoromethoxy)-phenyl)-pent-2-en-4-ynyloxy]-3-bromo-phenyl}-2-ethoxy-propionic acid,
(Z)-(S)-3-{4-[5-(1,3-Bis-(2,2,2-trifluoroethoxy)-phenyl)-pent-2-en-4-ynyloxy]-3-bromo-phenyl}-2-ethoxy-propionic acid,
(Z)-(S)-3-{4-[5-(3,5-Difluoro-phenyl)-pent-2-en-4-ynyloxy]-3-bromo-phenyl}-2-ethoxy-propionic acid,
(Z)-(S)-3-{4-[5-(3,5-Dibromo-phenyl)-pent-2-en-4-ynyloxy]-3-bromo-phenyl}-2-ethoxy-propionic acid,
(Z)-(S)-3-{4-[5-(3,5-Diiodo-phenyl)-pent-2-en-4-ynyloxy]-3-bromo-phenyl}-2-ethoxy-propionic acid,
(Z)-(S)-3-{4-[5-(3,5-Bis-trifluoromethyl-phenyl)-pent-2-en-4-ynyloxy]-3-bromo-phenyl}-ethoxy-propionic acid,
(Z)-(S)-3-{4-[5-(3,5-Dimethoxy-phenyl)-pent-2-en-4-ynyloxy]-3-bromo-phenyl}-2-ethoxy-propionic acid,
(Z)-(S)-3-{4-[5-(3,5-Diethoxy-phenyl)-pent-2-en-4-ynyloxy]-3-bromo-phenyl}-2-ethoxy-propionic acid,
(Z)-(S)-3-{4-[5-(3,5-Bis-(2,2,2-trifluoromethoxy)-phenyl)-pent-2-en-4-ynyloxy]-3-bromo-phenyl}-2-ethoxy-propionic acid,
(Z)-(S)-3-{4-[5-(3,5-Bis-(2,2,2-trifluoroethoxy)-phenyl)-pent-2-en-4-ynyloxy]-3-bromo-phenyl}-2-ethoxy-propionic acid,
(Z)-(S)-3-{4-[5-(1,3-Difluoro-phenyl)-3-methyl-pent-2-en-4-ynyloxy]-3-bromo-phenyl}-2-ethoxy-propionic acid,
(Z)-(S)-3-{4-[5-(1,3-Dibromo-phenyl)-3-methyl-pent-2-en-4-ynyloxy]-3-bromo-phenyl}-2-ethoxy-propionic acid,
(Z)-(S)-3-{4-[5-(1,3-Diiodo-phenyl)-3-methyl-pent-2-en-4-ynyloxy]-3-bromo-phenyl}-2-ethoxy-propionic acid,
(Z)-(S)-3-{4-[5-(1,3-Bis-trifluoromethyl-phenyl)-3-methyl-pent-2-en-4-ynyloxy]-3-bromo-phenyl}-2-ethoxy-propionic acid,
(Z)-(S)-3-{4-[5-(1,3-Dimethoxy-phenyl)-pent-2-en-4-ynyloxy]-3-bromo-phenyl}-3-methyl-2-ethoxy-propionic acid,
(Z)-(S)-3-{4-[5-(1,3-Diethoxy-phenyl)-3-methyl-pent-2-en-4-ynyloxy]-3-bromo-phenyl}-2-ethoxy-propionic acid,
(Z)-(S)-3-{4-[5-(1,3-Bis-(2,2,2-trifuoromethoxy)-phenyl)-3-methyl-pent-2-en-4-ynyloxy]-3-bromo-phenyl}-2-ethoxy-propionic acid,
(Z)-(S)-3-{4-[5-(1,3-Bis-(2,2,2-trifluoroethoxy)-phenyl)-3-methyl-pent-2-en-4-ynyloxy]-3-bromo-phenyl}-2-ethoxy-propionic acid,
(Z)-(S)-3-{4-[5-(3,5-Difluoro-phenyl)-3-methyl-pent-2-en-4-ynyloxy]-3-bromo-phenyl}-2-ethoxy-propionic acid,
(Z)-(S)-3-{4-[5-(3,5-Dibromo-phenyl)-3-methyl-pent-2-en-4-ynyloxy]-3-bromo-phenyl}-2-ethoxy-propionic acid,
(Z)-(S)-3-{4-[5-(3,5-Diiodo-phenyl)-3-methyl-pent-2-en-4-ynyloxy]-3-bromo-phenyl}-2-ethoxy-propionic acid,
(Z)-(S)-3-{4-[5-(3,5-Bis-trifluoromethyl-phenyl)-3-methyl-pent-2-en-4-ynyloxy]-3-bromo-phenyl}-2-ethoxy-propionic acid,
(Z)-(S)-3-{4-[5-(3,5-Dimethoxy-phenyl)-3-methyl-pent-2-en-4-ynyloxy]-3-bromo-phenyl}-2-ethoxy-propionic acid,
(Z)-(S)-3-{4-[5-(3,5-Diethoxy-phenyl)-3-methyl-pent-2-en-4-ynyloxy]-3-bromo-phenyl}-2-ethoxy-propionic acid,
(Z)-(S)-3-{4-[5-(3,5-Bis-(2,2,2-trifluoromethoxy)-phenyl)-3-methyl-pent-2-en-4-ynyloxy]-3-bromo-phenyl}-2-ethoxy-propionic acid,
(Z)-(S)-3-{4-[5-(3,5-Bis-(2,2,2-trifluoroethoxy)-phenyl)-3-methyl-pent-2-en-4-ynyloxy]-3-bromo-phenyl}-2-ethoxy-propionic acid,
(Z)-(S)-3-{4-[5-(1,3-Difluoro-phenyl)-pent-2-en-4-ynyloxy]-3-iodo-phenyl}-2-ethoxy-propionic acid,
(Z)-(S)-3-{4-[5-(1,3-Dibromo-phenyl)-pent-2-en-4-ynyloxy]-3-iodo-phenyl}-2-ethoxy-propionic acid,
(Z)-(S)-3-{4-[5-(1,3-Diiodo-phenyl)-pent-2-en-4-ynyloxy]-3-iodo-phenyl}-2-ethoxy-propionic acid,
(Z)-(S)-3-{4-[5-(1,3-Bis-trifluoromethyl-phenyl)-pent-2-en-4-ynyloxy]-3-iodo-phenyl}-2-ethoxy-propionic acid,
(Z)-(S)-3-{4-[5-(1,3-Dimethoxy-phenyl)-pent-2-en-4-ynyloxy]-3-iodo-phenyl}-2-ethoxy-propionic acid,
(Z)-(S)-3-{4-[5-(1,3-Diethoxy-phenyl)-pent-2-en-4-ynyloxy]-3-iodo-phenyl}-2-ethoxy-propionic acid,
(Z)-(S)-3-{4-[5-(1,3-Bis-(2,2,2-trifluoromethoxy)-phenyl)-pent-2-en-4-ynyloxy]-3-iodo-phenyl}-2-ethoxy-propionic acid,
(Z)-(S)-3-{4-[5-(1,3-Bis-(2,2,2-trifluoroethoxy)-phenyl)-pent-2-en-4-ynyloxy]-3-iodo-phenyl}-2-ethoxy-propionic acid,
(Z)-(S)-3-{4-[5-(3,5-Difluoro-phenyl)-pent-2-en-4-ynyloxy]-3-iodo-phenyl}-2-ethoxy-propionic acid,
(Z)-(S)-3-{4-[5-(3,5-Dibromo-phenyl)-pent-2-en-4-ynyloxy]-3-iodo-phenyl}-2-ethoxy-propionic acid,
(Z)-(S)-3-{4-[5-(3,5-Diiodo-phenyl)-pent-2-en-4-ynyloxy]-3-iodo-phenyl}-2-ethoxy-propionic acid,
(Z)-(S)-3-{4-[5-(3,5-Bis-trifluoromethyl-phenyl)-pent-2-en-4-ynyloxy]-3-iodo-phenyl}-2-ethoxy-propionic acid,
(Z)-(S)-3-{4-[5-(3,5-Dimethoxy-phenyl)-pent-2-en-4-ynyloxy]-3-iodo-phenyl}-2-ethoxy-propionic acid,
(Z)-(S)-3-{4-[5-(3,5-Diethoxy-phenyl)-pent-2-en-4-ynyloxy]-3-iodo-phenyl}-2-ethoxy-propionic acid,
(Z)-(S)-3-{4-[5-(3,5-Bis-(2,2,2-trifluoromethoxy)-phenyl)-pent-2-en-4-ynyloxy]-3-iodo-phenyl}-2-ethoxy-propionic acid,
(Z)-(S)-3-{4-[5-(3,5-Bis-(2,2,2-trifluoroethoxy)-phenyl)-pent-2-en-4-ynyloxy]-3-iodo-phenyl}-2-ethoxy-propionic acid,
(Z)-(S)-3-{4-[5-(1,3-Difluoro-phenyl)-3-methyl-pent-2-en-4-ynyloxy]-3-iodo-phenyl}-2-ethoxy-propionic acid,
(Z)-(S)-3-{4-[5-(1,3-Dibromo-phenyl)-3-methyl-pent-2-en-4-ynyloxy]-3-iodo-phenyl}-2-ethoxy-propionic acid,
(Z)-(S)-3-{4-[5-(1,3-Diiodo-phenyl)-3-methyl-pent-2-en-4-ynyloxy]-3-iodo-phenyl}-2-ethoxy-propionic acid, (Z)-(S)-3-{4-[5-(1,3-Bis-trifluoromethyl-phenyl)-3-methyl-pent-2-en-4-ynyloxy]-3-iodo-phenyl}-2-ethoxy-propionic acid, (Z)-(S)-3-{4-[5-(1,3-Dimethoxy-phenyl)-pent-2-en-4-ynyloxy]-3-iodo-phenyl3-methyl-2-ethoxy-propionic acid, (Z)-(S)-3-{4-[5-(1,3-Diethoxy-phenyl)-3-methyl-pent-2-en-4-ynyloxy]-3-iodo-phenyl}-2-ethoxy-propionic acid, (Z)-(S)-3-{4-[5-(1,3-Bis-(2,2,2-trifluoromethoxy)-phenyl)-3-methyl-pent-2-en-4-ynyloxy]-3-iodo-phenyl}-2-ethoxy-propionic acid, (Z)-(S)-3-{4-[5-(1,3-Bis-(2,2,2-trifluoroethoxy)-phenyl)-3-methyl-pent-2-en-4-ynyloxy]-3-iodo-phenyl}-2-ethoxy-propionic acid, (Z)-(S)-3-{4-[5-(3,5-Difluoro-phenyl)-3-methyl-pent-2-en-4-ynyloxy]-3-iodo-phenyl}-2-ethoxy-propionic acid, (Z)-(S)-3-{4-[5-(3,5-Dibromo-phenyl)-3-methyl-pent-2-en-4-ynyloxy]-3-iodo-phenyl}-2-ethoxy-propionic acid, (Z)-(S)-3-{4-[5-(3,5-Diiodo-phenyl)-3-methyl-pent-2-en-4-ynyloxy]-3-iodo-phenyl}-2-ethoxy-propionic acid, (Z)-(S)-3-{4-[5-(3,5-Bis-trifluoromethyl-phenyl)-3-methyl-pent-2-en-4-ynyloxy]-3-iodo-phenyl}-2-ethoxy-propionic acid, (Z)-(S)-3-{4-[5-(3,5-Dimethoxy-phenyl)-3-methyl-pent-2-en-4-ynyloxy]-3-iodo-phenyl}-2-ethoxy-propionic acid, (Z)-(S)-3-{4-[5-(3,5-Diethoxy-phenyl)-3-methyl-pent-2-en-4-ynyloxy]-3-iodo-phenyl}-2-ethoxy-propionic acid, (Z)-(S)-3-{4-[5-(3,5-Bis-(2,2,2-trifluoromethoxy)-phenyl)-3-methyl-pent-2-en-4-ynyloxy]-3-iodo-phenyl}-2-ethoxy-propionic acid, (Z)-(S)-3-{4-[5-(3,5-Bis-(2,2,2-trifluoroethoxy)-phenyl)-3-methyl-pent-2-en-4-ynyloxy]-3-iodo-phenyl}-2-ethoxy-propionic acid;

or a salt thereof with a pharmaceutically acceptable acid or base, or any optical isomer or mixture of optical isomers, including a racemic mixture, or any tautomeric forms.

In the above structural formulas and throughout the present specification, the following terms have the indicated meaning:

The term "$C_{1-12}$-alkyl" as used herein, alone or in combination is intended to include those alkyl groups of the designated length in either a linear or branched or cyclic configuration represents e.g. cyclopropyl, cyclobutyl, cyclopentyl, cyclohexyl, cycloheptyl and cyclooctyl and the like. Typical $C_{1-12}$-alkyl groups include, but are not limited to, methyl, ethyl, n-propyl, iso-propyl, butyl, iso-butyl, sec-butyl, tert-butyl, pentyl, iso-pentyl, hexyl, iso-hexyl, cyclopropyl, cyclobutyl, cyclopentyl, cyclohexyl, cycloheptyl and cyclooctyl and the like, especially preferred is methyl and ethyl.

The term "$C_{2-12}$-alkenyl" as used herein, represents an olefinically unsaturated branched or straight group having from 2 to the specified number of carbon atoms and at least one double bond. Examples of such groups include, but are not limited to, vinyl, 1-propenyl, 2-propenyl, allyl, iso-proppenyl, 1,3-butadienyl, 1-butenyl, hexenyl, pentenyl and the like, especially preferred is vinyl and 1-propenyl.

The term "$C_{2-12}$-alkynyl" as used herein, represent an unsaturated branched or straight group having from 2 to the specified number of carbon atoms and at least one triple bond. Examples of such groups include, but are not limited to, 1-propynyl, 2-propynyl, 1-butynyl, 2-butynyl, 1-pentynyl, 2-pentynyl and the like especially preferred is 1-propynyl.

The term "$C_{4-12}$-alkenynyl" as used herein, represent an unsaturated branched or straight hydrocarbon group having from 4 to the specified number of carbon atoms and both at least one double bond and at least one triple bond. Examples of such groups include, but are not limited to, 1-penten-4-yne, 3-penten-1-yne, 1,3-hexadiene-5-yne and the like, especially preferred is 1-pentene-4-yne.

The term "$C_{1-6}$-alkoxy" as used herein, alone or in combination is intended to include those $C_{1-6}$-alkyl groups of the designated length in either a linear or branched or cyclic configuration linked thorough an ether oxygen having its free valence bond from the ether oxygen. Examples of linear alkoxy groups are methoxy, ethoxy, propoxy, butoxy, pentoxy, hexoxy and the like especially preferred is methoxy and ethoxy. Examples of branched alkoxy are isopropoxy, sec-butoxy, tert-butoxy, isopentoxy, isohexoxy and the like especially preferred is isopropoxy. Examples of cyclic alkoxy are cyclopropyloxy, cyclobutyloxy, cyclopentyloxy, cyclohexyloxy and the like, especially preferred is cyclopropoxy.

The term "$C_{1-6}$-alkylthio" as used herein, alone or in combination, refers to a straight or branched or cyclic monovalent substituent comprising a $C_{1-6}$-alkyl group linked through a divalent sulfur atom having its free valence bond from the sulfur atom and having 1 to 6 carbon atoms e.g. methylthio, ethylthio, propylthio, butylthio, pentylthio and the like.

Examples of cyclic alkylthio are cyclopropylthio, cyclobutylthio, cyclopentylthio, cyclohexylthio and the like.

The term "$C_{1-6}$-alkylamino" as used herein, alone or in combination, refers to a straight or branched or cyclic monovalent substituent comprising a $C_{1-6}$-alkyl group linked through amino having a free valence bond from the nitrogen atom e.g. methylamino, ethylamino, propylamino, butylamino, pentylamino and the like. Examples of cyclic alkylamino are cyclopropylamino, cyclobutylamino, cyclopentylamino, cyclohexylamino and the like.

The term "$C_{1-6}$-alkoxy$C_{1-6}$-alkyl" as used herein, alone or in combination, refers to a $C_{1-6}$-alkyl as defined herein whereto is attached a $C_{1-6}$-alkoxy as defined herein, e.g. methoxymethyl, ethoxymethyl, methoxyethyl, ethoxyethyl and the like.

The term "aryl" is intended to include aromatic rings, such as carbocyclic aromatic rings selected from the group consisting of phenyl, naphthyl, (1-naphthyl or 2-naphthyl) and the like optionally substituted with halogen, amino, hydroxy, $C_{1-6}$-alkyl, $C_{1-6}$-alkoxy, $C_{1-6}$-alkylester or carboxy and the like, especially preferred is phenyl and naphtyl optionally substituted with halogen.

The term "arylene" is intended to include divalent aromatic rings, such as carbocyclic aromatic rings selected from the group consisting of phenylene, naphthylene and the like optionally substituted with halogen, amino, hydroxy, $C_{1-6}$-alkyl, $C_{1-6}$-alkoxy, $C_{1-6}$-alkylester or carboxy and the like, especially preferred is phenylene.

The term "halogen" means fluorine, chlorine, bromine or iodine especially preferred is chlorine.

The term "perhalomethyl" means trifluoromethyl, trichloromethyl, tribromomethyl or triiodomethyl, especially preferred is trifluoromethyl.

The term "$C_{1-6}$-dialkylamino" as used herein refers to an amino group wherein the two hydrogen atoms independently are substituted with a straight or branched, saturated hydrocarbon chain having the indicated number of carbon atoms; such as dimethylamino, N-ethyl-N-methylamino, diethylamino, dipropylamino, N-(n-butyl)-N-methylamino, di(n-pentyl)amino and the like.

The term "acyl" as used herein refers to a monovalent substituent comprising a $C_{1-6}$-alkyl group linked through a carbonyl group; such as e.g. acetyl, propionyl, butyryl, isobutyryl, pivaloyl, valeryl and the like.

The term "heteroaryl" as used herein, alone or in combination, refers to a monovalent substituent comprising a 5–6 membered monocyclic aromatic system or a 9–10 membered bicyclic aromatic system containing one or more heteroatoms selected from nitrogen, oxygen and sulfur, e.g. furan, thiophene, pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine and purine and the like especially preferred is furan, pyrrole, pyridine, indole and benzofuran.

The term "heteroarylene" as used herein, alone or in combination, refers to a divalent group comprising a 5–6 membered monocyclic aromatic system or a 9–10 membered bicyclic aromatic system containing one or more heteroatoms selected from nitrogen, oxygen and sulfur, e.g. furan, thiophene, pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine and purine and the like, especially preferred is furan, pyrrole, pyridine, indole and benzofuran.

The term "heteroaryloxy" as used herein, alone or in combination, refers to a heteroaryl as defined herein linked to an oxygen atom having its free valence bond from the oxygen atom e.g. pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine and purine linked to oxygen, and the like.

The term "aralkyl" as used herein refers to a straight or branched saturated carbon chain containing from 1 to 6 carbons substituted with an aromatic carbohydride; such as benzyl, phenethyl, 3-phenylpropyl, 1-naphthylmethyl, 2-(1-naphthyl)ethyl and the like, especially preferred is benzyl.

The term "aryloxy" as used herein refers to phenoxy, 1-naphthyloxy, 2-naphthyloxy and the like especially preferred is phenoxy. The term "aralkoxy" as used herein refers to a $C_{1-6}$-alkoxy group substituted with an aromatic carbohydride, such as benzyloxy, phenethoxy, 3-phenylpropoxy, 1-naphthylmethoxy, 2-(1-naphtyl)ethoxy and the like, especially preferred is benzyloxy.

The term "heteroaralkyl" as used herein refers to a straight or branched saturated carbon chain containing from 1 to 6 carbons substituted with a heteroaryl group; such as (2-furyl)methyl, (3-furyl)methyl, (2-thienyl)methyl, (3-thienyl)methyl, (2-pyridyl)methyl, 1-methyl-1-(2-pyrimidyl)ethyl and the like.

The term "heteroaralkoxy" as used herein refers to a heteroarylalkyl as defined herein linked to an oxygen atom having its free valence bond from the oxygen atom, e.g. (2-furyl)methyl, (3-furyl)methyl, (2-thienyl)methyl, (3-thienyl)methyl, (2-pyridyl)methyl, 1-methyl-1-(2-pyrimidyl)ethyl linked to oxygen, and the like.

The term "arylthio" as used herein, alone or in combination, refers to an aryl group linked through a divalent sulfur atom having its free valence bond from the sulfur atom, the aryl group optionally being mono- or polysubstituted with $C_{1-6}$-alkyl, halogen, hydroxy or $C_{1-6}$-alkoxy; e.g. phenylthio, (4-methylphenyl)-thio, (2-chloro-phenyl)thio and the like.

As used herein, the phrase "heterocyclyl" means a monovalent saturated or unsaturated non aromatic group being monocyclic and containing one or more, such as from one to four carbon atom(s), and from one to four N, O or S atom(s) or a combination thereof. The phrase "heterocyclyl" includes, but is not limited to, 5-membered heterocycles having one hetero atom (e.g. pyrrolidine, pyrroline and the like); 5-membered heterocycles having two heteroatoms in 1,2 or 1,3 positions (e.g. pyrazoline, pyrazolidine, 1,2-oxathiolane, imidazolidine, imidazoline, 4-oxazolone and the like); 5-membered heterocycles having three heteroatoms (e.g. tetrahydrofurazan and the like); 5-membered heterocycles having four heteroatoms; 6-membered heterocycles with one heteroatom (e.g. piperidine and the like); 6-membered heterocycles with two heteroatoms (e.g. piperazine, morpholine and the like); 6-membered heterocycles with three heteroatoms; and 6-membered heterocycles with four heteroatoms, and the like.

As used herein, the phrase "a divalent heterocyclic group" means a divalent saturated or unsaturated system being monocyclic and containing one or more, such as from one to four carbon atom(s), and one to four N, O or S atom(s) or a combination thereof. The phrase a divalent heterocyclic group includes, but is not limited to, 5-membered heterocycles having one hetero atom (e.g. pyrrolidine, pyrroline and the like); 5-membered heterocycles having two heteroatoms in 1,2 or 1,3 positions (e.g. pyrazoline, pyrazolidine, 1,2-oxathiolane, imidazolidine, imidazoline, 4-oxazolone and the like); 5-membered heterocycles having three heteroatoms (e.g. tetrahydrofurazan and the like); 5-membered heterocycles having four heteroatoms; 6-membered heterocycles with one heteroatom (e.g. piperidine and the like); 6-membered heterocycles with two heteroatoms (e.g. piperazine, morpholine and the like); 6-membered heterocycles with three heteroatoms; and 6-membered heterocycles with four heteroatoms, and the like.

As used herein the term "treatment" includes treatment, prevention and management of such condition.

Certain of the above defined terms may occur more than once in the above formula (I), and upon such occurrence each term shall be defined independently of the other.

The present invention also encompasses pharmaceutically acceptable salts of the present compounds. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

The pharmaceutically acceptable salts are prepared by reacting the compound of formula I with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixture of solvents may be used. Organic bases like lysine, arginine, diethanolamine, choline, guandine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, enzymatic resolution, resolving the diastereomeric salts formed with chiral acids such as mandelic acid, camphorsulfonic acid, tartaric acid, lactic acid, and the like wherever applicable or chiral bases such as brucine, (R)- or (S)-phenylethylamine, cinchona alkaloids and their derivatives and the like. Commonly used methods are compiled by Jaques et al in "Enantiomers, Racemates and Resolution" (Wiley Interscience, 1981). More specifically the compound of formula I may be converted to a 1:1 mixture of diastereomeric amides by treating with chiral amines, aminoacids, aminoalcohols derived from aminoacids; conventional reaction conditions may be employed to convert acid into an amide; the dia-stereomers may be separated either by fractional crystallization or chromatography and the stereoisomers of compound of formula I may be prepared by hydrolysing the pure diastereomeric amide.

Various polymorphs of compound of general formula I forming part of this invention may be prepared by crystallization of compound of formula I under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe nmr spectroscopy, ir spectroscopy, differential scanning calorimetry, powder X-ray diffraction or such other techniques.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

Furthermore, the present compounds of formula I can be utilised in the treatment and/or prevention of conditions mediated by nuclear receptors, in particular the Peroxisome Proliferator-Activated Receptors (PPAR).

In a further aspect, the present invention relates to a method of treating and/or preventing Type I or Type II diabetes.

In a still further aspect, the present invention relates to the use of one or more compounds of the general formula I or pharmaceutically acceptable salts thereof for the preparation of a medicament for the treatment and/or prevention of Type I or Type II diabetes.

In a still further aspect, the present compounds are useful for the treatment and/or prevention of IGT.

In a still further aspect, the present compounds are useful for the treatment and/or prevention of Type 2 diabetes.

In a still further aspect, the present compounds are useful for the delaying or prevention of the progression from IGT to Type 2 diabetes.

In a still further aspect, the present compounds are useful for the delaying or prevention of the progression from non-insulin requiring Type 2 diabetes to insulin requiring Type 2 diabetes.

In another aspect, the present compounds reduce blood glucose and triglyceride levels and are accordingly useful for the treatment and/or prevention of ailments and disorders such as diabetes and/or obesity.

In still another aspect, the present compounds are useful for the treatment and/or prophylaxis of insulin resistance (Type 2 diabetes), impaired glucose tolerance, dyslipidemia, disorders related to Syndrome X such as hypertension, obesity, insulin resistance, hyperglycaemia, atherosclerosis, hyperlipidemia, coronary artery disease, myocardial ischemia and other cardiovascular disorders.

In still another aspect, the present compounds are effective in decreasing apoptosis in mammalian cells such as beta cells of Islets of Langerhans.

In still another aspect, the present compounds are useful for the treatment of certain renal diseases including glomerulonephritis, glomerulosclerosis, nephrotic syndrome, hypertensive nephrosclerosis.

In still another aspect, the present compounds may also be useful for improving cognitive functions in dementia, treating diabetic complications, psoriasis, polycystic ovarian syndrome (PCOS) and prevention and treatment of bone loss, e.g. osteoporosis.

The invention also relates to pharmaceutical compositions comprising, as an active ingredient, at least one compound of the formula I or any optical or geometric isomer or tautomeric form thereof including mixtures of these or a pharmaceutically acceptable salt thereof together with one or more pharmaceutically acceptable carriers or diluents.

Furthermore, the invention relates to the use of compounds of the general formula I or their tautomeric forms, their stereoisomers, their polymorphs, their pharmaceutically acceptable salts or pharmaceutically acceptable solvates thereof for the preparation of a pharmaceutical composition for the treatment and/or prevention of conditions mediated by nuclear receptors, in particular the Peroxisome Proliferator-Activated Receptors (PPAR) such as the conditions mentioned above.

The present invention also relates to a process for the preparation of the above said novel compounds, their derivatives, their analogs, their tautomeric forms, their stereoisomers, their polymorphs, their pharmaceutically acceptable salts or pharmaceutically acceptable solvates.

The method comprises:

a)

Reacting a compound of formula II (prepared for example according to methods described in: *Chem. Commun.*, 718–719, 1967; *Org. Syntheses*, Coll. Vol 3, 731–733, 1955; *Org. Syntheses*, Coll. Vol IV, 801–803, 1963.

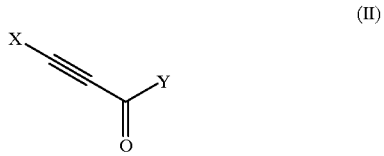
(II)

wherein X and Y are defined as above, through a Wittig-like process with for example $(EtO)_2PO(CHZ)(CH_2)_tCOOR_6$ (wherein $R_6$ is an alkyl group), in the presence of a base such as sodium hydride, EtONa and the like to give a compound of formula III

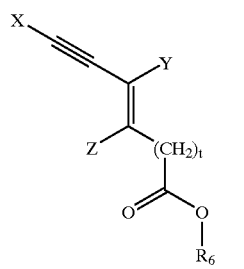

wherein X, Y, Z and $R_6$ are defined as above, and wherein t is 0–2, and b)

reducing a compound of formula II, wherein X, Y, Z, $R_6$ and t are defined as above with a suitable reagent such as diisobutylaluminium hydride, to give a compound of formula IV

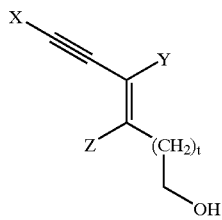

wherein X, Y, Z and t are defined as above, and c)

reacting a compound of formula IV, wherein X, Y, Z and t are defined as above, with a compound of formula V

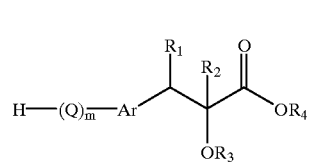
(V)

wherein Q, Ar, $R_1$, $R_2$, $R_3$, $R_4$ and m are defined as above, except that m is not 0, under Mitsunobu conditions, using a reagent such as triphenylphosphine/diethylazodicarboxylate and the like to obtain a compound of formula I, wherein X, Y, Z, Q, Ar, $R_1$, $R_2$, $R_3$, $R_4$, n and m are defined as above, except that $R_4$ is not H, n and m are not 0, or d)

by converting the —OH functionality in a compound of formula IV, wherein X, Y, Z and t are defined as above, to an appropriate leaving group (L) such as p-toluenesulfonate, methanesulfonate, halogen (for example by methods according to: Houben-Weyl, Methoden der organischen Chemie, Alkohole III, 6/1b, Thieme-Verlag 1984, 4th Ed., pp. 927–939; Comprehensive Organic Transformations. A guide to functional group preparations, VCH Publishers 1989, 1$^{st}$ Ed., pp. 353–363 and *J. Org. Chem.*, Vol. 36 (20), 3044–3045, 1971), triflate and the like, to give a compound of formula VI

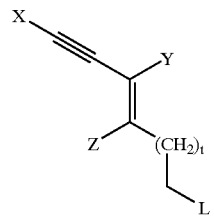

wherein L, X, Y, Z and t are defined as above, or e)

reacting a compound of formula VI wherein L is a leaving group such as p-toluenesulfonate, methanesulfonate, halogen, triflate and the like and wherein X, Y, Z and t are defined as above with a compound of formula V

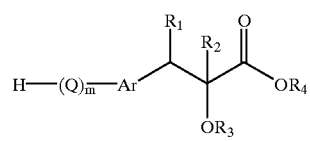
(V)

wherein Q, Ar, $R_1$, $R_2$, $R_3$, $R_4$ and m are defined as above except that m is not 0, to give a compound of formula I wherein X, Y, Z, Q, Ar, $R_1$, $R_2$, $R_3$, $R_4$, n and m are defined as above except that $R_4$ is not H, n and m are not 0, or f)
by chemical or enzymatic saponification of a compound of formula I

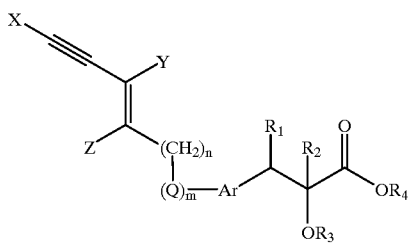

(I)

wherein X, Y, Z, Q, Ar, $R_1$, $R_2$, $R_3$, $R_4$, n and m are defined as above except that $R_4$ is not H, to obtain a compound of formula I, wherein X, Y, Z, Q, Ar, $R_1$, $R_2$, $R_3$, $R_4$, n and m are defined as above except that $R_4$ is H.

Alternative methods for the synthesis of a compound of formula I, a compound of formula III, a compound of formula IV and a compound of formula VI are:
g)
reacting a compound of formula VII

(VII)

wherein X is defined as above with a compound of formula VIII

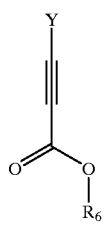

(VIII)

under Pd catalysed cross-coupling conditions (for example as described in: Tetrahedron Lett, 39 (36), 6445–6448, 1998), to give a compound of formula III wherein X, Y and $R_6$ are defined as above, and wherein t is 0, and Z is hydrogen.
h)
reacting a compound of formula VII with a compound of formula IX

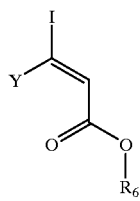

(IX)

according to a method analogous to that described in Tetrahedron Lett, 39 (37), 6719–6720, 1998, to give a compound of formula III wherein X, Y, Z and $R_6$ are defined as above, and wherein t is 0.

i)
Trans-cis or cis-trans isomerization of compounds I, III, IV, and VI (Arai et al., Chem. Rev., 93, pp 23–39, 1993; J. March, Advanced Organic Chemistry, $4^{th}$ Ed., J. Wiley & Sons, New York 1992, pp. 218, 245, 745).

PHARMACOLOGICAL METHODS
In Vitro PPAR Alpha and PPAR Gamma Activation Activity

Principle

The PPAR gene transcription activation assays were based on transient transfection into human HEK293 cells of two plasmids encoding a chimeric test protein and a reporter protein respectively. The chimeric test protein was a fusion of the DNA binding domain (DBD) from the yeast GAL4 transcription factor to the ligand binding domain (LBD) of the human PPAR proteins. The PPAR LBD harbored in addition to the ligand binding pocket also the native activation domain (activating function 2=AF2) allowing the fusion protein to function as a PPAR ligand dependent transcription factor. The GAL4 DBD will force the fusion protein to bind only to Gal4 enhancers (of which none existed in HEK293 cells). The reporter plasmid contained a Gal4 enhancer driving the expression of the firefly luciferase protein. After transfection, HEK293 cells expressed the GAL4-DBD-PPAR-LBD fusion protein. The fusion protein will in turn bind to the Gal4 enhancer controlling the luciferase expression, and do nothing in the absence of ligand. Upon addition to the cells of a PPAR ligand, luciferase protein will be produced in amounts corresponding to the activation of the PPAR protein. The amount of luciferase protein is measured by light emission after addition of the appropriate substrate.

Methods
In Vitro Transactivation Assays.

Cell culture and transfection: HEK293 cells were grown in DMEM+10% FCS. Cells were seeded in 96-well plates the day before transfection to give a confluency of 50–80% at transfection. A total of 0,8 µg DNA containing 0,64 µg pM1α/γLBD, 0,1 µg pCMVβGal, 0,08 µg pGL2Gal4DBD and 0,02 µg pADVANTAGE was transfected per well using FuGene transfection reagent according to the manufacturers instructions (Roche). Cells were allowed to express protein for 48 h followed by addition of compound.

Plasmids: Human PPAR α and γ was obtained by PCR amplification using cDNA synthesized by reverse transcription of mRNA from liver and adipose tissue respectively. Amplified cDNAs were cloned into pCR2.1 and sequenced. The ligand binding domain (LBD) of each PPAR isoform was generated by PCR (PPARα: aa 167-C-terminus; PPARγ: aa 165-C-terminus) and fused to the DNA binding domain (DBD) of the yeast transcription factor GAL4 by subcloning fragments in frame into the vector pM1 generating the plasmids pM1αLBD and pM1γLBD. Ensuing fusions were verified by sequencing. The reporter was constructed by inserting an oligonucleotide encoding five repeats of the GAL4 recognition sequence (5×CGGAGTACTGTCCTCCG(AG)) into the vector pGL2 promotor (Promega) generating the plasmid pGL2(GAL4)$_5$. pCMVβGal was purchased from Clontech and pADVANTAGE was purchased from Promega.

Luciferase assay: Medium including test compound was aspirated and 100 µl PBS incl. 1 mM Mg++ and Ca++ was added to each well. The luciferase assay was performed using the LucLite kit according to the manufacturers instructions (Packard Instruments). Light emission was quantified by counting SPC mode on a Packard Instruments top-counter. To measure β-galactosidase activity 25 µl supernatant from each transfection lysate was transferred to a new microplate. β-galactosidase assays were performed in the microwell plates using a kit from Promega and read in a microplate reader. The β-galactosidase data were used to normalize (transfection efficiency, cell growth etc.) the luciferase data.

Compounds: All compounds were dissolved in DMSO and diluted 1:1000 upon addition to the cells. Compounds were tested in quadruple in five concentrations ranging form 0.01 to 30 µM. Cells were treated with compound for 24 h followed by luciferase assay. Each compound was tested in three separate experiments. $EC_{50}$ values were calculated via non-linear regression using GraphPad PRISM 3.02 (GraphPad Software, San Diego, Calif.). The results were expressed as means.

TABLE 1

In vitro PPAR alpha and PPAR gamma activation of examples according to the present invention.

| | In vitro activation | | | |
|---|---|---|---|---|
| | PPAR α | | PPAR γ | |
| Example no | $EC_{50}$, µM | % max[a] | $EC_{50}$, µM | % max[b] |
| 6 | 0.20 | 217 | 0.7 | 108 |
| 8 | 0.06 | 139 | 0.31 | 126 |
| 12 | 0.05 | 195 | 0.34 | 105 |
| 18 | 0.16 | 181 | 2.67 | 91 |
| 20 | 0.04 | 154 | 1.42 | 112 |

Compounds were tested in at least three separate experiments in five concentrations ranging from 0.01 to 30 µM. $EC_{50}$'s were not calculated for compounds producing transactivation lower than 25% at 30 µM. [a]Fold activation relative to maximum activation obtained with Wy14643 (approx. 20 fold corresponded to 100%) and with [b]rosiglitazone (approx. 120 fold corresponded to 100%).

PHARMACEUTICAL COMPOSITIONS

In another aspect, the present invention includes within its scope pharmaceutical compositions comprising, as an active ingredient, at least one of the compounds of the general formula I or a pharmaceutically acceptable salt thereof together with a pharmaceutically acceptable carrier or diluent.

The present compounds may also be administered in combination with one or more further pharmacologically active substances eg., selected from antiobesity agents, antidiabetics, antihypertensive agents, agents for the treatment and/or prevention of complications resulting from or associated with diabetes and agents for the treatment and/or prevention of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MG4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators or TR β agonists.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

Suitable antidiabetics comprise insulin, GLP-1 (glucagon like peptide-1) derivatives such as those disclosed in WO 98/08871 to Novo Nordisk A/S, which is incorporated herein by reference as well as orally active hypoglycaemic agents.

The orally active hypoglycaemic agents preferably comprise sulphonylureas, biguanides, meglitinides, glucosidase inhibitors, glucagon antagonists such as those disclosed in WO 99/01423 to Novo Nordisk A/S and Agouron Pharmaceuticals, Inc., GLP-1 agonists, potassium channel openers such as those disclosed in WO 97/26265 and WO 99/03861 to Novo Nordisk A/S which are incorporated herein by reference, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents as HMG CoA inhibitors (statins), compounds lowering food intake, RXR agonists and agents acting on the ATP-dependent potassium channel of the β-cells.

In one embodiment of the invention the present compounds are administered in combination with insulin.

In a further embodiment the present compounds are administered in combination with a sulphonylurea eg. tolbutamide, glibenclamide, glipizide or glicazide.

In another embodiment the present compounds are administered in combination with a bi-guanide eg. metformin.

In yet another embodiment the present compounds are administered in combination with a meglitinide eg. repaglinide or senaglinide.

In a further embodiment the present compounds are administered in combination with an α-glucosidase inhibitor eg. miglitol or acarbose.

In another embodiment the present compounds are administered in combination with an agent acting on the ATP-dependent potassium channel of the β-cells eg. tolbutamide, glibenclamide, glipizide, glicazide or repaglinide.

Furthermore, the present compounds may be administered in combination with nateglinide.

In still another embodiment the present compounds are administered in combination with an antihyperlipidemic agent or antilipidemic agent eg. cholestyramine, colestipol, clofibrate, gemfibrozil, lovastatin, pravastatin, simvastatin, probucol or dextrothyroxine.

In a further embodiment the present compounds are administered in combination with more than one of the above-mentioned compounds eg. in combination with a sulphonylurea and metformin, a sulphonylurea and acarbose, repaglinide and metformin, insulin and a sulphonylurea, insulin and metformin, insulin, insulin and lovastatin, etc.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

It should be understood that any suitable combination of the compounds according to the invention with one or more of the above-mentioned compounds and optionally one or more further pharmacologically active substances are considered to be within the scope of the present invention.

Pharmaceutical compositions containing a compound of the present invention may be prepared by conventional techniques, e.g. as described in Remington: The Science and Practice of Pharmacy, 19$^{th}$ Ed., 1995. The compositions may appear in conventional forms, for example capsules, tablets, aerosols, solutions, suspensions or topical applications.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrer, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, peanut oil, olive oil, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The route of administration may be any route, which effectively transports the active compound to the appropriate or desired site of action, such as oral, nasal, pulmonary, transdermal or parenteral e.g. rectal, depot, subcutaneous, intravenous, intraurethral, intramuscular, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:

| Core: | |
|---|---|
| Active compound (as free compound or salt thereof) | 5 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

The compounds of the invention may be administered to a mammal, especially a human in need of such treatment, prevention, elimination, alleviation or amelioration of diseases related to the regulation of blood sugar.

Such mammals include also animals, both domestic animals, e.g. household pets, and nondomestic animals such as wildlife.

The compounds of the invention are effective over a wide dosage range. For example, in the treatment of adult humans, dosages from about 0.05 to about 100 mg, preferably from about 0.1 to about 100 mg, per day may be used.

A most preferable dosage is about 0.1 mg to about 70 mg per day. In choosing a regimen for patients it may frequently be necessary to begin with a dosage of from about 2 to about 70 mg per day and when the condition is under control to reduce the dosage as low as from about 0.1 to about 10 mg per day. The exact dosage will depend upon the mode of administration, on the therapy desired, form in which administered, the subject to be treated and the body weight of the subject to be treated, and the preference and experience of the physician or veterinarian in charge.

Generally, the compounds of the present invention are dispensed in unit dosage form comprising from about 0.1 to about 100 mg of active ingredient together with a pharmaceutically acceptable carrier per unit dosage.

Usually, dosage forms suitable for oral, nasal, pulmonary or transdermal administration comprise from about 0.001 mg to about 100 mg, preferably from about 0.01 mg to about 50 mg of the compounds of formula I admixed with a pharmaceutically acceptable carrier or diluent.

Any novel feature or combination of features described herein is considered essential to this invention.

EXAMPLES

The process for preparing compounds of formula I, and preparations containing them, is further illustrated in the following examples, which however, are not to be construed as limiting.

The structures of the compounds are confirmed by either elemental analysis (MA) nuclear magnetic resonance (NMR), mass spectrometry (MS) or optical rotation. NMR shifts (δ) are given in parts per million (ppm) and only selected peaks are given. mp is melting point and is given in ° C. Column chromatography was carried out using the technique described by W. C. Still et al, J. Org. Chem. 1978, 43, 2923–2925 on Merck silica gel 60 (Art 9385). The optical rotation was measured on a Advanced Laser Polarimeter.

Compounds used as starting materials are either known compounds or compounds which can readily be prepared by methods known per se.

| Abbreviations: | |
|---|---|
| THF: | tetrahydrofuran |
| DMSO: | dimethylsulfoxide |
| MTBE: | tertbutylmethylether |
| CDCl$_3$: | deuterated chloroform |
| DMF: | N,N-dimethylformamide |
| min: | minutes |
| h: | hours |

Example 1

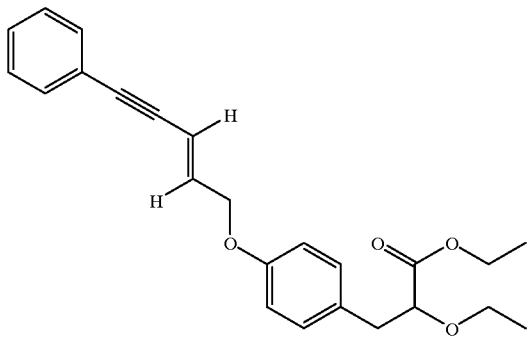

(E)-(S)-2-Ethoxy-3-[4-(5-phenyl-pent-2-en-4-ynyloxy)-phenyl]-propionic Acid Ethyl Ester Method 1 a)

A solution of triethyl phosphonoacetate (25.8 g, 115 mmol) in toluene (100 mL) was added at 0° C. to a stirred suspension of sodium hydride (60% in oil, 3.12 g, 130 mmol) in toluene (300 mL) and the mixture stirred at 0° C. for 30 min. A solution of 3-phenylpropargyl aldehyde (*Org. Syntheses*, Coll. Vol 3, 731–733, 1955) (10.0 g, 77 mmol) in dry THF (15 mL) was added, the mixture slowly warmed to room temperature, and stirring continued for 16 h. The reaction mixture was quenched with ethanol (25 mL) and water (300 mL), the organic phase separated, and the aqueous phase extracted with dichloromethane (300 mL). The combined organic phases were concentrated in vacuo, and submitted to flash column chromatography, petroleum ether/toluene (1:1) graduated to petroleum ether/toluene (1:9) as eluent, to give (1.21 g, 8%) of (E)-5-phenyl-pent-2-en-4-ynoic acid ethyl ester.

$^1$H NMR (CDCl$_3$, 300 MHz) δ: 1.30 (t, 3H), 4.25 (q, 2H), 6.30 (d, 1H, J$_{trans}$=15 Hz), 6.98 (d, 1H, J$_{trans}$=15 Hz), 7.30–7.40 (m, 3H), 7.45–7.50 (m, 2H).

b)

Diisobutylaluminium hydride (1.0 M solution in toluene, 42 mL, 42 mmol) was added, under a nitrogen atmosphere at −70° C., to a stirred solution of (E)-5-phenyl-pent-2-en-4-ynoic acid ethyl ester (1.2 g, 5.99 mmol) in dry THF (105 mL). After stirring for 1.5 h, the reaction mixture was quenched with methanol (5 mL) followed by saturated aqueous Rochelle's salt (90 mL) and 1N sodium hydroxide (40 mL). The organic phase was separated, and the aqueous phase extracted with ethyl acetate (250 mL, 2×). The combined organic phases were dried (MgSO$_4$), filtered and concentrated in vacuo to give 948 mg (100%) of (E)-5-phenyl-pent-2-en-4-yn-1-ol. $^1$H NMR (CDCl$_3$, 300 MHz) δ: 2.20 (bs, 1H), 4.25 (d, 2H), 5.95 (dt, 1H, J$_{trans}$=15 Hz), 6.35 (dt, 1H, J$_{trans}$=15 Hz), 7.23–7.35 (m, 3H), 7.35–7.48 (m, 2H).

c)

(E)-5-Phenyl-pent-2-en-4-yn-1-ol (328 mg, 2.07 mmol), tributylphosphine (606 mg, 3.0 mmol) and (S)-2-ethoxy-3-(4-hydroxy-phenyl)-propionic acid ethyl ester (*Tetrahedron Letters*, Vol. 35, No. 19, 3139–3142, 1994) (495 mg, 2.07 mmol) were successively dissolved in dry benzene (30 mL) under a nitrogen atmosphere and the solution cooled to 0° C. Solid 1,1'-(azodicarbonyl) dipiperidine (756 mg, 3.0 mmol) was added, the mixture stirred for 10 min., then warmed to room temperature and stirred for 16 h. The reaction mixture was filtered and the filtrate concentrated in vacuo. The product was purified by flash column chromatography eluting with toluene graduated to toluene/ethyl acetate (19:1) to give 450 mg (57%) of the title compound.

$^1$H NMR (CDCl$_3$, 300 MHz) δ: 1.18 (t, 3H), 1.25 (t, 3H), 2.95 (d, 2H), 3.30–3.42 (m, 1H), 3.55–3.67 (m, 1H), 3.98 (t, 1H), 4.15 (q, 2H), 4.60 (d, 2H), 6.15 (dt, 1H, J$_{trans}$=15 Hz), 6.48 (dt, 1H, J$_{trans}$=15 Hz), 6.85 (d, 2H), 7.15 (d, 2H), 7.28–7.35 (m, 3H), 7.40–7.46 (m, 2H).

$[α]_{670}^{25}$=30°±4°.

Method 2 a)

To a mixture of (E)-5-phenyl-pent-2-en-4-yn-1-ol (Method 1b) (4.9 g, 31.0 mmol) and triethylamine (3.8 g, 38.0 mmol) in dry dichloromethane (200 mL) was added methanesulfonyl chloride (3.8 g, 33 mmol) dropwise. Stirring was continued at room temperature overnight. The reaction mixture was concentrated in vacuo and the residue washed with heptane/dichloromethane (×2) to give 4.5 g (82%) crude (E)-(5-chloro-pent-3-en-1-ynyl-benzene.

$^1$H NMR (CDCl$_3$, 300 MHz) δ: 4.13 (d, 2H)), 6.0 (d, 1H, J$_{trans}$=15 Hz), 6.29 (dt, 1H, J$_{trans}$=15 Hz), 7.28–7.35 (m, 3H), 7.40–7.48 (m, 2H).

b)

To a solution of (E)-(5-chloro-pent-3-en-1-ynyl)-benzene (177 mg, 1.0 mmol) and (S)-2-ethoxy-3-(4-hydroxy-phenyl)-propionic acid ethyl ester (238 mg, 1.0 mmol) in acetone (15 mL) was added potassium carbonate (700 mg, 5.0 mmol) and potassium iodide (17 mg, 0.1 mmol). The mixture was heated to reflux over night with stirring. Water was added and the product extracted with tert-butyl methyl ether (×3) The combined organic phases were dried (MgSO$_4$), filtered and concentrated in vacuo, to give the title compound as a crude product.

Method 3 a)

A solution of (E)-5-phenyl-pent-2-en-4-yn-1-ol (Method 1b) (980 mg, 6.2 mmol) in dry toluene (20 mL) was cooled on ice and phosphorus tribromide (0.59 mL, 6.2 mmol) added slowly. After 16 h at 5° C. the mixture was diluted with ethyl acetate and washed with water (×3). The organic phase was concentrated in vacuo and the residue extracted with heptane (×3). The combined heptane phases were concentrated in vacuo to give 900 mg of crude (E)-(5-bromo-pent-3-en-1-ynyl)-benzene. (According to NMR the product contained ~5% of the (Z)-isomer).

$^1$H NMR (CDCl$_3$, 300 MHz) δ: 4.02 (d, 1H), 4.25 (d, 0.05 H), 5.82 (d, 0.05 H, J$_{cis}$=8 Hz), 5.95 (d, 1H, J$_{trans}$=16 Hz), 6.18 (dt, 0.05 H, J$_{cis}$=8 Hz), 6.35 (dt, 1H, J$_{trans}$=16 Hz), 7.26–7.35 (m, 3H), 7.35–7.48 (m, 2H).

Example 2

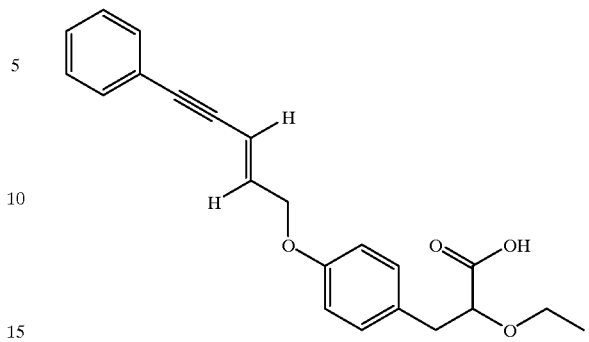

(E)-(S)-2-Ethoxy-3-[4-(5-phenyl-pent-2-en-4-ynyloxy)-phenyl]-propionic Acid

Aqueous sodium hydroxide (1N, 5 mL, 5.0 mmol) was added to a stirred solution of (E)-(S)-2-ethoxy-3-[4-(5-phenyl-pent-2-en-4-ynyloxy)-phenyl]acid ethyl ester (example 1) (450 mg, 1.18 mmol) in ethanol (5 mL) and the resulting mixture stirred at room temperature for 16 h. The ethanol was evaporated in vacuo and the mixture acidified to pH 1 with 1N hydrochloric acid. The product was extracted into ethyl acetate (30 mL×2), and the combined organic phases dried (MgSO$_4$), filtered and evaporated to give 225 mg (54%) of the title compound as white crystals.

$^1$H NMR (CDCl$_3$, 300 MHz) δ: 1.20 (t, 3H), 2.97 (dd, 1H), 3.10 (dd, 1H), 3.42–3.65 (m, 2H), 4.05 (dd,1 H), 4.63 (dd, 2H), 6.08 (dt, 1H, J$_{trans}$=15 Hz), 6.39 (dt, 1H, J$_{trans}$=15 Hz), 6.85 (d, 2H), 7.15 (d, 2H), 7.30–7.35 (m, 3H), 7.40–7.48 (m, 2H).

$[α]_{670}^{25}$=23°+3°.

Example 3

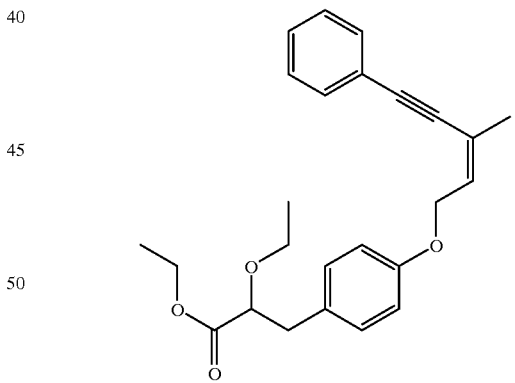

(Z)-(S)-2-Ethoxy-3-[4-(3-methyl-5-phenyl-pent-2-en-4-ynyloxy)-phenyl]-propionic Acid Ethyl Ester 1,1'-(azodicarbonyl) dipiperidine (0.504 g, 2.0 mmol) was added at 0° C. to a stirred solution of tributylphosphine (0.493 mL, 2.0 mmol), (Z)-3-methyl-5-phenyl-pent-2-en-4-yn-1-ol (0.172 g, 1.0 mmol) (J. Org. Chem. 1999, 64 (21), 7687–7692), and (S)-ethyl 2-ethoxy-3-(4-hydroxyphenyl)-propionate (0.262 g, 1.1 mmol) in dry benzene (20 mL), the mixture allowed to warm to room temperature, and stirring continued for 24 h. The resulting mixture was evaporated in vacuo, and the residue purified by flash column chromatography on silica gel (20% ethyl acetate in n-heptane eluent) to give (Z)-(S)-2-ethoxy-3-[4-(3-methyl-5-phenyl-pent-2-en-4-ynyloxy)-phenyl]-propionic acid ethyl ester as an oil; 0.267 g (68%).

¹H NMR (300 MHz, CDCl₃) δ: 1.1–1.25 (6H, m), 2.0 (3H, d), 2.93 (2H, d), 3.25–3.38 (1H, m), 3.51–3.62 (1H, m), 3.97 (1H, t), 4.13 (2H, q), 4.80 (2H, dd), 5.95 (1H, dt), 6.86 (2H, d), 7.15 (2H, d), 7.25–7.35 (3H, m), 7.40–7.43 (2H, m).

Example 4

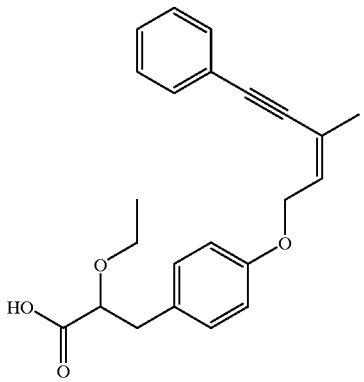

(Z)-(S)-2-Ethoxy-3-[4-(3-methyl-5-phenyl-pent-2-en-4-ynyloxy)-phenyl]-propionic acid Sodium hydroxide (1N, 1.25 mL, 1.25 mmol) was added to a solution of (Z)-(S)-2-ethoxy-3-[4-(3-methyl-5-phenyl-pent-2-en-4-ynyloxy)-phenyl]-acid ethyl ester (example 3) (0.246 g, 0.627 mmol) in ethanol (20 mL) and the mixture stirred at 70° C. for 2.5 h. After cooling to room temperature the resulting mixture was partitioned between water (50 mL) and ethyl acetate (50 mL). The aqueous phase was collected, acidified with 1N hydrochloric acid (5 mL) and extracted into ethyl acetate (100 mL). The organic phase was washed with brine, dried (Na₂SO₄) and evaporated to give (E)-(S)-3-[4-(3-biphenyl-4-yl-but-2-enyloxy)-phenyl]-2-ethoxy-propionic acid as an oil; 0.150 g (66%).

¹H NMR (300 MHz, CDCl₃) δ: 1.05 (3H, t), 1.92 (3H, d), 2.8 (1H, dd), 2.92 (1H, dd), 3.2–3.3 (1H, m), 3.4–3.5 (1H, m), 3.9 (1H, dd), 4.7 (2H, dd), 5.85 (1H, dt), 6.8 (2H, d), 7.1 (2H, d), 7.2–7.25 (3H, m), 7.3–7.4 (2H, m), 8.9 (1H, brs).

Example 5

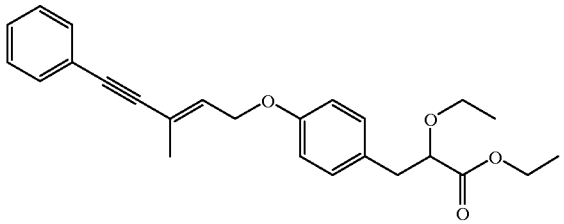

(E)-(S)-2-Ethoxy-3-[4-(3-methyl-5-phenyl-pent-2-en-4-ynyloxy)-phenyl]-propionic Acid Ethyl Ester The title compound was prepared from of (E)-3-methyl-5-phenyl-pent-2-en-4-yn-1-ol (0.172 g, 1.0 mmol), (J. Med. Chem. 1998, 41(14), 2524–2536), tributylphosphine (0.370 mL, 1.5 mmol), 1,1'-(azodicarbonyl)dipiperidine (0.378 g, 1.5 mmol) and (S)-ethyl 2-ethoxy-3-(4-hydroxy-phenyl)-propionate (0.262 g, 1.1 mmol) in dry benzene (20 mL) by a procedure analogous to that described in example 3, yielding 0.276 g (68%) of (E)-(S)-2-ethoxy-3-[4-(3-methyl-5-phenyl-pent-2-en-4-ynyloxy)-phenyl]-propionic acid ethyl ester. ¹H NMR (300 MHz, CDCl₃) δ: 1.1–1.25 (6H, m), 1.98 (3H, d), 2.95 (2H, d), 3.29–3.4 (1H, m), 3.53–3.65 (1H, m), 3.95 (1H, t), 4.15 (2H, q), 4.60 (2H, dd), 6.15 (1H, dt), 6.8 (2H, d), 7.15 (2H, d), 7.20–7.3 (3H, m), 7.35–7.45 (2H, m).

Example 6

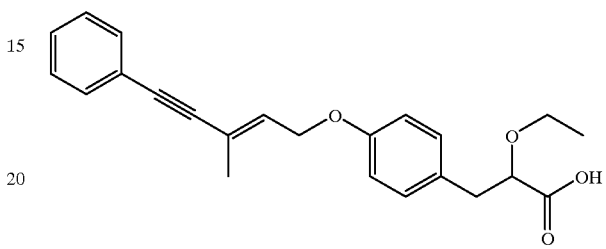

(E)-(S)-2-Ethoxy-3-[4-(3-methyl-5-phenyl-pent-2-en-4-ynyloxy)-phenyl]-propionic acid The title compound was prepared from (E)-(S)-2-ethoxy-3-[4-(3-methyl-5-phenyl-pent-2-en-4-ynyloxy)-phenyl]-propionic acid ethyl ester (example 5) (0.270 g, 0.698 mmol) and sodium hydroxide (1N, 1.4 mL, 1.4 mmol) by a procedure analogous to that described in example 4 yielding 0.100 g (39%) of (E)-(S)-2-ethoxy-3-[4-(3-methyl-5-phenyl-pent-2-en-4-ynyloxy)phenyl]-propionic acid.

¹H NMR (300 MHz, CDCl₃) δ: 1.18 (3H, t), 1.98 (3H, d), 2.9 (1H, dd), 2.05 (1H, dd), 3.4–3.5 (1H, m), 3.55–3.65 (1H, m), 4.05 (1H, dd), 4.62 (2H, dd), 6.15 (1H, m), 6.8 (2H, d), 7.15 (2H, d), 7.3 (3H, m), 7.43 (2H, m).

Example 7

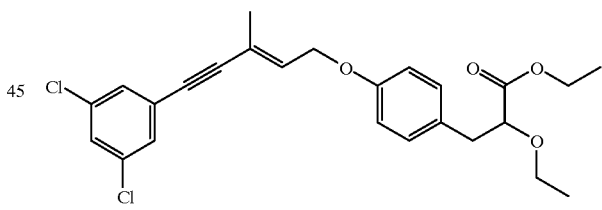

Ethyl (E)-(S)-2-Ethoxy-3-[4-(3-methyl-5-(3,5-dichloro-phenyl)-pent-2-en-4-ynyloxy)-phenyl] propionate Method 1 a)

To a solution of 1,3-dichloro-5-iodo-benzene (3.44 g, 12.6 mmol) in THF (220 mL) was added PdCl₂(PPh₃)₂ (904 mg, 1.29 mmol), 3-butyn-2-one (2.18 g, 32.0 mmol), copper(I) iodide (380 mg, 2 mmol) and diisopropylamine (44 mL). The reaction mixture was stirred at room temperature for 48 hours, filtered and evaporated. The residue was purified by column chromatography using methylene chloride:hexanes (1:1) as eluent. The desired 4-(3,5-dichloro-phenyl)-3-butyn-2-one product was isolated in 977 mg yield.

¹H NMR (300 MHz, CDCl₃) δ: 2.46 (s, 3H), 7.45 (s, 3H).

b)

To a solution of sodium (163 mg, 6.8 mmol) in ethanol (6 mL) at −10° C. was added triethyl phosphonoacetate (1.37 mL, 6.8 mmol) and the reaction mixture was stirred for 5 minutes. A solution of 4-(3,5-dichloro-phenyl)-3-butyn-2-one (214 mg, 5.7 mmol) in ethanol (4 mL) was added and the reaction mixture stirred overnight at room temperature and evaporated. The residue was treated with water (10 mL) and extracted with 3×30 mL ethyl acetate. The dried organic phases were evaporated to give a mixture of (E)- and (Z)-3-methyl-5-(3,5-dichloro-phenyl)-pent-2-en-4-ynoic acid ethyl esters. The mixture was separated by column chromatography using hexanes:methylene chloride (10:1) as eluent, giving pure (E) in 130 mg, and pure (Z) in 160 mg yields.

(E)-3-methyl-5-(3,5-dichloro-phenyl)-pent-2-en-4-ynoic acid ethyl ester: $^1$H NMR (300 MHz, CDCl$_3$) δ: 1.29 (t, 3H), 2.36 (s, 3H), 4.20 (q, 2H), 6.16 (m, 1H), 7.34 (s, 3H).

(Z)-3-methyl-5-(3,5-dichloro-phenyl)-pent-2-en-4-ynoic acid ethyl ester: $^1$H NMR (300 MHz, CDCl$_3$) δ: 1.29 (t, 3H), 2.12 (s, 3H), 2.25 (q, 2H), 6.09 (m, 1H), 7.34 (m, 1H), 7.40 (m, 2H).

c)

To a solution of (E)-3-methyl-5-(3,5-dichloro-phenyl)-pent-2-en-4-ynoic acid ethyl ester (130 mg, 0.46 mmol) in THF (0.5 mL) was added dropwise diisobutylaluminium hydride (1.0 M solution in toluene, 2.1 mL, 2.1 mmol) at −20° C. The reaction mixture was stirred for 2 hours at −20° C., where after saturated ammonium chloride was added. The mixture was treated with ethyl acetate and decalite and filtered. The filtrate was evaporated to give crude (E)-3-methyl-5-(3,5-dichloro-phenyl)-pent-2-en-4-yn-1-ol in 113 mg yield.

$^1$H NMR (300 MHz, CDCl$_3$) δ: 1.85 (s, 3H), 2.00 (br.s, 1H), 4.20 (d, 2H), 6.04 (m, 1H), 7.20 (s, 3H).

d)

To a solution of (E)-3-methyl-5-(3,5-dichloro-phenyl)-pent-2-en-4-yn-1-ol (113 mg, 0.46 mmol) in THF (10 mL) was added triphenylphosphine (218 mg, 0.71 mmol) at 0° C. To the mixture was added diethyl azodicarboxylate (0.109 mL, 0.71 mmol) and (S)-2-ethoxy-3-(4-hydroxy-phenyl)-propionic acid ethyl ester (169 mg, 0.71 mmol) and the reaction mixture was stirred at 0° C. for 2 h and then at room temperature overnight. Water (15 mL) was added and the mixture was extracted with methylene chloride (3×30 mL). The combined and dried organic phases were evaporated and the residue purified by column chromatography using methylene chloride as eluent to give the title compound in 35 mg yield.

$^1$H NMR (300 MHz, CDCl$_3$) δ: 1.16 (t, 3H), 1.23 (t, 3H), 1.98 (s, 3H), 2.97 (d, 2H), 3.42–3.30 (m, 1H), 3.65–3.55 (m, 1H), 3.97 (t, 1H), 4.16 (q, 2H), 4.62 (d, 2H), 6.20 (m, 1H), 8.83 (d, 2H), 7.16 (d, 2H), 7.37 (m, 3H).

Method 2 a)

A solution of 1-bromo-3,5-dichloro-benzene (904 mg, 4.0 mmol), PdCl$_2$(PPh$_3$)$_2$ (96 mg, 0.08 mmol), 2-methyl-3-butyn-2-ol (672 mg, 8.0 mmol) and CuI (4 mg, 0.02 mmol) in diethylamine (16 mL) was stirred at room temperature for 50 h. The reaction mixture was evaporated and the residue purified by column chromatography using methylene chloride as eluent. The desired product 3-(2,5-dichloro-phenyl)-2-methyl-3-butyn-2-ol was isolated in 910 mg (99%) yield.

$^1$H NMR (300 MHz, CDCl$_3$) δ: 1.62 (6H, s), 7.30 (3H, s).

b)

To a solution of 3-(2,5-dichloro-phenyl)-2-methyl-3-butyn-2-ol (840 mg, 3.46 mmol) in dry toluene (15 mL) was added sodium hydroxide pellets (45 mg) at room temperature. The reaction mixture was heated and a mixture of toluene and formed acetone was distilled of. The reaction mixture was washed with aqueous potassium carbonate (1M, 2.5 mL), water (2.5 mL) and brine (2.5 mL). The organic phase was dried and evaporated to give the desired product 1,3-dichloro-phenyl acetylene in 537 mg (91%) yield.

$^1$H NMR (300 MHz, CDCl$_3$) δ: 3.15 (1H, s), 7.37 (3H, s).

c)

To a solution of 1,3-dichloro-phenyl acetylene (6.07 g, 35.5 mmol) in dry THF (60 mL) was added palladium acetate (186 mg, 0.68 mmol), ethyl 2-butynoate (5.97 g, 53.2 mmol) and tris (2,6-dimethoxyphenyl)phosphine (316 mg, 0.68 mmol) at room temperature. The reaction mixture was stirred for 18 h and filtered. The filtrate was washed with water (10 mL), and the water phase was extracted with ether (10 mL). The combined organic phases were dried and evaporated. The residue was purified by column chromatography using heptane:THF (20:1) as eluent. (E)-3-Methyl-5-(3,5-dichloro-phenyl)-pent-2-en-4-ynoic acid ethyl ester was isolated in 4.65 g (46%) yield.

d)

The title compound was prepared from (E)-3-methyl-5-(3,5-dichloro-phenyl)-pent-2-en-4-ynoic acid ethyl ester according to the procedure described in method 1,c-d.

Example 8

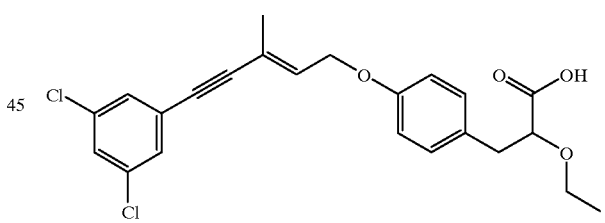

(E)-(S)-2-Ethoxy-3-[4-(3-methyl-5-(3,5-dichloro-phenyl)-pent-2-en-4-ynyloxy)-phenyl]propionic Acid Ethyl (E)-(S)-2-ethoxy-3-[4-(3-methyl-5-(3,5-dichloro-phenyl)-pent-2-en-4-ynyloxy)-phenyl]propionate was hydrolysed as described in Example 2 to give the title compound.

$^1$H NMR (300 MHz, CDCl$_3$) δ: 1.12 (t, 3H), 1.95 (s, 3H), 3.12–2.85 (m, 2H), 3.48–3.32 (m, 1H), 3.65–3.53 (m, 1H), 4.03 (m, 1H), 4.59 (d, 2H), 6.17 (t, 1H), 6.80 (d, 2H), 7.15 (d, 2H), 7.30 (s, 3H).

Example 9

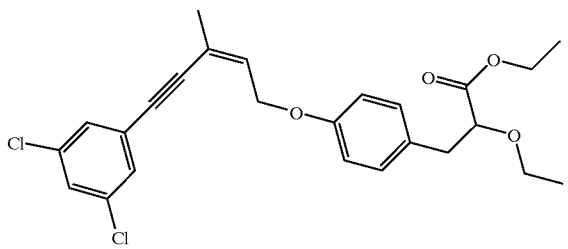

Ethyl (Z)-(S)-2-Ethoxy-3-[4-(3-methyl-5-(3,5-dichloro-phenyl)-pent-2-en-4-ynyloxy)-phenyl] propionate a)

(Z)-3-methyl-5-(3,5-dichloro-phenyl)-pent-2-en-4-yn-1-ol was made from (Z)-3-methyl-5-3,5-dichloro-phenyl)-pent-2-en-4-ynoic acid ethyl ester (160 mg) (example 7b) using the conditions described in example 7c. Yield 140 mg.

$^1$H NMR (300 MHz, CDCl$_3$) δ: 1.88 (s, 3H), 1.92 (br.s, 1H), 4.33 (d, 2H), 5.90 (t, 1H), 7.21 (s, 3H).

b)

The title compound was prepared from (Z)-3-methyl-5-(3,5-dichloro-phenyl)-pent-2-en-4-yn1-ol (140 mg) using the conditions described in example 7d. Yield 172 mg.

$^1$H NMR (300 MHz, CDCl$_3$) δ: 1.17 (t, 3H), 1.25 (t, 3H), 2.00 (s, 3H), 2.95 (d, 2H), 3.42–3.28 (m, 1H), 3.67–3.55 (m, 1H), 3.98 (t, 1H), 4.16 (q, 2H), 4.77 (d, 2H), 6.02 (t, 1H), 6.86 (d, 2H), 7.28 (d, 2H), 7.32 (s, 3H).

Example 10

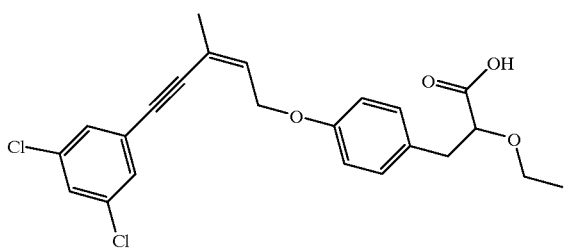

(Z)-(S)-2-Ethoxy-3-[4-(3-methyl-5-3,5-dichloro-phenyl)-pent-2-en-4-ynyloxy)-phenyl]propionic acid Ethyl (Z)-(S)-2-ethoxy-3-[4-(3-methyl-5-(3,5-dichloro-phenyl)-pent-2-en-4-ynyloxy)-phenyl]propionate was hydrolysed as described in Example 2 to give the title compound. Yield 164 mg.

$^1$H NMR (300 MHz, CDCl$_3$) δ: 1.18 (t, 3H), 2.01 (s, 3H), 3.10–2.90 (m, 2H), 3.46–3.33 (m, 1H), 3.67–3.55 (m, 1H), 4.04 (m, 1H), 4.75 (d, 2H), 6.02 (t, 1H), 6.87 (d, 2H), 7.18 (d, 2H), 7.33 (s, 3H).

Example 11

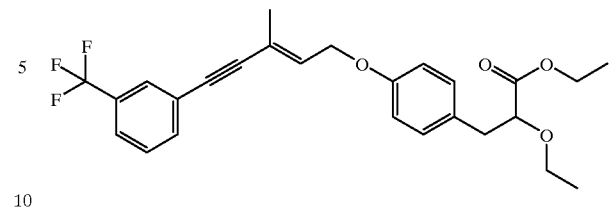

Ethyl (E)-(S)-2-Ethoxy-3-[4-(3-methyl-5-(3-trifluoromethyl-phenyl)-pent-2-en-4-ynyloxy) phenyl]-propionate The title compound was made as described in example 7a-d using 3-trifluoromethyl-1-iodobenzene instead of 1,3-dichloro-5-iodo-benzene in example 7a.

$^1$H NMR (300 MHz, CDCl$_3$) δ: 1.18 (t, 3H), 1.24 (t, 3H), 2.00 (s, 3H), 2.96 (d, 2H), 3.42–3.31 (m, 1H), 3.66–3.55 (m, 1H), 3.98 (t, 1H), 4.27 (q, 2H), 4.65 (d, 2H), 6.23 (1H), 6.84 (d, 2H), 7.18 (d, 2H), 7.71–7.38 (m, 5H).

Example 12

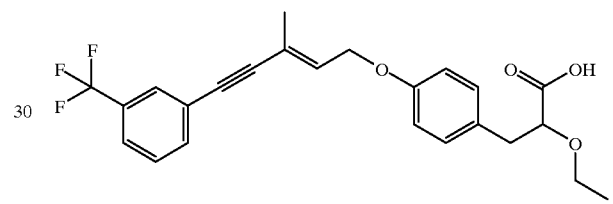

(E)-(S)-2-Ethoxy-3-[4-(3-methyl-5-(3-trifluoromethyl-phenyl)-pent-2-en-4-ynyloxy)-phenyl]-propionic acid Ethyl (E)-(S)-2-ethoxy-3-[4-(3-methyl-5-(3-trifluoromethyl-phenyl)-pent-2-en-4-ynyloxy)phenyl]-propionate was hydrolysed as described in Example 2 to give the title compound.

$^1$H NMR (300 MHz, CDCl$_3$) δ: 1.19 (t, 3H), 1.98 (s, 3H), 3.12–2.90 (m, 2H), 3.48–3.36 (m, 1H), 3.69–3.56 (m, 1H), 4.50 (m, 1H), 4.64 (d, 2H), 6.21 (t, 1H), 6.85 (d, 2H), 7.18 (d, 2H), 7.70–7.49 (m, 5H).

Example 13

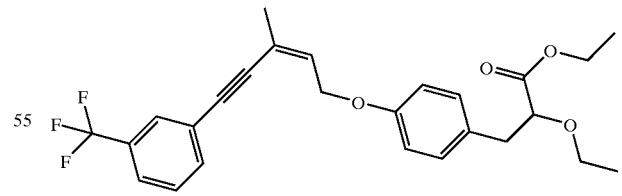

Ethyl (Z)-(S)-2-Ethoxy-3-[4-(3-methyl-5-(3-trifluoromethyl-phenyl)-pent-2-en-4-ynyloxy) phenyl]-propionate The title compound was synthesised from (Z)-3-methyl-5-(3-trifluromethyl-phenyl)-pent-2-en-4-yn-1-ol which was derived from the reaction sequence described in example 11 using the conditions described in example 7c–d.

¹H NMR (300 MHz, CDCl₃) δ: 1.18 (t, 3H), 2.23 (t, 3H), 2.03 (s, 3H), 2.96 (d, 2H), 3.42–3.30 (m, 1H), 3.66–3.55 (m, 1H), 3.96 (t, 1H), 4.15 (q, 2H), 4.82 (d, 2H), 6.03 (t, 1H), 6.87 (d, 2H), 7.17 (d, 2H), 7.70–7.43 (m, 5H).

Example 14

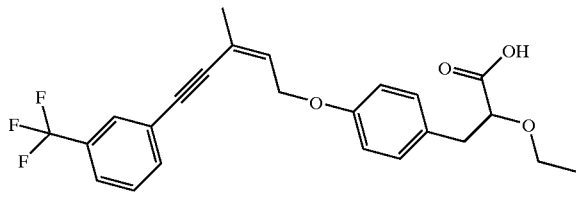

(Z)-(S)-2-Ethoxy-3-[4-(3-methyl-5-(3-trifluoromethyl-phenyl)-pent-2-en-4-ynyloxy)-phenyl]propionic acid Ethyl (Z)-(S)-2-ethoxy-3-[4-(3-methyl-5-(3-trifluoromethyl-phenyl)-pent-2-en-4-ynyloxy)phenyl]-propionate was hydrolysed as described in Example 2 to give the title compound.

¹H NMR (300 MHz, CDCl₃) δ: 1.16 (t, 3H), 2.02 (s, 3H), 3.10–2.92 (m, 2H), 3.47–3.36 (m, 1H), 3.68–3.57 (m, 1H), 4.03 (m, 1H), 4.80 (d, 2H), 6.02 (t, 1H), 6.89 (d, 2H), 7.18 (d, 2H), 7.72–7.42 (m, 5H).

Example 15

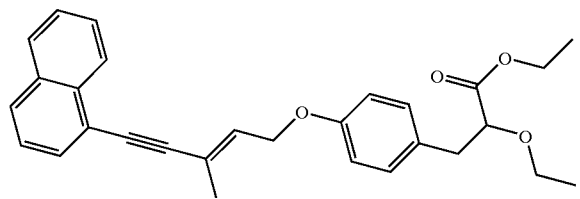

Ethyl (E)-(S)-2-Ethoxy-3-[4-(3-methyl-5-(1-naphthyl)-pent-2-en-4-ynyloxy)-phenyl]-propionate The title compound was made as described in example 7a–d using 1-iodonaphthalene instead of 1,3-dichloro-5-iodo-benzene in example 7a.

¹H NMR (300 MHz, CDCl₃) δ: 1.18 (t, 3H), 1.24 (t, 3H), 2.08 (s, 3H), 2.96 (d, 2H), 3.42–3.30 (m, 1H), 3.66–3.53 (m, 1H), 3.98 (t, 1H), 4.15 (q, 2H), 4.65 (d, 2H), 6.30 (m, 1H), 6.86 (d, 2H), 7.18 (d, 2H), 7.86–7.38 (m, 6H), 8.33 (d, 1H).

Example 16

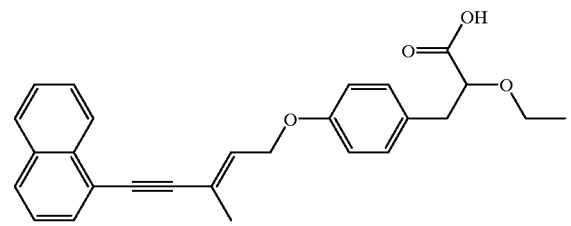

(E)-(S)-2-Ethoxy-3-[4-(3-methyl-5-(1-naphthyl)-pent-2-en-4-ynyloxy)-phenyl]-propionic acid Ethyl (E)-(S)-2-ethoxy-3-[4-(3-methyl-5-(1-naphthyl)-pent-2-en-4-ynyloxy)-phenyl]-propionate was hydrolysed as described in Example 2 to give the title compound.

¹H NMR (300 MHz, CDCl₃) δ: 1.19 (t, 3H), 1.98 (s, 3H), 3.12–2.90 (m, 2H), 3.48–3.36 (m, 1H), 3.69–3.56 (m, 1H), 4.05 (m, 1H), 4.66 (d, 2H), 6.30 (t, 1H), 6.85 (d, 2H), 7.18 (d, 2H), 7.90–7.45 (m, 6H), 8.44 (d, 1H).

Example 17

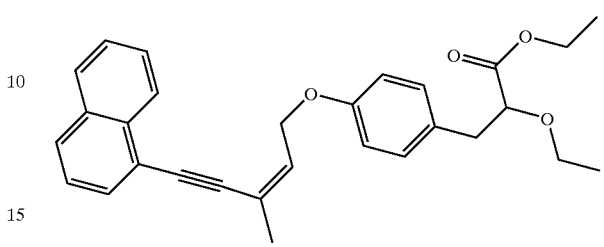

Ethyl (Z)-(S)-2-Ethoxy-3-[4-(3-methyl-5-(1-naphthyl)-pent-2-en-4-ynyloxy)-phenyl]-propionate The title compound was synthesised from (Z)-3-methyl-5-(1-naphthyl)-pent-2-en-4-yn-1-ol isolated in example 15 using the conditions described in example 7c–d.

¹H NMR (300 MHz, CDCl₃) δ: 1.18 (t, 3H), 1.23 (t, 3H), 2.14 (s, 3H), 2.97 (d, 2H), 3.42–3.30 (m, 1H), 3.66–3.53 (m, 1H), 3.98 (t, 1H), 4.15 (q, 2H), 4.95 (d, 2H), 6.06 (m, 1H), 6.94 (d, 2H), 7.18 (d, 2H), 7.86–7.40 (m, 6H), 8.30 (m, 1H).

Example 18

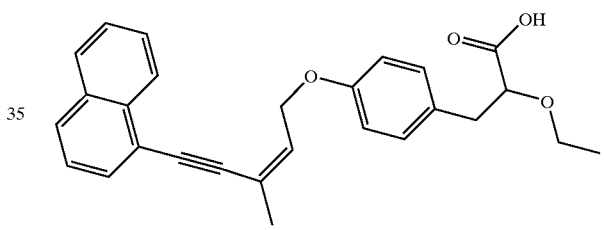

(Z)-(S)-2-Ethoxy-3-[4-(3-methyl-5-(1-naphthyl)-pent-2-en-4-ynyloxy)-phenyl]-propionic acid Ethyl (Z)-(S)-2-ethoxy-3-[4-(3-methyl-5-(1-naphthyl)-pent-2-en-4-ynyloxy)-phenyl]-propionate was hydrolysed as described in Example 2 to give the title compound.

¹H NMR (300 MHz, CDCl₃) δ: 1.04 (t, 3H), 2.02 (s, 3H), 3.00–2.80 (m, 2H), 3.34–3.22 (m, 1H), 3.57–3.46 (m, 1H), 3.94 (m, 1H), 4.83 (d, 2H), 5.94 (t, 1H), 6.84 (d, 2H), 7.08 (d, 2H), 7.75–7.26 (m, 6H), 8.20 (m, 1H), 9.2 (br.s, 1H).

Example 19

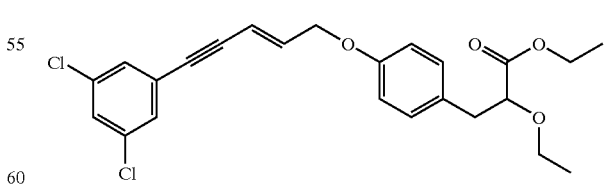

Ethyl (E)-(S)-2-Ethoxy-3-[4-(-5-(3,5-dichloro-phenyl)-pent-2-en-4-ynyloxy)-phenyl]-propionate a)

To a solution of 1,3-dichloro-5-iodo-benzene (5.44 g, 20 mmol) in diethylamine (75 mL) was added PdCl₂(PPh₃)₂

(280 mg, 0.4 mmol), trimethylsilylacetylene (2.36 g, 24.0 mmol) and copper(I)iodide (20 mg, 0.1 mmol). The reaction mixture was stirred at room temperature for 24 h, filtered and evaporated. The residue was purified by column chromatography using heptane:ethyl acetate (8:2) as eluent. The desired (3,5-dichloro-phenylethynyl)-trimethylsilane product was isolated in 4.85 g yield.

$^1$H NMR (300 MHz, CDCl$_3$) δ: 0.09 (s, 9H), 7.15 (m, 3H).

b)

To a solution of (3,5-dichloro-phenylethynyl)-trimethylsilane (4.85 g, 19.9 mmol) in methanol (50 mL) was added 1M potassium hydroxide (30 mL). The reaction mixture was stirred 1 h at room temperature and evaporated. The residue was treated with water (10 mL) and extracted with 3×40 mL diethyl ether. The tried organic phases were evaporated to give the desired 1,3-dichloro-5-ethynyl-benzene product in 2.3 g yield.

$^1$H NMR (300 MHz, CDCl$_3$) δ: 2.13 (s, 1H), 7.38 (s, 3H).

c)

To a solution of 1,3-dichloro-5-ethynyl-benzene (1.52 g, 8.9 mmol) in triethylamine (32.4 mL) was added PdCl$_2$(PPh$_3$)$_2$ (57.15 mg, 0.08 mmol), (E)-3-iodo-prop-2-enoic-acid ethyl ester (1.84 g, 8.1 mmol) and copper(I)iodide (7.7 mg, 0.04 mmol). The reaction mixture was stirred for 2 h at 50° C., whereafter the reaction mixture was cooled to room temperature, water (30 mL) added and the mixture extracted with diethyl ether (3×20 mL). The combined and dried organic phases were evaporated to give crude (E)-5-(3,5-dichloro-phenyl)-pent-2-en-4-ynoic acid ethyl ester in 1.1 g yield.

$^1$H NMR (300 MHz, CDCl$_3$) δ: 1.32 (t, 3H), 4.22 (q, 2H), 6.32 (d, 1H, J=16 Hz), 6.92 (d, 1H, J=16 Hz), 7.37 (s, 3H).

d)

To a solution of diisobutylaluminium hydride (1.0 M solution in toluene, 20 mL, 20 mmol) at −78° C. was slowly added (E)-5-(3,5-dichloro-phenyl)-pent-2-en-4-ynoic acid ethyl ester (1.1 g, 4.08 mmol). The reaction mixture was stirred for 2 h at −78° C., where after the reaction mixture was poured into hydrocloride acid (6N, 50 mL) and extracted with diethyl ether (3×40 mL) The combined and dried organic phases were evaporated to give crude (E)-5-3,5-dichloro-phenyl)-pent-2-en-4-yn-1-ol in 750 mg yield.

$^1$H NMR (300 MHz, CDCl$_3$) δ: 4.3 (dd, 2H), 5.95 (dt, 1H, J=5 and 16 Hz), 6.4 (dt, 1H, J=5 and 16 Hz), 7.30 (s, 3H).

e)

The title compound was prepared from (E)-5-(3,5-dichloro-phenyl)-pent-2-en-4-yn-1-ol (454 mg, 2 mmol) using the conditions described in example 7d. Yield 125 mg yield.

$^1$H NMR (300 MHz, CDCl$_3$) δ: 1.14 (t, 3H), 1.22 (t, 3H), 2.95 (d, 2H), 3.30–3.42 (m, 1H), 3.55–3.67 (m, 1H), 3.95 (t, 1H), 4.16 (q, 2H), 4.6 (dd, 2H, J=1.5 and 5 Hz), 6.05 (dt, 1H, J=1.5 and 16 Hz), 6.35 (dt, 1H, J=5 and 16 Hz), 6.83 (d, 2H), 7.15 (d, 2H), 7.36 (m, 3H).

Example 20

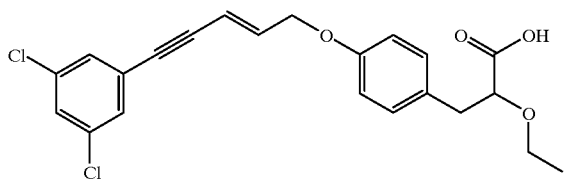

(E)-(S)-2-Ethoxy-3-[4-(5-(3,5-dichloro-phenyl)-pent-2-en-4-ynyloxy)-phenyl]-propionic Acid Ethyl (E)-(S)-2-ethoxy-3-[4-(5-(3,5-dichloro-phenyl)-pent-2-en-4-ynyloxy)-phenyl]-propionate was hydrolysed as described in Example 2 to give the title compound.

$^1$H NMR (300 MHz, CDCl$_3$) δ: 1.19 (t, 3H), 2.88–3.12 (m, 2H), 3.37–3.50 (m, 1H), 3.65–3.70 (m, 1H), 4.05 (m, 1H), 4.70 (dd, 2H, J=1.5 and 5 Hz), 6.1 (dt, 1H, J=1.5 and 16 Hz), 6.45 (dt, 1H, J=5 and 16 Hz), 6.85 (d, 2H), 7.18 (d, 2H), 7.30 (s, 3H).

Example 21

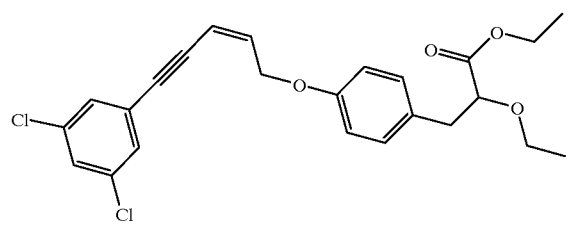

Ethyl (Z)-(S)-2-Ethoxy-3-[4-(3-methyl-5-(3,5-dichloro-phenyl)-pent-2-en-4-ynyloxy)-phenyl]-propionate a)

(Z)-5-(3,5-Dichloro-phenyl)-pent-2-en-4-ynoic acid ethyl ester was made from cis-3-iodo acrylic acid ethyl ester (*Can J Chem*, 72 (8), 1816–1819, 1994). (4 g) using the conditions described in example 19 c. Yield 4.62 g.

$^1$H NMR (300 MHz, CDCl$_3$) δ: 1.4 (t, 3H), 4.3 (q, 2H), 6.2 (d, 1H, J=11 Hz), 6.34 (d, 1H, J=11 Hz), 7.32 (s, 1H) 7.4 (s, 2H).

b)

(Z)-5-(3,5-dichloro-phenyl)-pent-2-en-4-yn-1-ol was made from (Z)-5-(3,5-dichloro-phenyl)-pent-2-en-4-ynoic acid ethyl ester (4.6 g) using the conditions described in example 19 d. Yield 3.63 g.

$^1$H NMR (300 MHz, CDCl$_3$) δ: 4.4 (dd, 2H, J=1.5 and 6.5 Hz), 5.75 (dt, 1H, J=1.5 and 11 Hz), 6.21 (dt, 1H, J=6.5 and 11 Hz), 7.3 (s, 3H).

c)

The title compound was from (Z)-5-(3,5-dichloro-phenyl)-pent-2-en-4-yn-1-ol (300 mg, 1.32 mmol) using the conditions described in example 19 e. Yield 180 mg yield.

$^1$H NMR (300 MHz, CDCl$_3$) δ: 1.12 (t, 3H), 1.2 (t, 3H), 2.9 (d, 2H), 3.26–3.44 (m, 1H), 3.51–3.69 (m, 1H), 3.94 (t, 1H), 4.14 (q, 2H), 4.85 (dd, 2H, J=1.8 and 6.3 Hz), 5.87 (dt, 1H, J=1.8 and 11 Hz), 6.25 (dt, 1H, J=6.3 and 11 Hz), 6.82 (d, 2H), 7.15 (d, 2H), 7.33 (m, 3H).

Example 22

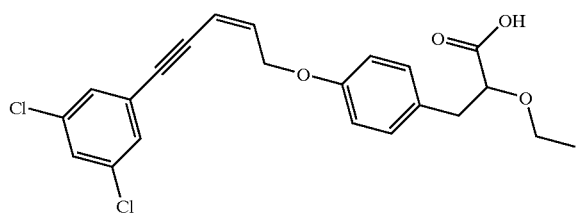

(Z)-(S)-2-Ethoxy-3-[4-(3-methyl-5-(3,5-dichloro-phenyl)-pent-2-en-4-ynyloxy)-phenyl]propionic Acid Ethyl (Z)-(S)-2-ethoxy-3-[4-(3-methyl-5-(3,5-dichloro-phenyl)-pent-2-en-4-ynyloxy)-phenyl]propionate was hydrolysed as described in Example 2 to give the title compound. Yield 100 mg.

¹H NMR (300 MHz, DMSO-D₆) δ: 1.16 (t, 3H), 2.85–3.05 (m, 2H), 3.3–3.45 (m, 1H), 3.6–3.7 (m, 1H), 4.06 (m, 1H), 4.9 (dd, 2H, J=1.8 and 6.2 Hz), 6.1 (dt, 1H, J=1.8 and 11 Hz), 6.45 (dt, 1H, J=6.2 and 11 Hz), 6.93 (d, 2H), 7.20 (d, 2H), 7.65 (d, 2H), 7.71 (d,1H).

Example 23

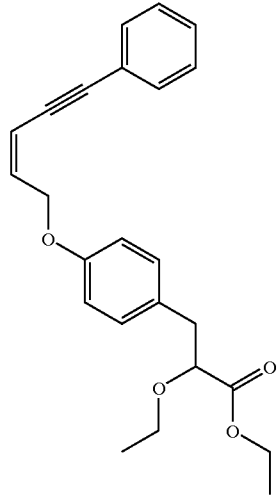

(Z)-(S)-2-Ethoxy-3-[4-(5-phenyl-pent-2-en-4-ynyloxy)-phenyl]-propionic Acid Ethyl Ester a)
(Z)-5-phenyl-pent-2-en-4-ynoic acid ethyl ester was made from cis-3-iodo acrylic acid ethyl ester (2 g) and phenylacetylene using the conditions described in example 19 c. Yield 1.24 g.

¹H NMR (300 MHz, CDCl₃) δ: 1.3 (t, 3H), 4.25 (q, 2H), 6.12 (d, 1H, $J_{cis}$=11.3 Hz), 6.35 (d, 1H, $J_{cis}$=11.3 Hz), 7.36 (m, 3H) 7.53 (m, 2H).

b)
(Z)-5-phenyl-pent-2-en-4-yn-1-ol was made from (Z)-5-phenyl-pent-2-en-4-ynoic acid ethyl ester (1.0 g) using the conditions described in example 19 d. Yield 0.7 g.

¹H NMR (300 MHz, CDCl₃) δ: 4.5 (dd, 2H, J=1.5 and 6.5 Hz), 5.80 (dt, 1H, J=1.5 and 10.5 Hz), 6.14 (dt, 1H, J=6.4 and 10.5 Hz), 7.31 (m, 3H), 7.43 (m, 2H).

c)
The title compound was prepared from (Z)-5-phenyl-pent-2-en-4-yn-1-ol (200 mg, 1.3 mmol) using the conditions described in example 19 e. Yield 380 mg.

¹H NMR (300 MHz, CDCl₃) δ: 1.2 (dt, 6H), 2.98 (d, 2H), 3.3–3.41 (m, 1H), 3.53–3.68 (m, 1H), 3.95 (t, 1H), 4.18 (q, 2H), 4.9 (dd, 2H, J=1.6 and 6.4 Hz), 5.95 (dt, 1H, J=1.6 and 11 Hz), 6.2 (dt, 1H, J=6.4 and 11 Hz), 6.89 (d, 2H), 7.17 (d, 2H), 7.35 (m, 3H)), 7.47 (m, 2H).

Example 24

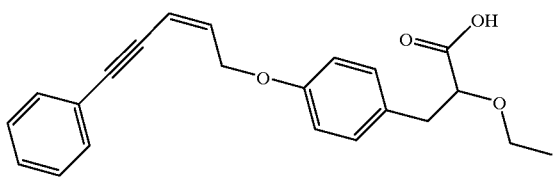

(Z)-(S)-2-Ethoxy-3-[4-(5-phenyl-pent-2-en-4-ynyloxy)-phenyl]-propionic Acid

Ethyl (Z)-(S)-2-ethoxy-3-[4-(phenyl-pent-2-en-4-ynyloxy)-phenyl]-propionate was hydrolysed as described in Example 2 to give the title compound. Yield 264 mg. ¹H NMR (300 MHz, DMSO-D₆) δ: 1.15 (t, 3H), 2.8–3.0 (m, 2H), 3.3–3.4 (m, 1H), 3.5–3.65 (m, 1H), 3.96 (m, 1H), 4.89 (dd, 2H, J=1.6 and 6.3 Hz), 6.08 (dt, 1H, J=1.6 and 11 Hz), 6.3 (dt, 1H, J=6.3 and 11 Hz), 6.9 (d, 2H), 7.20 (d, 2H), 7.4 (m, 3H), 7.5 (m, 2H).

Example 25

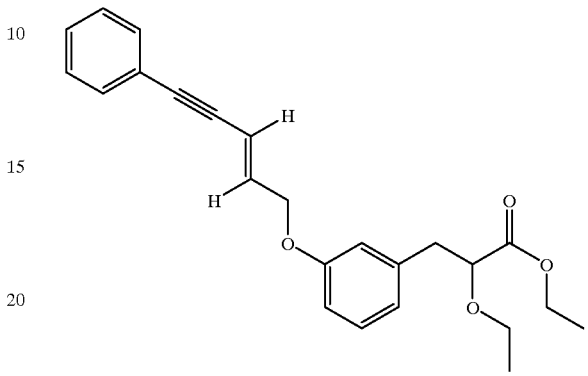

(E)-(RS)-2-Ethoxy-3-[3-(5-phenyl-pent-2-en-4-ynyloxy)-phenyl]-propionic Acid Ethyl Ester a)
NaH 60% in paraffin oil (1.189, 29.5 mmol) was added to a solution of diethoxy-phosphoryl-ethoxy-ethylacetate (7.46 g, 27.8 mmol)) in dry THF (40 mL) at 0° C. 3-Benzyloxybenzaldehyde (ALDRICH) (5.0 g, 23.6 mmol) dissolved in dry THF (20 mL) was added dropwise keeping the temperature below 10° C. The reaction mixture was allowed to reach room temperature followed by the addition of water. The product was extracted into MTBE, and the combined organic phases dried (Na₂SO₄), filtered and evaporated to give 7.6 g (99%) of (E,Z)-3-(3-benzyloxyphenyl)-2-ethoxyacrylic acid ethyl ester as a yellow oil.

¹H NMR (CDCl₃, 400 MHz) δ: 1.09 (t), 1.34 (t), 1.37 (t), 3.92 (q), 3.98 (q), 4.12 (q), 4.30 (q), 5.04 (s), 5.09 (s), 6.95 (s), 7.26 (s), 7.2–7.5 (m).

b)
(E,Z)-3-(3-Benzyloxyphenyl)-2-ethoxyacrylic acid ethyl ester (6.8 g) dissolved in ethyl acetate (40 mL) was hydrogenated at 10 bar using Pd/C (10%) (1.08 g) until the reaction was shown to be completed by HPLC. The reaction mixture was filtered through a pad of celite and the solvent evaporated. The product was purified by column chromatography eluting with ethyl acetate/heptane 1:2 to give 3.1 g (62%) of (R,S)-2-ethoxy-3-hydroxyphenyl)propanoic acid ethyl ester.

¹H NMR (CDCl₃, 400 MHz) δ: 1.16 (t, 3H), 1.23 (t, 3H), 2.97–2.95 (m, 2H), 3.41–3.33 (dq, 1H), 3.65–3.57 (dq, 1H), 4.02 (t, 1H), 4.17 (q, 2H), 5.33 (s, 1H), 6.81–6.70 (m, 3H), 7.15 (t, 1H). ¹³C-NMR (75 MHz, CDCl₃) δ: 14.51, 15.36, 39,58, 61,48, 66,74, 80.52, 114.15, 116.87, 121.79, 129.81, 139.07, 156.20, 173.27. MS m/z (MH⁺) 239.2. Elemental analysis: Anal. Calcd. for $C_{13}H_{18}O_4$: C, 65.53; H, 7.61%. Found: C, 65.98; H, 7.96.

c)
The title compound (120 mg, 63%) was prepared from (R,S)-2-ethoxy-3-(3-hydroxyphenyl)propanoic acid ethyl ester (120 mg, 0.5 mmol) and (E)-5-phenyl-pent-2-en4-yn-1-ol (example 1, method 1b)(79 mg, 0.5 mmol), by a procedure analogous to that described in example 1 (method 1c).

What is claimed is:

1. A compound of formula (I)

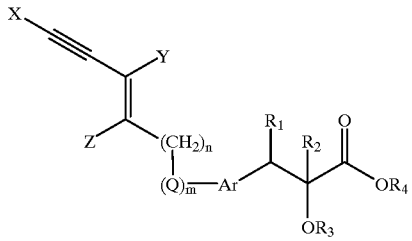

wherein

X is hydrogen or

X is $C_{1-12}$-alkyl, $C_{2-12}$-alkenyl, $C_{2-12}$-alkynyl, aryl, heteroaryl, aralkyl, heteroaralkyl or heterocyclyl each of which is optionally substituted with one or more substituents selected from halogen, perhalomethyl, hydroxy, $C_{1-6}$-alkyl, $C_{2-6}$-alkenyl, $C_{2-6}$-alkynyl, hydroxy, $C_{1-6}$-alkoxy, $C_{1-6}$-alkylthio, aryl, aryloxy, arylthio, acyl, aralkyl, aralkoxy, heteroaryl, heteroaralkyl, heteroaryloxy, heteroaralkoxy, $C_{1-6}$-alkylthio, cyano, amino, $C_{1-6}$-alkylamino, $C_{1-6}$-dialkylamino, carboxy or $C_{1-6}$-alkylester; and Y is hydrogen or Y is $C_{1-12}$-alkyl, $C_{2-12}$-alkenyl, $C_{2-12}$-alkynyl, $C_{4-12}$-alkenynyl, aryl, heteroaryl, aralkyl or heteroaralkyl each of which is optionally substituted with one or more substituents selected from halogen, $C_{1-6}$-alkyl, perhalomethyl, hydroxy, aryl, heteroaryl, amino, carboxy or $C_{1-6}$-alkylester; and Z is hydrogen, halogen, hydroxy or Z is $C_{1-6}$-alkyl or $C_{1-6}$-alkoxy each of which is optionally substituted with one or more substituents selected from $C_{1-6}$-alkoxy, halogen, hydroxy, carboxy, amino or cyano; and Q is O, S or $NR_5$, wherein $R_5$ is hydrogen, $C_{1-6}$-alkyl, $C_{2-6}$-alkenyl, $C_{2-6}$-alkynyl, $C_{4-6}$-alkenynyl, aralkyl or heteroaralkyl and wherein $R_5$ is optionally substituted with one or more substituents selected from halogen, hydroxy, $C_{1-6}$-alkoxy, amino or carboxy; and Ar is arylene, heteroarylene or a divalent heterocyclic group each of which can be optionally substituted with one or more substituents selected from $C_{1-6}$-alkyl, aryl or $C_{1-6}$-alkoxy each of which can be optionally substituted with halogen, hydroxy, carboxy or $C_{1-6}$-alkylester; and $R_1$ is hydrogen, hydroxy or halogen; or $R_1$ forms a bond together with $R_2$; and $R_2$ is hydrogen or $C_{1-6}$-alkyl; or $R_2$ forms a bond together with $R_1$; and $R_3$ is hydrogen, $C_{1-6}$-alkyl, $C_{2-6}$-alkenyl, $C_{2-6}$-alkynyl, $C_{4-6}$-alkenynyl, aryl, aralkyl, $C_{1-6}$-alkoxy$C_{1-6}$-acyl, heterocyclyl, heteroaryl or heteroaralkyl groups optionally substituted with one or more substituents selected from halogen, perhalomethyl, hydroxy, cyano, carboxy or $C_{1-6}$-alkylester; and $R_4$ is hydrogen, $C_{1-6}$-alkyl, $C_{2-6}$-alkenyl, $C_{2-6}$-alkynyl, $C_{4-6}$-alkenynyl or aryl;

n is an integer ranging from 0 to 3; and m is an integer ranging from 0 to 1;

or a pharmaceutically acceptable salt thereof, or a pharmaceutically acceptable solvate thereof, or any tautomeric forms, stereoisomers, mixture of stereoisomers including a racemic mixture, or polymorphs.

2. A compound according to claim 1 of formula (I)

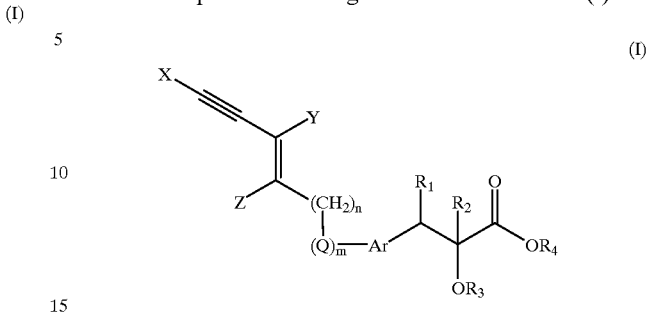

wherein

X is hydrogen or

X is $C_{1-12}$-alkyl, $C_{2-12}$-alkenyl, $C_{2-12}$-alkynyl, aryl, heteroaryl, aralkyl, heteroaralkyl or heterocyclyl each of which is optionally substituted with one or more substituents selected from halogen, perhalomethyl, hydroxy, $C_{1-6}$-alkyl, $C_{2-6}$-alkenyl, $C_{2-6}$-alkynyl, hydroxy, $C_{1-6}$-alkoxy, $C_{1-6}$-alkylthio, aryl, aryloxy, arylthio, acyl, aralkyl, aralkoxy, heteroaryl, heteroaralkyl, heteroaryloxy, heteroaralkoxy, $C_{1-6}$-alkylthio, cyano, amino, $C_{1-6}$-alkylamino, $C_{1-6}$-dialkylamino, carboxy or $C_{1-6}$-alkylester; and Y is hydrogen or Y is $C_{1-12}$-alkyl, $C_{2-12}$-alkenyl, $C_{2-12}$-alkynyl, $C_{4-12}$-alkenynyl, aryl, heteroaryl, aralkyl or heteroaralkyl each of which is optionally substituted with one or more substituents selected from halogen, $C_{1-6}$-alkyl, perhalomethyl, hydroxy, aryl, heteroaryl, amino, carboxy or $C_{1-6}$-alkylester; and Z is hydrogen, halogen, hydroxy or Z is $C_{1-6}$-alkyl or $C_{1-6}$-alkoxy each of which is optionally substituted with one or more substituents selected from $C_{1-6}$-alkoxy, halogen, hydroxy, carboxy, amino or cyano; and Q is O, S or $NR_5$, wherein $R_5$ is hydrogen, $C_{1-6}$-alkyl, $C_{2-6}$-alkenyl, $C_{2-6}$-alkynyl, $C_{4-6}$-alkenynyl or heteroaralkyl and wherein $R_5$ is optionally substituted with one or more substituents selected from halogen, hydroxy, $C_{1-6}$-alkoxy, amino or carboxy; and Ar is arylene, heteroarylene or a divalent heterocyclic group each of which can be optionally substituted with one or more substituents selected from $C_{1-6}$-alkyl, aryl or $C_{1-6}$-alkoxy each of which can be optionally substituted with halogen, hydroxy, carboxy or $C_{1-6}$-alkylester; and $R_1$ is hydrogen, hydroxy or halogen; or $R_1$ forms a bond together with $R_2$; and $R_2$ is hydrogen or $C_{1-6}$-alkyl; or $R_2$ forms a bond together with $R_1$; and $R_3$ is hydrogen, $C_{1-6}$-alkyl, $C_{2-6}$-alkenyl, $C_{2-6}$-alkynyl, $C_{4-6}$-alkenynyl, aryl, aralkyl, $C_{1-6}$-alkoxy$C_{1-6}$-alkyl, acyl, heterocyclyl, heteroaryl or heteroaralkyl groups optionally substituted with one or more substituents selected from halogen, perhalomethyl, hydroxy, cyano, carboxy or $C_{1-6}$-alkylester; and $R_4$ is hydrogen, $C_{1-6}$-alkyl, $C_{2-6}$-alkenyl, $C_{2-6}$-alkynyl, $C_{4-6}$-alkenynyl or aryl;

n is an integer ranging from 1 to 3; and m is 1;

or a pharmaceutically acceptable salt thereof, or a pharmaceutically acceptable solvate thereof, or any tautomeric forms, stereoisomers, mixture of stereoisomers including a racemic mixture, or polymorphs.

3. A compound of formula (I)

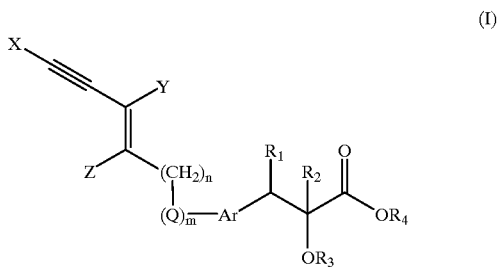

wherein

X is hydrogen, $C_{1-2}$-alkyl, $C_{2-12}$-alkenyl, $C_{2-12}$-alkynyl, aryl, heteroaryl, aralkyl, heteroaralkyl or heterocyclyl optionally substituted with one or more substituents selected from halogen, perhalomethyl, hydroxy, $C_{1-6}$-alkyl, $C_{2-6}$-alkenyl, $C_{2-6}$-alkynyl, hydroxy, $C_{1-6}$-alkoxy, $C_{1-6}$-alkylthio, aryl, aryloxy, arylthio, acyl, aralkyl, aralkoxy, heteroaryl, heteroaralkyl, heteroaryloxy, heteroaralkoxy, $C_{1-6}$-alkylthio, cyano, amino, $C_{1-6}$-alkylamino, $C_{1-6}$-dialkylamino, carboxy or $C_{1-6}$-alkylester; and Y is hydrogen, $C_{1-12}$-alkyl, $C_{2-12}$-alkenyl, $C_{2-12}$-alkynyl, $C_{4-12}$-alkenynyl, aryl, heteroaryl, aralkyl or heteroaralkyl optionally substituted with one or more substituents selected from halogen, $C_{1-6}$-alkyl, perhalomethyl, hydroxy, aryl, heteroaryl, amino, carboxy or $C_{1-6}$-alkylester; and Z is hydrogen, halogen, hydroxy, $C_{1-6}$-alkyl or $C_{1-6}$-alkoxy optionally substituted with one or more substituents selected from $C_{1-6}$-alkoxy, halogen, hydroxy, carboxy, amino or cyano; and Q is O, S or $NR_5$, wherein $R_5$ is hydrogen, $C_{1-6}$-alkyl, $C_{2-6}$-alkenyl, $C_{2-6}$-alkynyl, $C_{4-6}$-alkenynyl, aralkyl or heteroaralkyl and wherein $R_5$ is optionally substituted with one or more substituents selected from halogen, hydroxy, $C_{1-6}$-alkoxy, amino or carboxy; and Ar is arylene, heteroarylene or a divalent heterocyclic group each of which can be optionally substituted with one or more substituents selected from $C_{1-6}$-alkyl, aryl or $C_{1-6}$-alkoxy each of which can be optionally substituted with halogen, hydroxy, carboxy or $C_{1-6}$-alkylester; and $R_1$ is hydrogen, hydroxy or halogen; or $R_1$ forms a bond together with $R_2$; and $R_2$ is hydrogen or $C_{1-6}$-alkyl; or $R_2$ forms a bond together with $R_1$; and $R_3$ is hydrogen, $C_{1-6}$-alkyl, $C_{2-6}$-alkenyl, $C_{2-6}$-alkynyl, $C_{4-6}$-alkenynyl, aryl, aralkyl, $C_{1-6}$-alkoxy$C_{1-6}$-alkyl, acyl, heterocyclyl, heteroaryl or heteroaralkyl groups optionally substituted with one or more substituents selected from halogen, perhalomethyl, hydroxy, cyano, carboxy or $C_{1-6}$-alkylester; and $R_4$ is hydrogen, $C_{1-6}$-alkyl, $C_{2-6}$-alkenyl, $C_{2-6}$-alkynyl, $C_{4-6}$-alkenynyl or aryl;

n is an integer ranging from 0 to 3; and m is an integer ranging from 0 to 1;

or a pharmaceutically acceptable salt thereof, or a pharmaceutically acceptable solvate thereof, or any tautomeric forms, stereoisomers, mixture of stereoisomers including a racemic mixture, or polymorphs.

4. A compound according to claim 1 wherein X is aryl, heteroaryl or heterocyclyl optionally substituted with one or more substituents selected from halogen, perhalomethyl, $C_{1-6}$-alkoxy, $C_{1-6}$-alkylthio, aryl, aryloxy, arylthio, aralkyl, aralkoxy, heteroaryl, heteroaralkyl, heteroaryloxy or heteroaralkoxy.

5. A compound according to claim 1 wherein X is aryl optionally substituted with one or more substituents selected from halogen, perhalomethyl, $C_{1-6}$-alkoxy, $C_{1-6}$-alkylthio, aryl, aryloxy, arylthio, aralkyl, aralkoxy, heteroaryl, heteroaralkyl, heteroaryloxy or heteroaralkoxy.

6. A compound according to claim 1 wherein X is phenyl or naphthyl each of which is optionally substituted with one or more substituents selected from halogen or perhalomethyl.

7. A compound according to claim 1 wherein X is phenyl optionally substituted with one or more substituents selected from halogen.

8. A compound according to claim 1 wherein X is heteroaryl optionally substituted with one or more substituents selected from halogen, perhalomethyl, $C_{1-6}$-alkoxy, $C_{1-6}$-alkylthio, aryl, aryloxy, arylthio, aralkyl, aralkoxy, heteroaryl, heteroaralkyl, heteroaryloxy or heteroaralkoxy.

9. A compound according to claim 1 wherein X is heterocyclyl optionally substituted with one or more substituents selected from halogen, perhalomethyl, $C_{1-6}$-alkoxy, $C_{1-6}$-alkylthio, aryl, aryloxy, arylthio, aralkyl, aralkoxy, heteroaryl, heteroaralkyl, heteroaryloxy or heteroaralkoxy.

10. A compound according to claim 1 wherein Y is hydrogen, $C_{1-12}$-alkyl or aryl.

11. A compound according to claim 1 wherein Y is hydrogen or methyl.

12. A compound according to claim 1 wherein Z is hydrogen or $C_{1-6}$-alkoxy.

13. A compound according to claim 1 wherein Q is O.

14. A compound according to claim 1 wherein Ar is arylene optionally substituted with one or more substituents selected from $C_{1-6}$-alkyl or $C_{1-6}$-alkoxy each of which can be optionally substituted with carboxy.

15. A compound according to claim 1 wherein Ar is phenylene.

16. A compound according to claim 1 wherein $R_1$ is hydrogen or $R_1$ forms a bond together with $R_2$.

17. A compound according to claim 1 wherein $R_2$ is hydrogen or $R_2$ forms a bond together with $R_1$.

18. A compound according to claim 1 wherein $R_3$ is $C_{1-6}$-alkyl.

19. A compound according to claim 1 wherein $R_4$ is hydrogen.

20. A compound according to claim 1 wherein m is 1.

21. A compound according to claim 1 wherein m is 1.

22. A compound according to claim 1 wherein n is an integer ranging from 1 to 3 and m is 1.

23. A compound according to claim 1 wherein the substituents Z and Y are arranged in a trans-configuration.

24. A compound according to claim 1 wherein the substituents Z and Y are arranged in a cis-configuration.

25. The compound according to claim 1 which is (E)-(S)-2-Ethoxy-3-[4-(5-phenyl-pent-2-en-4-ynyloxy)-phenyl]-propionic acid ethyl ester, (E)-(S)-2-Ethoxy-3-[4-(5-phenyl-pent-2-en-4-ynyloxy)-phenyl]-propionic acid, (Z)-(S)-2-Ethoxy-3-[4-(3-methyl-5-phenyl-pent-2-en-4-ynyloxy)-phenyl]-propionic acid ethyl ester, (Z)-(S)-2-Ethoxy-3-[4-(3-methyl-5-phenyl-pent-2-en-4-ynyloxy)-phenyl]-propionic acid, (E)-(S)-2-Ethoxy-3-[4-(3-methyl-5-phenyl-pent-2-en-4-ynyloxy)-phenyl]-propionic acid ethyl ester, (E)-(S)-2-Ethoxy-3-[4-(3-methyl-5-phenyl-pent-2-en-4-ynyloxy)-phenyl]-propionic acid;

or a pharmaceutically acceptable salt thereof.

26. The compound according to claim 1 which is

Ethyl (E)-(S)-2-ethoxy-3-[4-(3-methyl-5-(3,5-dichloro-phenyl)-pent-2-en-4-ynyloxy)-phenyl]-propionate, (E)-(S)-2-ethoxy-3-[4-(3-methyl-5-(3,5-dichloro-phenyl)-pent-2-en-4-ynyloxy)-phenyl]-propionic acid, Ethyl (Z)-(S)-2-ethoxy-3-[4-(3-methyl-5-(3,5-dichloro-phenyl)-pent-2-en-4-ynyloxy)-phenyl]-propionate, (Z)-(S)-2-ethoxy-3-[4-(3-methyl-5-(3,5-dichloro-phenyl)-pent-2-en-4-ynyloxy)-phenyl]propionic acid, Ethyl (E)-(S)-2-ethoxy-3-[4-(3-methyl-5-(3-trifluoromethyl-phenyl)-pent-2-en-4-ynyloxy)-phenyl]-propionate, (E)-(S)-2-ethoxy-3-[4-(3-methyl-5-(3-trifluoromethyl-phenyl)-pent-2-en-4-ynyloxy)-phenyl]-propionic acid, Ethyl (Z)-(S)-2-ethoxy-3-[4-(3-methyl-5-(3-trifluoromethyl-phenyl)-pent-2-en-4-ynyloxy)phenyl]-propionate, (Z)-(S)-2-ethoxy-3-[4-(3-methyl-5-(3-trifluoromethyl-phenyl)-pent-2-en-4-ynyloxy]-phenyl-propionic acid;

or a pharmaceutically acceptable salt thereof.

27. The compound according to claim 1 which is

Ethyl (E)-(S)-2-ethoxy-3-[4-(3-methyl-5-(1-naphthyl)-pent-2-en-4-ynyloxy)-phenyl]-propionate, (E)-(S)-2-ethoxy-3-[4-(3-methyl-5-(1-naphthyl)-pent-2-en-4-ynyloxy)-phenyl]-propionic acid, Ethyl (Z)-(S)-2-ethoxy-3-[4-(3-methyl-5-(1-naphthyl)-pent-2-en-4-ynyloxy)-phenyl]-propionate, (Z)-(S)-2-ethoxy-3-[4-(3-methyl-5-(1-naphthyl)-pent-2-en-4-ynyloxy)-phenyl]-propionic acid, Ethyl (E)-(S)-2-ethoxy-3-[4-(-5-(3,5-dichloro-phenyl)-pent-2-en-4-ynyloxy)-phenyl]-propionate, (E)-(S)-2-ethoxy-3-[4-(5-(3,5-dichloro-phenyl)-pent-2-en-4-ynyloxy)-phenyl]-propionic acid, Ethyl (Z)-(S)-2-ethoxy-3-[4-(3-methyl-5-(3,5-dichloro-phenyl)-pent-2-en-4-ynyloxy)phenyl]-propionate, (Z)-(S)-2-ethoxy-3-[4-(3-methyl-5-(3,5-dichloro-phenyl)-pent-2-en-4-ynyloxy)-phenyl]-propionic acid;

or a pharmaceutically acceptable salt thereof.

28. The compound according to claim 1 which is (Z)-(S)-2-Ethoxy-3-[4-(5-phenyl-pent-2-en-4-ynyloxy)-phenyl]-propionic acid ethyl ester, (Z)-(S)-2-Ethoxy-3-[4-(5-phenyl-pent-2-en-4-ynyloxy)-phenyl]-propionic acid, (E)-(RS)-2-Ethoxy-3-[3-(5-phenyl-pent-2-en-4-ynyloxy)-phenyl]-propionic acid ethyl ester;

or a pharmaceutically acceptable salt thereof.

29. The compound according to claim 1 which is (E)-(S)-3-{4-[5-(1,3-Difluoro-phenyl)-pent-2-en-4-ynyloxy]-phenyl}-2-ethoxy-propionic acid, (E)-(S)-3-{4-[5-(1,3-Dibromo-phenyl)-pent-2-en-4-ynyloxy]-phenyl}-2-ethoxy-propionic acid, (E)-(S)-3-{4-[5-(1,3-Diiodo-phenyl)-pent-2-en-4-ynyloxy]-phenyl}-2-ethoxy-propionic acid, (E)-(S)-3-{4-[5-(1,3-Bis-trifluoromethyl-phenyl)-pent-2-en-4-ynyloxy]-phenyl}-2-ethoxy-propionic acid, (E)-(S)-3-{4-[5-(1,3-Dimethoxy-phenyl)-pent-2-en-4-ynyloxy]-phenyl}-2-ethoxy-propionic acid, (E)-(S)-3-{4-[5-(1,3-Diethoxy-phenyl)-pent-2-en-4-ynyloxy]-phenyl}-2-ethoxy-propionic acid, (E)-(S)-3-{4-[5-(1,3-Bis-(2,2,2-trifluoromethoxy)-phenyl)-pent-2-en-4-ynyloxy]-phenyl}-2-ethoxy-propionic acid, (E)-(S)-3-{4-[5-(1,3-Bis-(2,2,2-trifluoroethoxy)-phenyl)-pent-2-en-4-ynyloxy]-phenyl}-2-ethoxy-propionic acid, (E)-(S)-3-{4-[5-(3,5-Difluoro-phenyl)-pent-2-en-4-ynyloxy]-phenyl}-2-ethoxy-propionic acid, (E)-(S)-3-{4-[5-(3,5-Dibromo-phenyl)-pent-2-en-4-ynyloxy]-phenyl}-2-ethoxy-propionic acid, (E)-(S)-3-{4-[5-(3,5-Diiodo-phenyl)-pent-2-en-4-ynyloxy]-phenyl}-2-ethoxy-propionic acid, (E)-(S)-3-{4-[5-(3,5-Bis-trifluoromethyl-phenyl)-pent-2-en-4-ynyloxy]-phenyl}-2-ethoxy-propionic acid, (E)-(S)-3 -{4-[5-(3,5-Dimethoxy-phenyl)-pent-2-en-4-ynyloxy]-phenyl}-2-ethoxy-propionic acid.

(E)-(S)-3-{4-[5-(3,5-Diethoxy-phenyl)-pent-2-en-4-ynyloxy]-phenyl}-2-ethoxy-propionic acid, (E)-(S)-3-{4-[5-(3,5-Bis-(2,2,2-trifluoromethoxy)-phenyl)-pent-2-en-4-ynyloxy]-phenyl}-2-ethoxy-propionic acid, (E)-(S)-3-{4-[5-(3,5-Bis-(2,2,2-trifluoroethoxy)-phenyl)-pent-2-en-4-ynyloxy]-phenyl}-ethoxy-propionic acid, (E)-(S)-3-{4-[5-(1,3-Difluoro-phenyl)-3-methyl-pent-2-en-4-ynyloxy]-phenyl}-2-ethoxy-propionic acid, (E)-(S)-3-{4-[5-(1,3-Dibromo-phenyl)-3-methyl-pent-2-en-4-ynyloxy]-phenyl}-2-ethoxy-propionic acid, (E)-(S)-3-{4-[5-(1,3-Diiodo-phenyl)-3-methyl-pent-2-en-4-ynyloxy]-phenyl}-2-ethoxy-propionic acid, (E)-(S)-3-{4-[5-(1,3-Bis-trifluoromethyl-phenyl)-3-methyl-pent-2-en-4-ynyloxy]-phenyl}-2-ethoxy-propionic acid, (E)-(S)-3-{4-[5-(1,3-Dimethoxy-phenyl)-pent-2-en-4-ynyloxy]-phenyl}-3-methyl-2-ethoxy-propionic acid, (E)-(S)-3-{4-[5-(1,3-Diethoxy-phenyl)-3-methyl-pent-2-en-4-ynyloxy]-phenyl}-2-ethoxy-propionic acid, (E)-(S)-3-{4-[5-(1,3-Bis-(2,2,2-trifluoromethoxy)-phenyl)-3-methyl-pent-2-en-4-ynyloxy]-phenyl}-2-ethoxy-propionic acid, (E)-(S)-3-{4-[5-(1,3-Bis-(2,2,2-trifluoroethoxy)-phenyl)-3-methyl-pent-2-en-4-ynyloxy]-phenyl}-2-ethoxy-propionic acid, (E)-(S)-3-{4-[5-(3,5-Difluoro-phenyl)-3-methyl-pent-2-en-4-ynyloxy]-phenyl}-2-ethoxy-propionic acid, (E)-(S)-3-{4-[5-(3,5-Dibromo-phenyl)-3-methyl-pent-2-en-4-ynyloxy]-phenyl}-2-ethoxy-propionic acid, (E)-(S)-3-{4-[5-(3,5-Diiodo-phenyl)-3-methyl-pent-2-en-4-ynyloxy]-phenyl}-2-ethoxy-propionic acid, (E)-(S)-3-{4-[5-(3,5-Bis-trifluoromethyl-phenyl)-3-methyl-pent-2-en-4-ynyloxy]-phenyl}-2-ethoxy-propionic acid, (E)-(S)-3-{4-[5-(3,5-Dimethoxy-phenyl)-methyl-pent-2-en-4-ynyloxy]-phenyl}-2-ethoxy-propionic acid, (E)-(S)-3-{4-[5-(3,5-Diethoxy-phenyl)-3-methyl-pent-2-en-4-ynyloxy]-phenyl}-2-ethoxy-propionic acid, (E)-(S)-3-{4-[5-(3,5-Bis-(2,2,2-trifluoromethoxy)-phenyl)-3-methyl-pent-2-en-4-ynyloxy]-phenyl}-2-ethoxy-propionic acid, (E)-(S)-3-{4-[5-(3,5-Bis-(2,2,2-trifluoroethoxy)-phenyl)-3-methyl-pent-2-en-4-ynyloxy]-phenyl}-2-ethoxy-propionic acid,
(E)-(S)-3-{4-[5-(1,3-Difluoro-phenyl)-pent-2-en-4-ynyloxy]-3-chloro-phenyl}-2-ethoxy-propionic acid,
(E)-(S)-3-{4-[5-(1,3-Dibromo-phenyl)-pent-2-en-4-ynyloxy]-3-chloro-phenyl}-2-ethoxy-propionic acid,
(E)-(S)-3-{4-[5-(1,3-Diiodo-phenyl)-pent-2-en-4-ynyloxy]-3-chloro-phenyl}-2-ethoxy-propionic acid,
(E)-(S)-3-{4-[5-(1,3-Bis-trifluoromethyl-phenyl)-pent-2-en-4-ynyloxy]-3-chloro-phenyl}-2-ethoxy-propionic acid,
(E)-(S)-3-{4-[5-(3-Dimethoxy-pheny)-pent-2-en-4-ynyloxy]-chloro-phenyl}-2-ethoxy-propionic acid,
(E)-(S)-3-{4-[5-(1,3-Diethoxy-phenyl)-pent-2-en-4-ynyloxy]-3-chloro-phenyl}-2-ethoxy-propionic acid,
(E)-(S)-3-{4-[5-(3-Bis-(2,2,2-trifluoromethoxy)-phenyl)-pent-2-en-4-ynyloxy]-3-chloro-phenyl}-2-ethoxy-propionic acid,
(E)-(S)-3-{4-[5-(1,3-Bis-(2,2,2-trifluoroethoxy)-phenyl)-pent-2-en-4-ynyloxy]-3-chloro-phenyl}-2-ethoxy-propionic acid,
(E)-(S)-3-{4-[5-(3,5-Difluoro-phenyl)-pent-2-en-4-ynyloxy]-3-chloro-phenyl}-2-ethoxy-propionic acid,
(E)-(S)-3-{4-[5-(3,5-Dibromo-phenyl)-pent-2-en-4-ynyloxy]-3-chloro-phenyl}-2-ethoxy-propionic acid,
(E)-(S)-3-{4-[5-(3,5-Diiodo-phenyl)-pent-2-en-4-ynyloxy]-3-chloro-phenyl}-2-ethoxy-propionic acid,
(E)-(S)-3-{4-[5-(3,5-Bis-trifluoromethyl-phenyl)-pent-2-en-4-ynyloxy]-3-chloro-phenyl}-2-ethoxy-propionic acid,
(E)-(S)-3-{4-[5-(3,5-Dimethoxy-phenyl)-pent-2-en-4-ynyloxy]-3-chloro-phenyl}-2-ethoxy-propionic acid,
(E)-(S)-3-4-[5-(3,5-Diethoxy-phenyl)-pent-2-en-4-ynyloxy]-3-chloro-phenyl-3-2-ethoxy-propionic acid,
(E)-(S)-3-{4-[5-(3,5-Bis-(2,2,2-trifluoromethoxy)-phenyl)-pent-2-en-4-ynyloxy]-3-chloro-phenyl}-2-ethoxy-propionic acid,
(E)-(S)-3-{4-[5-(3,5-Bis-(2,2,2-trifluoroethoxy)-pheny)-pent-2-en-4-ynyloxy]-3-chloro-phenyl}-2-ethoxy-propionic acid,
(E)-(S)-3-{4-[5-(1,3-Difluoro-phenyl)-3-methyl-pent-2-en-4-ynyloxy]-3-chloro-phenyl}-2-ethoxy-propionic acid,
(E)-(S)-3-{4-[5-(1,3-Dibromo-phenyl)-3-methyl-pent-2-en-4-ynyloxy]-3-chloro-phenyl}-2-ethoxy-propionic acid,
(E)-(S)-3-{4-[5-(1,3-Diiodo-phenyl)-3-methyl-pent-2-en-4-ynyloxy]-3-chloro-phenyl}-2-ethoxy-propionic acid,
(E)-(S)-3-{4-[5-(1,3-Bis-trifluoromethyl-phenyl)-3-methyl-pent-2-en-4-ynyloxy]-3-chloro-phenyl}-2-ethoxy-propionic acid,
(E)-(S)-3-{4-[5-(1,3-Diimethoxy-phenyl)-pent-2-en-4-ynyloxy]-3-chloro-phenyl}-3-methyl-2-ethoxy-propionic acid,
(E)-(S)-3-{4-[5-(1,3-Diethoxy-phenyl)-3-methyl-pent-2-en-4-ynyloxy]-3-chloro-phenyl}-2-ethoxy-propionic acid,
(E)-(S)-3-{4-[5-(1,3-Bis-(2,2,2-trifluoromethoxy)-phenyl)-3-methyl-pent-2-en-4-ynyloxy]-3-chloro-phenyl}-2-ethoxy-propionic acid,
(E)-(S)-3-{4-[5-(1,3-Bis-(2,2,2-trifluoroethoxy)-phenyl)-3-methyl-pent-2-en-4-ynyloxy]-3-chloro-phenyl}-2-ethoxy-propionic acid,
(E)-(S)-3-{4-[5-(3,5-Difluoro-phenyl)-3-methyl-pent-2-en-4-ynyloxy]-3-chloro-phenyl}-2-ethoxy-propionic acid,
(E)-(S)-3-{4-[5-(3,5-Dibromo-phenyl)-3-methyl-pent-2-en-4-ynyloxy]-3-chloro-phenyl}-2-ethoxy-propionic acid,
(E)-(S)-3-{4-[5-(3,5-Diiodo-phenyl)-3-methyl-pent-2-en-4-ynyloxy]-3-chloro-phenyl}-2-ethoxy-propionic acid,
(E)-(S)-3-{4-[5-(3,5-Bis-trifluoromethyl-phenyl)-3-methyl-pent-2-en-4-ynyloxy]-3-chloro-phenyl}-2-ethoxy-propionic acid,
(E)-(S)-3-4-[5-(3,5-Dimethoxy-phenyl)-3-methyl-pent-2-en-4-ynyloxy]-3-chloro-phenyl}-2-ethoxy-propionic acid,
(E)-(S)-3-{4-[5-(3,5-Diethoxy-phenyl)-3-methyl-pent-2-en-4-ynyloxy]-3-chloro-phenyl}-2-ethoxy-propionic acid,
(E)-(S)-3-{4-[5-(3,5-Bis-(2,2,2-trifluoromethoxy)-phenyl)-3-methyl-pent-2-en-4-ynyloxy]-3-chloro-phenyl}-2-ethoxy-propionic acid,
(E)-(S)-3-{4-[5-(3,5-Bis-(2,2,2-trifluoroethoxy)-phenyl)-3-methyl-pent-2-en-4-ynyloxy]-3-chloro-phenyl}-2-ethoxy-propionic acid,
(E)-(S)-3-{4-[5-(1,3-Difluoro-phenyl)-pent-2-en-4-ynyloxy]-3-bromo-pheny}-2-ethoxy-propionic acid,
(E)-(S)-3-{4-[5-(1,3-Dibromo-phenyl)-pent-2-en-4-ynyloxy]-3-bromo-phenyl}-2-ethoxy-propionic acid,
(E)-(S)-3-{4-[5-(1,3-Diiodo-phenyl)-pent-2-en-4-ynyloxy]-3-bromo-phenyl}-2-ethoxy-propionic acid,
(E)-(S)-3-{4-[5-(1,3-Bis-trifluoromethyl-phenyl)-pent-2-en-4-ynyloxy]-3-bromo-phenyl}-2-ethoxy-propionic acid,
(E)-(S)-3-{4-[5-(1,3-Dimethoxy-phenyl)-pent-2-en-4-ynyloxy]-3-bromo-phenyl}-2-ethoxy-propionic acid,
(E)-(S)-3-{4-[5-(1,3-Diethoxy-phenyl)-pent-2-en-4-ynyloxy]-3-bromo-phenyl}-2-ethoxy-propionic acid,
(E)-(S)-3-{4-[5-(1,3-Bis-(2,2,2-trifluoromethoxy)-phenyl)-pent-2-en-4-ynyloxy]-3-bromo-phenyl}-2-ethoxy-propionic acid,
(E)-(S)-3-{4-[5-(1,3-Bis-(2,2,2-trifluoroethoxy)-phenyl)-pent-2-en-4-ynyloxy]-3-bromo-phenyl}-2-ethoxy-propionic acid,
(E)-(S)-3-{4-[5-(3,5-Difluoro-phenyl)-pent-2-en-4-ynyloxy]-3-bromo-phenyl}-2-ethoxy-propionic acid,
(E)-(S)-3-{4-[5-(3,5-Dibromo-phenyl)-pent-2-en-4-ynyloxy]-3-bromo-phenyl}-2-ethoxy-propionic acid,
(E)-(S)-3-{4-[5-(3,5-Diiodo-phenyl)-pent-2-en-4-ynyloxy]-3-bromo-phenyl}-2-ethoxy-propionic acid,
(E)-(S)-3-{4-[5-(3,5-Bis-trifluoromethyl-phenyl)-pent-2-en-4-ynyloxy]-3-bromo-phenyl}-2-ethoxy-propionic acid,
(E)-(S)-3-{4-[5-(3,5-Diimethoxy-phenyl)-pent-2-en-4-ynyloxy]-3-bromo-phenyl}-2-ethoxy-propionic acid,
(E)-(S)-3-{4-[5-(3,5-Diethoxy-phenyl)-pent-2-en-4-ynyloxy]-3-bromo-phenyl}-2-ethoxy-propionic acid,
(E)-(S)-3-{4-[5-(3,5-Bis-(2,2,2-trifluoromethoxy)-pheny)-pent-2-en-4-ynyloxy]-3-bromo-phenyl}-2-ethoxy-propionic acid,
(E)-(S)-3-{4-[5-(3,5-Bis-(2,2,2-trifluoroethoxy)-phenyl)-pent-2-en-4-ynyloxy]-3-bromo-phenyl}-2-ethoxy-propionic acid,
(E)-(S)-3-{4-[5-(1,3-Difluoro-phenyl)-3-methyl-pent-2-en-4-ynyloxy]-3-bromo-phenyl}-2-ethoxy-propionic acid, (E)-(S)-3-{4-[5-(1,3-Dibromo-phenyl)-3-methyl-pent-2-en-4-ynyloxy]-3-bromo-phenyl}-2-ethoxy-propionic acid, (E)-(S)-3-{4-[5-(1,3-Diiodo-phenyl)-3-methyl-pent-2-en-4-ynyloxy]-3-bromo-phenyl}-2-ethoxy-propionic acid, (E)-(S)-3-{4-[5-(1,3-Bis-trifluoromethyl-phenyl)-3-methyl-pent-2-en-4-ynyloxy]-3-bromo-phenyl}-2-ethoxy-propionic acid, (E)-(S)-3-{4-[5-(1,3-Dimethoxy-phenyl)-pent-2-en-4-ynyloxy]-3-bromo-phenyl}-3-methyl-2-ethoxy-propionic acid, (E)-(S)-3-{4-[5-(1,3-Diethoxy-phenyl)-3-methyl-pent-2-en-4-ynyloxy]-3-bromo-phenyl}-2-ethoxy-propionic acid, (E)-(S)-3-{4-[5-(1,3-Bis-(2,2,2-trifloromethoxy)-phenyl)-3-methyl-pent-2-en-4-ynyloxy]-3-bromo-phenyl}-2-ethoxy-propionic acid, (E)-(S)-3-{4-[5-(1,3-Bis-(2,2,2-trifluoroethoxy)-phenyl)-3-methyl-pent-2-en-4-ynyloxy]-3-bromo-phenyl}-2-ethoxy-propionic acid, (E)-(S)-3-{4-[5-(3,5-Difluoro-phenyl)-3-methyl-pent-2-en-4-ynyloxy]-3-bromo-phenyl}-2-ethoxy-propionic acid, (E)-(S)-3-{4-[5-(3,5-Dibromo-phenyl)-3-methyl-pent-2-en-4-ynyloxy]-3-bromo-phenyl}-2-ethoxy-propionic acid, (E)-(S)-3-{4-[5-(3,5-Diiodo-phenyl)-3-methyl-pent-2-en-4-ynyloxy]-3-bromo-phenyl}-2-ethoxy-propionic acid, (E)-(S)-3-{4-[5-(1,5-Bis-trifluoromethyl-phenyl)-3-methyl-pent-2-en-4-ynyloxy]-3-bromo-phenyl}-2-ethoxy-propionic acid, 2-ethoxy-propionic acid, (E)-(S)-3-{4-[5-(3,5-Dimethoxy-phenyl)-3-methyl-phenyl-pent-2-en-4-ynyloxy]-3-bromo-phenyl}-2-ethoxy-propionic acid, (E)-(S)-3-{4-[5-(3,5-Diethoxy-phenyl)-3-methyl-pent-2-en-4-ynyloxy]-3-bromo-phenyl}-2-ethoxy-propionic acid, (E)-(S)-3-{4-[5-(3,5-Bis-(2,2,2-trifluoromethoxy)-phenyl)-3-methyl-pent-2-en-4-ynyloxy]-3-bromo-phenyl}-2-ethoxy-propionic acid, (E)-(S)-3-{4-[5-(3,5-Bis-(2,2,2-trifluoroethoxy)-phenyl)-3-methyl-pent-2-en-4-ynyloxy]-3-bromo-phenyl}-2-ethoxy-propionic acid, (E)-(S)-3-{4-[5-(1,3-Difluoro-phenyl)-pent-2-en-4-ynyloxy]-3-iodo-phenyl}-2-ethoxy-propionic acid, (E)-(S)-3-{4-[5-(1,3-Dibromo-phenyl)-pent-2-en-4-ynyloxy]-3-iodo-phenyl}-2-ethoxy-propionic acid, (E)-(S)-3-{4-[5-(1,3-Diiodo-phenyl)-pent-2-en-4-ynyloxy]-3-iodo-phenyl}-2-ethoxy-propionic acid, (E)-(S)-3-{4-[5-(1,3-Bis-trifluoromethyl-phenyl)-pent-2-en-4-ynyloxy]-3-iodo-phenyl}-2-ethoxy-propionic acid, (E)-(S)-3-{4-[5-(1,3-Dimethoxy-phenyl)-pent-2-en-4-ynyloxy]-3-iodo-phenyl}-2-ethoxy-propionic acid, (E)-(S)-3-{4-[5-(1,3-Diethoxy-phenyl)-pent-2-en-4-ynyloxy]-3-iodo-phenyl}-2-ethoxy-propionic acid, (E)-(S)-3-{4-[5-(1,3-Bis-(2,2,2-trifluoromethoxy)-phenyl)-pent-2-en-4-ynyloxy]-3-iodo-phenyl}-2-ethoxy-propionic acid, (E)-(S)-3-{4-[5-(1,3-Bis-(2,2,2-trifluoroethoxy)-phenyl)-pent-2-en-4-ynyloxy]-3-iodo-phenyl}-2-ethoxy-propionic acid, (E)-(S)-3-{4-[5-(3,5-Difluoro-phenyl)-pent-2-en-4-ynyloxy]-3-iodo-phenyl}-2-ethoxy-propionic acid, (E)-(S)-3-{4-[5-(3,5-Dibromo-phenyl)-pent-2-en-4-ynyloxy]-3-iodo-phenyl}-2-ethoxy-propionic acid, (E)-(S)-3-{4-[5-(3,5-Diiodo-phenyl)-pent-2-en-4-ynyloxy]-3-iodo-phenyl}-2-ethoxy-propionic acid, (E)-(S)-3-{4-[5-(3,5-Bis-trifluoromethyl-phenyl)-pent-2-en-4-ynyloxy]-3-iodo-phenyl}-2-ethoxy-propionic acid, (E)-(S)-3-{4-[5-(3,5-Dimethoxy-phenyl)-pent-2-en-4-ynyloxy]-3-iodo-phenyl}-2-ethoxy-propionic acid, (E)-(S)-3-{4-[5-(3,5-Diethoxy-phenyl)-pent-2-en-4-ynyloxy]-3-iodo-phenyl}-2-ethoxy-propionic acid, (E)-(S)-3-{4-[5-(3,5-Bis-(2,2,2-trifluoromethoxy)-phenyl)-pent-2-en-4-ynyloxy]-3-iodo-phenyl}-2-ethoxy-propionic acid, (E)-(S)-3-{4-[5-(3,5-Bis-(2,2,2-trifluoroethoxy)-phenyl)-pent-2-en-4-ynyloxy]-3-iodo-phenyl}-2-ethoxy-propionic acid, (E)-(S)-3-{4-[5-(1,3-Difluoro-phenyl)-3-methyl-pent-2-en-4-ynyloxy]-3-iodo-phenyl}-2-ethoxy-propionic acid, (E)-(S)-3-{4-[5-(1,3-Dibromo-phenyl)-3-methyl-pent-2-en-4-ynyloxy]-3-iodo-phenyl}-2-ethoxy-propionic acid, (E)-(S)-3-{4-[5-(1,3-Diiodo-phenyl)-3-methyl-pent-2-en-4-ynyloxy]-3-iodo-phenyl}-2-ethoxy-propionic acid, (E)-(S)-3-{4-[5-(1,3-Bis-trifluoromethyl-phenyl)-3-methyl-pent-2-en-4-ynyloxy]-3-iodo-phenyl}-2-ethoxy-propionic acid, (E)-(S)-3-{4-[5-(1,3-Dimethoxy-phenyl)-pent-2-en-4-ynyloxy]-3-iodo-phenyl}-3-methyl-2-ethoxy-propionic acid, (E)-(S)-3-{4-[5-(1,3-Diethoxy-phenyl)-3-methyl-pent-2-en-4-ynyloxy]-3-iodo-phenyl}-2-ethoxy-propionic acid, (E)-(S)-3-{4-[5-(1,3-Bis-(2,2,2-trifluoromethoxy)-phenyl)-3-methyl-pent-2-en-4-ynyloxy]-3-iodo-phenyl}-2-ethoxy-propionic acid, (E)-(S)-3-{4-[5-(1,3-Bis-(2,2,2-trifluoroethoxy)-phenyl)-3-methyl-pent-2-en-4-ynyloxy]-3-iodo-phenyl}-2-ethoxy-propionic acid, (E)-(S)-3-{4-[5-(3,5-Difluoro-phenyl)-3-methyl-pent-2-en-4-ynyloxy]-3-iodo-phenyl}-2-ethoxy-propionic acid, (E)-(S)-3-{4-[5-(3,5-Dibromo-phenyl)-3-methyl-pent-2-en-4-ynyloxy]-3-iodo-phenyl}-2-ethoxy-propionic acid, (E)-(S)-3-{4-[5-(3,5-Diiodo-phenyl)-3-methyl-pent-2-en-4-ynyloxy]-3-iodo-phenyl}-2-ethoxy-propionic acid, (E)-(S)-3-{4-[5-(3,5-Bis-trifluoromethyl-phenyl)-3-methyl-pent-2-en-4-ynyloxy]-3-iodo-phenyl}-2-ethoxy-propionic acid, (E)-(S)-3-{4-[5-(3,5-Dimethoxy-phenyl)-3-methyl-pent-2-en-4-ynyloxy]-3-iodo-phenyl}-2-ethoxy-propionic acid, (E)-(S)-3-{4-[5-(3,5-Diethoxy-phenyl)-3-methyl-pent-2-en-4-ynyloxy]-3-iodo-phenyl}-2-ethoxy-propionic acid, (E)-(S)-3-{4-[5-(3,5-Bis-(2,2,2-trifluoromethoxy)-phenyl)-3-methyl-pent-2-en-4-ynyloxy]-3-iodo-phenyl}-2-ethoxy-propionic acid, (E)-(S)-3-{4-[5-(3,5-Bis-(2,2,2-trifluoroethoxy)-phenyl)-3-methyl-pent-2-en-4-ynyloxy]-3-iodo-phenyl}-2-ethoxy-propionic acid;

or a pharmaceutically acceptable salt thereof.

30. The compound according to claim 1 which is
(Z)-(S)-3-{4-[5-(1,3-Difluoro-phenyl)-pent-2-en-4-ynyloxy]-phenyl}-2-ethoxy-propionic acid,
(Z)-(S)-3-{4-[5-(1,3-Dibromo-phenyl)-pent-2-en-4-ynyloxy]-phenyl}-2-ethoxy-propionic acid,
(Z)-(S)-3-{4-[5-(1,3-Diiodo-phenyl)-pent-2-en-4-ynyloxy]-phenyl}-2-ethoxy-propionic acid,
(Z)-(S)-3-{4-[5-(1,3-Bis-trifluoromethyl-phenyl)-pent-2-en-4-ynyloxy]-phenyl}-2-ethoxy-propionic acid,
(Z)-(S)-3-{4-[5-(1,3-Dimethoxy-phenyl)-pent-2-en-4-ynyloxy]-phenyl}-2-ethoxy-propionic acid,
(Z)-(S)-3-{4-[5-(1,3-Diethoxy-phenyl)-pent-2-en-4-ynyloxy]-phenyl}-2-ethoxy-propionic acid,
(Z)-(S)-3-{4-[5-(1,3-Bis-(2,2,2-trifluoromethoxy)-phenyl)-pent-2-en-4-ynyloxy]-phenyl}-2-ethoxy-propionic acid,
(Z)-(S)-3-{4-[5-(1,3-Bis-(2,2,2-trifluoroethoxy)-phenyl)-pent-2-en-4-ynyloxy]-phenyl}-2-ethoxy-propionic acid,
(Z)-(S)-3-{4-[5-(3,5-Difluoro-phenyl)-pent-2-en-4-ynyloxy]-phenyl}-2-ethoxy-propionic acid,
(Z)-(S)-3-{4-[5-(3,5-Dibromo-phenyl)-pent-2-en-4-ynyloxy]-phenyl}-2-ethoxy-propionic acid,
(Z)-(S)-3-{4-[5-(3,5-Diiodo-phenyl)-pent-2-en-4-ynyloxy]-phenyl}-2-ethoxy-propionic acid,
(Z)-(S)-3-{4-[5-(3,5-Bis-trifluoromethyl-phenyl)-pent-2-en-4-ynyloxy]-phenyl}-2-ethoxy-propionic acid,
(Z)-(S)-3-{4-[5-(3,5-Dimethoxy-phenyl)-pent-2-en-4-ynyloxy]-phenyl}-2-ethoxy-propionic acid,
(Z)-(S)-3-{4-[5-(3,5-Diethoxy-phenyl)-pent-2-en-4-ynyloxy]-phenyl}-2-ethoxy-propionic acid,
(Z)-(S)-3-{4-[5-(3,5-Bis-(2,2,2-trifluoromethoxy)-phenyl)-pent-2-en-4-ynyloxy]-phenyl}-2-ethoxy-propionic acid,
(Z)-(S)-3-{4-[5-(3,5-Bis-(2,2,2-trifluoroethoxy)-phenyl)-pent-2-en-4-ynyloxy]-phenyl}-2-ethoxy-propionic acid,
(Z)-(S)-3-{4-[5-(1,3-Difluoro-phenyl)-3-methyl-pent-2-en-4-ynyloxy]-phenyl}-2-ethoxy-propionic acid,
(Z)-(S)-3-{4-[5-(1,3-Dibromo-phenyl)-3-methyl-pent-2-en-4-ynyloxy]-phenyl}-2-ethoxy-propionic acid,
(Z)-(S)-3-{4-[5-(1,3-Diiodo-phenyl)-3-methyl-pent-2-en-4-ynyloxy]-phenyl}-2-ethoxy-propionic acid,
(Z)-(S)-3-{4-[5-(1,3-Bis-trifluoromethyl-phenyl)-3-methyl-pent-2-en-4-ynyloxy]-phenyl}-2-ethoxy-propionic acid,
(Z)-(S)-3-{4-[5-(1,3-Dimethoxy-phenyl)-pent-2-en-4-ynyloxy]-phenyl}-3-methyl-2-ethoxy-propionic acid,
(Z)-(S)-3-{4-[5-(1,3-Diethoxy-phenyl)-3-methyl-pent-2-en-4-ynyloxy]-phenyl}-2-ethoxy-propionic acid,
(Z)-(S)-3-{4-[5-(1,3-Bis-(2,2,2-trifluoromethoxy)-phenyl)-3-methyl pent-2-en-4-ynyloxy]-phenyl}-2-ethoxy-propionic acid,
(Z)-(S)-3-{4-[5-(1,3-Bis-(2,2,2-trifluoroethoxy)-phenyl)-3-methyl-pent-2-en-4-ynyloxy]-phenyl}-2-ethoxy-propionic acid,
(Z)-(S)-3-{4-[5-(3,5-Difluoro-phenyl)-3-methyl-pent-2-en-4-ynyloxy]-phenyl}-2-ethoxy-propionic acid,
(Z)-(S)-3-{4-[5-(3,5-Dibromo-phenyl)-3-methyl-pent-2-en-4-ynyloxy]-phenyl}-2-ethoxy-propionic acid,
(Z)-(S)-3-{4-[5-(3,5-Diiodo-phenyl)-3-methyl-pent-2-en-4-ynyloxy]-phenyl}-2-ethoxy-propionic acid,
(Z)-(S)-3-{4-[5-(3,5-Bis-trifluoromethyl-phenyl)-3-methyl-pent-2-en-4-ynyloxy]-phenyl}-2-ethoxy-propionic acid,
(Z)-(S)-3-{4-[5-(3,5-Dimethoxy-phenyl)-3-methyl-pent-2-en-4-ynyloxy]-phenyl}-2-ethoxy-propionic acid,
(Z)-(S)-3-{4-[5-(3,5-Diethoxy-phenyl)-3-methyl-pent-2-en-4-ynyloxy]-phenyl}-2-ethoxy-propionic acid,
(Z)-(S)-3-{4-[5-(3,5-Bis-(2,2,2-trifluoromethoxy)-phenyl)-3-methyl-pent-2-en-4-ynyloxy]-phenyl}-2-ethoxy-propionic acid,
(Z)-(S)-3-{4-[5-(3,5-Bis-(2,2,2-trifluoroethoxy)-phenyl)-3-methyl-pent-2-en-4-ynyloxy]-phenyl}-2-ethoxy-propionic acid,
(Z)-(S)-3-{4-[5-(1,3-Difluoro-phenyl)-pent-2-en-4-ynyloxy]-3-chloro-phenyl}-2-ethoxy-propionic acid,
(Z)-(S)-3-{4-[5-(1,3-Dibromo-phenyl)-pent-2-en-4-ynyloxy]-3-chloro-phenyl}-2-ethoxy-propionic acid,
(Z)-(S)-3-{4-[5-(1,3-Diiodo-phenyl)-pent-2-en-4-ynyloxy]-3-chloro-phenyl}-2-ethoxy-propionic acid,
(Z)-(S)-3-{4-[5-(1,3-Bis-trifluoromethyl-phenyl)-pent-2-en-4-ynyloxy]-3-chloro-phenyl}-2-ethoxy-propionic acid,
(Z)-(S)-3-{4-[5-(1,3-Dimethoxy-phenyl)-pent-2-en-4-ynyloxy]-3-chloro-phenyl}-2-ethoxy-propionic acid,
(Z)-(S)-3-{4-[5-(1,3-Diethoxy-phenyl)-pent-2-en-4-ynyloxy]-3-chloro-phenyl}-2-ethoxy-propionic acid,
(Z)-(S)-3-{4-[5-(1,3-Bis-(2,2,2-trifluoromethoxy)-phenyl)-pent-2-en-4-ynyloxy]-3-chloro-phenyl}-2-ethoxy-propionic acid,
(Z)-(S)-3-{4-[5-(1,3-Bis-(2,2,2-trifluoroethoxy)-phenyl)-pent-2-en-4-ynyloxy]-3-chloro-phenyl}-2-ethoxy-propionic acid,
(Z)-(S)-3-{4-[5-(3,5-Difluoro-phenyl)-pent-2-en-4-ynyloxy]-3-chloro-phenyl}-2-ethoxy-propionic acid,
(Z)-(S)-3-{4-[5-(3,5-Dibromo-phenyl)-pent-2-en-4-ynyloxy]-3-chloro-phenyl}-2-ethoxy-propionic acid,
(Z)-(S)-3-{4-[5-(3,5-Diiodo-phenyl)-pent-2-en-4-ynyloxy]-3-chloro-phenyl}-2-ethoxy-propionic acid,
(Z)-(S)-3-{4-[5-(3,5-Bis-trifluoromethyl-phenyl)-pent-2-en-4-ynyloxy]-3-chloro-phenyl}-2-ethoxy-propionic acid,
(Z)-(S)-3-{4-[5-(3,5-Dimethoxy-phenyl)-pent-2-en-4-ynyloxy]-3-chloro-phenyl}-2-ethoxy-propionic acid,
(Z)-(S)-3-{4-[5-(3,5-Diethoxy-phenyl)-pent-2-en-4-ynyloxy]-3-chloro-phenyl}-2-ethoxy-propionic acid,
(Z)-(S)-3-{4-[5-(3,5-Bis-(2,2,2-trifluoromethoxy)-phenyl)-pent-2-en-4-ynyloxy]-3-chloro-phenyl}-2-ethoxy-propionic acid,
(Z)-(S)-3-{4-[5-(3,5-Bis-(2,2,2-trifluoroethoxy)-phenyl)-pent-2-en-4-ynyloxy]-3-chloro-phenyl}-2-ethoxy-propionic acid,
(Z)-(S)-3-{4-[5-(1,3-Difluoro-phenyl)-3-methyl-pent-2-en-4-ynyloxy]-3-chloro-phenyl}-2-ethoxy-propionic acid,
(Z)-(S)-3-{4-[5-(1,3-Dibromo-phenyl)-3-methyl-pent-2-en-4-ynyloxy]-3-chloro-phenyl}-2-ethoxy-propionic acid,
(Z)-(S)-3-{4-[5-(1,3-Diiodo-phenyl)-3-methyl-pent-2-en-4-ynyloxy]-3-chloro-phenyl}-2-ethoxy-propionic acid,
(Z)-(S)-3-{4-[5-(1,3-Bis-trifluoromethyl-phenyl)-3-methyl-pent-2-en-4-ynyloxy]-3-chloro-phenyl}-2-ethoxy-propionic acid,
(Z)-(S)-3-{4-[5-(1,3-Dimethoxy-phenyl)-pent-2-en-4-ynyloxy]-3-chloro-phenyl}-3-methyl-2-ethoxy-propionic acid, (Z)-(S)-3-{4-[5-(1,3-Diethoxy-phenyl)-3-methyl-pent-2-en-4-ynyloxy]-3-chloro-phenyl}-2-ethoxy-propionic acid, (Z)-(S)-3-{4-[5-(1,3-Bis-(2,2,2-trifluoromethoxy)-phenyl)-3-methyl-pent-2-en-4-ynyloxy]-3-chloro-phenyl}-2-ethoxy-propionic acid, (Z)-(S)-3-{4-[5-(1,3-Bis-(2,2,2-trifluoroethoxy)-phenyl)-3-methyl-pent-2-en-4-ynyloxy]-3-chloro-phenyl}-2-ethoxy-propionic acid, (Z)-(S)-3-{4-[5-(3,5-Difluoro-phenyl)-3-methyl-pent-2-en-4-ynyloxy]-3-chloro-phenyl}-2-ethoxy-propionic acid, (Z)-(S)-3-{4-[5-(3,5-Dibromo-phenyl)-3-methyl-pent-2-en-4-ynyloxy]-3-chloro-phenyl}-2-ethoxy-propionic acid, (Z)-(S)-3-{4-[5-(3,5-Diiodo-phenyl)-3-methyl-pent-2-en-4-ynyloxy]-3-chloro-phenyl}-2-ethoxy-propionic acid, (Z)-(S)-3-{4-[5-(3,5-Bis-trifluoromethyl-phenyl)-3-methyl-pent-2-en-4-ynyloxy]-3-chloro-phenyl}-2-ethoxy-propionic acid, (Z)-(S)-3-{4-[5-(3,5-Dimethoxy-phenyl)-3-methyl-pent-2-en-4-ynyloxy]-3-chloro-phenyl}-2-ethoxy-propionic acid, (Z)-(S)-3-{4-[5-(3,5-Diethoxy-phenyl)-3-methyl-pent-2-en-4-ynyloxy]-3-chloro-phenyl}-2-ethoxy-propionic acid, (Z)-(S)-3-{4-[5-(3,5-Bis-(2,2,2-trifluoromethoxy)-phenyl)-3-methyl-pent-2-en-4-ynyloxy]-3-chloro-phenyl}-2-ethoxy-propionic acid, (Z)-(S)-3-{4-[5-(3,5-Bis-(2,2,2-trifluoroethoxy)-phenyl)-3-methyl-pent-2-en-4-ynyloxy]-3-chloro-phenyl}-2-ethoxy-propionic acid, (Z)-(S)-3-{4-[5-(1,3-Difluoro-phenyl)-pent-2-en-4-ynyloxy]-3-bromo-phenyl}-2-ethoxy-propionic acid, (Z)-(S)-3-{4-[5-(1,3-Dibromo-phenyl)-pent-2-en-4-ynyloxy]-3-bromo-phenyl}-2-ethoxy-propionic acid, (Z)-(S)-3-{4-[5-(1,3-Diiodo-phenyl)-pent-2-en-4-ynyloxy]-3-bromo-phenyl}-2-ethoxy-propionic acid, (Z)-(S)-3-{4-[5-(1,3-Bis-trifluoromethyl-phenyl)-pent-2-en-4-ynyloxy]-3-bromo-phenyl}-2-ethoxy-propionic acid, (Z)-(S)-3-{4-[5-(1,3-Dimethoxy-phenyl)-pent-2-en-4-ynyloxy]-3-bromo-phenyl}-2-ethoxy-propionic acid, (Z)-(S)-3-{4-[5-(1,3-Diethoxy-phenyl)-pent-2-en-4-ynyloxy]-3-bromo-phenyl}-2-ethoxy-propionic acid, (Z)-(S)-3-{4-[5-(1,3-Bis-(2,2,2-trifluoromethoxy)-phenyl)-pent-2-en-4-ynyloxy]-3-bromo-phenyl}-2-ethoxy-propionic acid, (Z)-(S)-3-{4-[5-(1,3-Bis-(2,2,2-trifluoroethoxy)-phenyl)-pent-2-en-4-ynyloxy]-3-bromo-phenyl}-2-ethoxy-propionic acid, (Z)-(S)-3-{4-[5-(3,5-Difluoro-phenyl)-pent-2-en-4-ynyloxy]-3-bromo-phenyl}-2-ethoxy-propionic acid, (Z)-(S)-3-{4-[5-(3,5-Dibromo-phenyl)-pent-2-en-4-ynyloxy]-3-bromo-phenyl}-2-ethoxy-propionic acid, (Z)-(S)-3-{4-[5-(3,5-Diiodo-phenyl)-pent-2-en-4-ynyloxy]-3-bromo-phenyl}-2-ethoxy-propionic acid, (Z)-(S)-3-{4-[5-(3,5-Bis-trifluoromethyl-phenyl)-pent-2-en-4-ynyloxy]-3-bromo-phenyl}-ethoxy-propionic acid, (Z)-(S)-3-{4-[5-(3,5-Dimethoxy-phenyl)-pent-2-en-4-ynyloxy]-3-bromo-phenyl}-2-ethoxy-propionic acid, (Z)-(S)-3-{4-[5-(3,5-Diethoxy-phenyl)-pent-2-en-4-ynyloxy]-3-bromo-phenyl}-2-ethoxy-propionic acid, (Z)-(S)-3-{4-[5-(3,5-Bis-(2,2,2-trifluoromethoxy)-phenyl)-pent-2-en-4-ynyloxy]-3-bromo-phenyl}-2-ethoxy-propionic acid, (Z)-(S)-3-{4-[5-(3,5-Bis-(2,2,2-trifluoroethoxy)-phenyl)-pent-2-en-4-ynyloxy]-3-bromo-phenyl}-2-ethoxy-propionic acid, (Z)-(S)-3-{4-[5-(1,3-Difluoro-phenyl)-3-methyl-pent-2-en-4-ynyloxy]-3-bromo-phenyl}-2-ethoxy-propionic acid, (Z)-(S)-3-{4-[5-(1,3-Dibromo-phenyl)-3-methyl-pent-2-en-4-ynyloxy]-3-bromo-phenyl}-2-ethoxy-propionic acid, (Z)-(S)-3-{4-[5-(1,3-Diiodo-phenyl)-3-methyl-pent-2-en-4-ynyloxy]-3-bromo-phenyl}-2-ethoxy-propionic acid, (Z)-(S)-3-{4-[5-(1,3-Bis-trifluoromethyl-phenyl)-3-methyl-pent-2-en-4-ynyloxy]-3-bromo-phenyl}-2-ethoxy-propionic acid, (Z)-(S)-3-{4-[5-(1,3-Dimethoxy-phenyl)-pent-2-en-4-ynyloxy]-3-bromo-phenyl}-3-methyl-2-ethoxy-propionic acid, (Z)-(S)-3-{4-[5-(1,3-Diethoxy-phenyl)-3-methyl-pent-2-en-4-ynyloxy]-3-bromo-phenyl}-2-ethoxy-propionic acid, (Z)-(S)-3-{4-[5-(1,3-Bis-(2,2,2-trifuoromethoxy)-phenyl)-3-methyl-pent-2-en-4-ynyloxy]-3-bromo-phenyl}-2-ethoxy-propionic acid, (Z)-(S)-3-{4-[5-(1,3-Bis-(2,2,2-trifluoroethoxy)-phenyl)-3-methyl-pent-2-en-4-ynyloxy]-3-bromo-phenyl}-2-ethoxy-propionic acid, (Z)-(S)-3-{4-[5-(3,5-Difluoro-phenyl)-3-methyl-pent-2-en-4-ynyloxy]-3-bromo-phenyl}-2-ethoxy-propionic acid, (Z)-(S)-3-{4-[5-(3,5-Dibromo-phenyl)-3-methyl-pent-2-en-4-ynyloxy]-3-bromo-phenyl}-2-ethoxy-propionic acid, (Z)-(S)-3-{4-[5-(3,5-Diiodo-phenyl)-3-methyl-pent-2-en-4-ynyloxy]-3-bromo-phenyl}-2-ethoxy-propionic acid, (Z)-(S)-3-{4-[5-(3,5-Bis-trifluoromethyl-phenyl)-3-methyl-pent-2-en-4-ynyloxy]-3-bromo-phenyl}-2-ethoxy-propionic acid, (Z)-(S)-3-{4-[5-(3,5-Dimethoxy-phenyl)-3-methyl-pent-2-en-4-ynyloxy]-3-bromo-phenyl}-2-ethoxy-propionic acid, (Z)-(S)-3-{4-[5-(3,5-Diethoxy-phenyl)-3-methyl-pent-2-en-4-ynyloxy]-3-bromo-phenyl}-2-ethoxy-propionic acid, (Z)-(S)-3-{4-[5-(3,5-Bis-(2,2,2-trifluoromethoxy)-phenyl)-3-methyl-pent-2-en-4-ynyloxy]-3-bromo-phenyl}-2-ethoxy-propionic acid, (Z)-(S)-3-{4-[5-(3,5-Bis-(2,2,2-trifluoroethoxy)-phenyl)-3-methyl-pent-2-en-4-ynyloxy]-3-bromo-phenyl}-2-ethoxy-propionic acid, (Z)-(S)-3-{4-[5-(1,3-Difluoro-phenyl)-pent-2-en-4-ynyloxy]-3-iodo-phenyl}-2-ethoxy-propionic acid, (Z)-(S)-3-{4-[5-(1,3-Dibromo-phenyl)-pent-2-en-4-ynyloxy]-3-iodo-phenyl}-2-ethoxy-propionic acid, (Z)-(S)-3-{4-[5-(1,3-Diiodo-phenyl)-pent-2-en-4-ynyloxy]-3-iodo-phenyl}-2-ethoxy-propionic acid, (Z)-(S)-3-{4-[5-(1,3-Bis-trifluoromethyl-phenyl)-pent-2-en-4-ynyloxy]-3-iodo-phenyl}-2-ethoxy-propionic acid, (Z)-(S)-3-{4-[5-(1,3-Dimethoxy-phenyl)-pent-2-en-4-ynyloxy]-3-iodo-phenyl}-2-ethoxy-propionic acid, (Z)-(S)-3-{4-[5-(1,3-Diethoxy-phenyl)-pent-2-en-4-ynyloxy]-3-iodo-phenyl}-2-ethoxy-propionic acid,
(Z)-(S)-3-{4-[5-(1,3-Bis-(2,2,2-trifluoromethoxy)-phenyl)-pent-2-en-4-ynyloxy]-3-iodo-phenyl}-2-ethoxy-propionic acid,
(Z)-(S)-3-{4-[5-(1,3-Bis-(2,2,2-trifluoroethoxy)-phenyl)-pent-2-en-4-ynyloxy]-3-iodo-phenyl}-2-ethoxy-propionic acid,
(Z)-(S)-3-{4-[5-(3,5-Difluoro-phenyl)-pent-2-en-4-ynyloxy]-3-iodo-phenyl}-2-ethoxy-propionic acid,
(Z)-(S)-3-{4-[5-(3,5-Dibromo-phenyl)-pent-2-en-4-ynyloxy]-3-iodo-phenyl}-2-ethoxy-propionic acid,
(Z)-(S)-3-{4-[5-(3,5-Diiodo-phenyl)-pent-2-en-4-ynyloxy]-3-iodo-phenyl}-2-ethoxy-propionic acid,
(Z)-(S)-3-{4-[5-(3,5-Bis-trifluoromethyl-phenyl)-pent-2-en-4-ynyloxy]-3-iodo-phenyl}-2-ethoxy-propionic acid,
(Z)-(S)-3-{4-[5-(3,5-Dimethoxy-phenyl)-pent-2-en-4-ynyloxy]-3-iodo-phenyl}-2-ethoxy-propionic acid,
(Z)-(S)-3-{4-[5-(3,5-Diethoxy-phenyl)-pent-2-en-4-ynyloxy]-3-iodo-phenyl}-2-ethoxy-propionic acid,
(Z)-(S)-3-{4-[5-(3,5-Bis-(2,2,2-trifluoromethoxy)-phenyl)-pent-2-en-4-ynyloxy]-3-iodo-phenyl}-2-ethoxy-propionic acid,
(Z)-(S)-3-{4-[5-(3,5-Bis-(2,2,2-trifluoroethoxy)-phenyl)-pent-2-en-4-ynyloxy]-3-iodo-phenyl}-2-ethoxy-propionic acid,
(Z)-(S)-3-{4-[5-(1,3-Difluoro-phenyl)-3-methyl-pent-2-en-4-ynyloxy]-3-iodo-phenyl}-2-ethoxy-propionic acid,
(Z)-(S)-3-{4-[5-(1,3-Dibromo-phenyl)-3-methyl-pent-2-en-4-ynyloxy]-3-iodo-phenyl}-2-ethoxy-propionic acid,
(Z)-(S)-3-{4-[5-(1,3-Diiodo-phenyl)-3-methyl-pent-2-en-4-ynyloxy]-3-iodo-phenyl}-2-ethoxy-propionic acid,
(Z)-(S)-3-{4-[5-(1,3-Bis-trifluoromethyl-phenyl)-3-methyl-pent-2-en-4-ynyloxy]-3-iodo-phenyl}-2-ethoxy-propionic acid,
(Z)-(S)-3-{4-[5-(1,3-Dimethoxy-phenyl)-pent-2-en-4-ynyloxy]-3-iodo-pheny}-3-methyl-2-ethoxy-propionic acid,
(Z)-(S)-3-{4-[5-(1,3-Diethoxy-phenyl)-3-methyl-pent-2-en-4-ynyloxy]-3-iodo-phenyl}-2-ethoxy-propionic acid,
(Z)-(S)-3-{4-[5-(1,3-Bis-(2,2,2-trifluoromethoxy)-phenyl)-3-methyl-pent-2-en-4-ynyloxy]-3-iodo-phenyl}-2-ethoxy-propionic acid,
(Z)-(S)-3-{4-[5-(1,3-Bis-(2,2,2-trifluoroethoxy)-phenyl)-3-methyl-pent-2-en-4-ynyloxy]-3-iodo-phenyl}-2-ethoxy-propionic acid,
(Z)-(S)-3-{4-[5-(3,5-Difluoro-phenyl)-3-methyl-pent-2-en-4-ynyloxy]-3-iodo-phenyl}-2-ethoxy-propionic acid,
(Z)-(S)-3-{4-[5-(3,5-Dibromo-phenyl)-3-methyl-pent-2-en-4-ynyloxy]-3-iodo-phenyl}-2-ethoxy-propionic acid,
(Z)-(S)-3-{4-[5-(3,5-Diiodo-phenyl)-3-methyl-pent-2-en-4-ynyloxy]-3-iodo-phenyl}-2-ethoxy-propionic acid,
(Z)-(S)-3-{4-[5-(3,5-Bis-trifluoromethyl-phenyl)-3-methyl-pent-2-en-4-ynyloxy]-3-iodo-phenyl}-2-ethoxy-propionic acid,
(Z)-(S)-3-{4-[5-(3,5-Dimethoxy-phenyl)-3-methyl-pent-2-en-4-ynyloxy]-3-iodo-phenyl}-2-ethoxy-propionic acid,
(Z)-(S)-3-{4-[5-(3,5-Diethoxy-phenyl)-3-methyl-pent-2-en-4-ynyloxy]-3-iodo-phenyl}-2-ethoxy-propionic acid,
(Z)-(S)-3-{4-[5-(3,5-Bis-(2,2,2-trifluoromethoxy)-phenyl)-3-methyl-pent-2-en-4-ynyloxy]-3-iodo-phenyl}-2-ethoxy-propionic acid,
(Z)-(S)-3-{4-[5-(3,5-Bis-(2,2,2-trifluoroethoxy)-phenyl)-3-methyl-pent-2-en-4-ynyloxy]-3-iodo-phenyl}-2-ethoxy-propionic acid;
or a pharmaceutically acceptable salt thereof.

31. A pharmaceutical composition comprising, as an active ingredient, a compound according to claim 1 or a pharmaceutically acceptable salt thereof together with a pharmaceutically acceptable carrier or diluent.

32. A composition according to claim 31 in unit dosage form, comprising from about 0.05 to about 100 mg of the active ingredient.

33. A pharmaceutical composition useful in the treatment of diabetes and/or obesity, the composition comprising, as an active ingredient, a compound according to claim 1 or a pharmaceutically acceptable salt thereof together with a pharmaceutically acceptable carrier or diluent.

34. A pharmaceutical composition according to claim 31 for oral, nasal, transdermal, pulmonal, or parenteral administration.

35. A method for the treatment of diabetes and/or obesity, the method comprising administering to a subject in need thereof an effective amount of a composition according to claim 31.

36. A process for the preparation of a compound of formula (I) according to claim 1 which comprises reacting a compound of formula IV

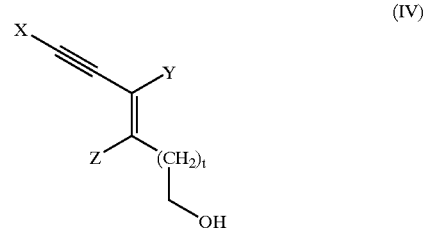

(IV)

wherein X, Y, Z are as defined in claim 1 and t is 0–2 with a compound of formula V

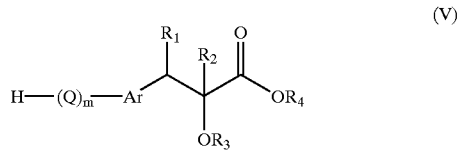

(V)

wherein Q, Ar, $R_1$, $R_2$, $R_3$, $R_4$ and m are as defined in claim 1, except that m is not 0, under Mitsunobu conditions, using a coupling reagent to obtain a compound of formula I, wherein X, Y, Z, Q, Ar, $R_1$, $R_2$, $R_3$, $R_4$, n and m are as defined in claim 1, except that $R_4$ is not H and n and m are not 0.

37. The process according to claim 36 wherein tributylphosphine and 1,1'-(azodicarbonyl) dipiperidine are used as coupling reagent and wherein either dry benzene or dry tetrahydrofuran are used as solvent.

38. A process for the preparation of a compound of formula (I) which comprises:
a) converting the —OH functionality in compound of formula IV

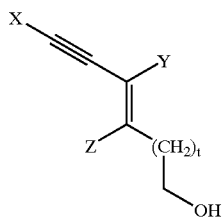

(IV)

wherein X, Y, Z and t are as defined in claim 36 to an appropriate leaving group (L), to give a compound of formula VI

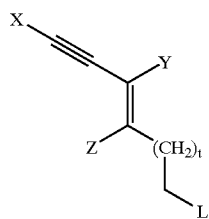

(VI)

wherein X, Y, Z and t are as defined in claim 36 and L is a leaving group, and b) reacting a compound of formula VI

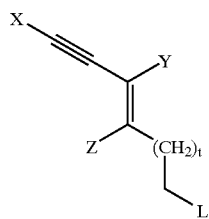

(VI)

wherein X, Y, Z and t are as defined in claim 36 and wherein L is a leaving group with a compound of formula V

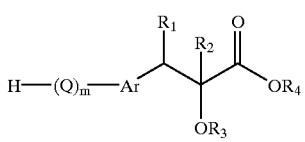

(V)

wherein Q, Ar, $R_1$, $R_2$, $R_3$, $R_4$ and m are as defined in claim 36, except that m is not 0, to give a compound of formula I wherein X, Y, Z, Q, Ar, $R_1$, $R_2$, $R_3$, $R_4$, n and m are as defined above except that $R_4$ is not H and n and m are not 0.

39. The process as in claim 38 wherein L is chlorine and wherein the reagent used in step a) are triethyl amine, dry dichloromethane and methanesulfonylchloride.

40. The process as in claim 38 wherein L is chlorine and wherein the reagents used in step b) is potassium carbonate, and sodium- or potassium iodide and wherein the solvent is acetone and wherein the reaction temperature is reflux.

41. A pharmaceutical composition suitable for treating type I. diabetes, type II diabetes, impaired glucose tolerance, insulin resistance or obesity comprising a compound according to claim 1 or a pharmaceutically acceptable salt thereof, or a pharmaceutically acceptable solvate thereof, or any tautomeric forms, stereoisomers, mixture of stereoisomers including a racemic mixture, or polymorphs together with one or more pharmaceutically acceptable carriers or diluents and an angiotensin converting enzyme inhibitor.

42. A method of treating type I diabetes, type II diabetes, impaired glucose tolerance, insulin resistance or obesity comprising administering to a subject in need thereof an effective amount of a compound according to claim 1 or a pharmaceutically acceptable salt thereof, or a pharmaceutically acceptable solvate thereof, or any tautomeric forms, stereoisomers, mixture of stereoisomers including a racemic mixture, or polymorphs together with one or more pharmaceutically acceptable carriers or diluents and an angiotensin converting enzyme inhibitor to said subject.

43. A pharmaceutical composition suitable for treating type I diabetes, type II diabetes, impaired glucose tolerance, insulin resistance or obesity comprising a compound according to claim 1 or a pharmaceutically acceptable salt thereof, or a pharmaceutically acceptable solvate thereof, or any tautomeric forms, stereoisomers, mixture of stereoisomers including a racemic mixture, or polymorphs together with one or more pharmaceutically acceptable carriers or diluents and an agent stimulating insulin release from β cells.

44. A method of treating type I diabetes, type II diabetes, impaired glucose tolerance, insulin resistance or obesity comprising administering to a subject in need thereof an effective amount of a compound according to claim 1 and an agent stimulating insulin release from β cells to said subject.

45. A pharmaceutical composition suitable for treating type I diabetes, type II diabetes, impaired glucose tolerance, insulin resistance or obesity comprising a compound according to claim 1 or a pharmaceutically acceptable salt thereof, or a pharmaceutically acceptable solvate thereof, or any tautomeric forms, stereoisomers, mixture of stereoisomers including a racemic mixture, or polymorphs together with one or more pharmaceutically acceptable carriers or diluents and a biguanide.

46. A method of treating type I diabetes, type II diabetes, impaired glucose tolerance, insulin resistance or obesity comprising administering to a subject in need thereof an effective amount of a compound according to claim 1 or a pharmaceutically acceptable salt thereof, or a pharmaceutically acceptable solvate thereof, or any tautomeric forms, stereoisomers, mixture of stereoisomers including a racemic mixture, or polymorphs together with one or more pharmaceutically acceptable carriers or diluents and a biguanide to said subject.

47. A pharmaceutical composition suitable for treating type I diabetes, type II diabetes, impaired glucose tolerance, insulin resistance or obesity comprising a compound according to claim 1 or a pharmaceutically acceptable salt thereof, or a pharmaceutically acceptable solvate thereof, or any tautomeric forms, stereoisomers, mixture of stereoisomers including a racemic mixture, or polymorphs together with one or more pharmaceutically acceptable carriers or diluents and an antihyperlipidemic or antilipidemic agent.

48. A method of treating type I diabetes, type II diabetes, impaired glucose tolerance, insulin resistance or obesity comprising administering to a subject in need thereof an effective amount of a compound according to claim 1 or a pharmaceutically acceptable salt thereof, or a pharmaceutically acceptable solvate thereof, or any tautomeric forms, stereoisomers, mixture of stereoisomers including a racemic mixture, or polymorphs together with one or more pharmaceutically acceptable carriers or diluents and an antihyperlipidemic or antilipidemic agent to said subject.

49. A pharmaceutical composition useful in the treatment of conditions mediated by the Peroxisome Proliferator- Activated Receptors (PPAR), the composition comprising, as an active ingredient, a compound according to claim 1 or a pharmaceutically acceptable salt thereof together with a pharmaceutically acceptable carrier or diluent.

50. A method for the treatment of conditions mediated by the Peroxisome Proliferator-Activated Receptors (PPAR), the method comprising administering to a subject in need thereof an effective amount of a composition according to claim 31.

51. The process as in claim 38 wherein L is selected from the group consisting of p-toluenesulfonate, methanesulfonate, halogen and triflate.

52. The pharmaceutical composition according to claim 43, wherein the agent stimulating insulin release from β cells is meglitinide.

53. The pharmaceutical composition according to claim 43, wherein the agent stimulating insulin release from β cells is repaglinide or senaglinide.

54. The method according to claim 44, wherein the agent stimulating insulin release from β cells is a meglitinide.

55. The method according to claim 44, wherein agent stimulating insulin release from β cells is repaglinide or senaglinide.

56. The pharmaceutical composition according to claim 45, wherein the biguanide is metformin.

57. The method according to claim 46, wherein the biguanide is metformin.

58. The pharmaceutical composition according to claim 47, wherein the antihyperlipidemic or antilipidemic agent is a statin.

59. The method according to claim 48, wherein the antihyperlipidemic or antilipidemic agent is a statin.

60. The method according to claim 50, wherein the effective amount of the composition is in the range of from about 0.05 to about 100 mg per day.

* * * * *